US011311219B2

(12) United States Patent
Rogers et al.

(10) Patent No.: US 11,311,219 B2
(45) Date of Patent: *Apr. 26, 2022

(54) BLOOD SAMPLE OPTIMIZATION SYSTEM AND BLOOD CONTAMINANT SEQUESTRATION DEVICE AND METHOD

(71) Applicant: KURIN, INC., San Diego, CA (US)

(72) Inventors: Bobby E. Rogers, San Diego, CA (US); Gino Kang, San Diego, CA (US); David Karl Stroup, San Diego, CA (US); Jonas Dean Cochran, Santee, CA (US); Arthur Deptala, Santee, CA (US); John Detloff, San Diego, CA (US); Lonnie Pogue, San Diego, CA (US); Brian Macowski, San Diego, CA (US)

(73) Assignee: Kurin, Inc., San Diego, CA (US)

( * ) Notice: Subject to any disclaimer, the term of this patent is extended or adjusted under 35 U.S.C. 154(b) by 836 days.

This patent is subject to a terminal disclaimer.

(21) Appl. No.: 15/855,439

(22) Filed: Dec. 27, 2017

(65) Prior Publication Data

US 2018/0177445 A1 Jun. 28, 2018

Related U.S. Application Data

(60) Provisional application No. 62/439,426, filed on Dec. 27, 2016.

(51) Int. Cl.
*A61B 5/15* (2006.01)
*A61B 5/153* (2006.01)
(Continued)

(52) U.S. Cl.
CPC .... *A61B 5/150755* (2013.01); *A61B 5/15003* (2013.01); *A61B 5/1535* (2013.01);
(Continued)

(58) Field of Classification Search
CPC ...... A61M 2039/205; A61M 2039/266; A61M 2039/0202; A61M 2005/1587;
(Continued)

(56) References Cited

U.S. PATENT DOCUMENTS

| 3,648,684 A | 3/1972 | Barnwell et al. |
| 3,741,197 A | 6/1973 | Sanz et al. |

(Continued)

FOREIGN PATENT DOCUMENTS

| CA | 2993646 A1 | 2/2017 |
| EP | 1665986 B1 | 6/2009 |

(Continued)

OTHER PUBLICATIONS

International Search Report and Written Opinion dated Jun. 19, 2020, for PCT application No. PCTUS2020/023617.

(Continued)

*Primary Examiner* — Devin B Henson
*Assistant Examiner* — H. Q. Nguyen
(74) *Attorney, Agent, or Firm* — James S. Nolan

(57) ABSTRACT

Blood sample optimization systems and methods are described that reduce or eliminate contaminates in collected blood samples, which in turn reduces or eliminates false positive readings in blood cultures or other testing of collected blood samples. A blood sample optimization system can include a blood sequestration device located between a patient needle and a sample needle. The blood sequestration device can include a sequestration chamber for sequestering an initial, potentially contaminated aliquot of blood, and may further include a sampling channel that bypasses the sequestration chamber to convey likely uncontaminated blood between the patient needle and the sample needle after the initial aliquot of blood is sequestered in the sequestration chamber.

20 Claims, 69 Drawing Sheets

(51) Int. Cl.
*A61B 5/154* (2006.01)
*A61B 5/157* (2006.01)

(52) U.S. Cl.
CPC ...... *A61B 5/1545* (2013.01); *A61B 5/150213* (2013.01); *A61B 5/150221* (2013.01); *A61B 5/150251* (2013.01); *A61B 5/150274* (2013.01); *A61B 5/150351* (2013.01); *A61B 5/150786* (2013.01); *A61B 5/150946* (2013.01); *A61B 5/150992* (2013.01); *A61B 5/157* (2013.01); *A61B 5/150389* (2013.01); *A61B 5/150488* (2013.01)

(58) Field of Classification Search
CPC ...... A61M 2005/3123; A61M 5/16804; A61M 1/0236; A61B 10/0045; A61B 5/153–154; A61B 5/1535; A61B 5/1545; A61B 5/157; A61B 5/150992; A61B 5/15003; A61B 5/150946; A61B 5/150213; A61B 5/150221; A61B 5/150251; A61B 5/150351
See application file for complete search history.

(56) References Cited

U.S. PATENT DOCUMENTS

| | | | |
|---|---|---|---|
| 3,817,240 A | 6/1974 | Ayres | |
| 3,874,367 A | 4/1975 | Ayres | |
| 3,886,930 A | 6/1975 | Ryan | |
| 4,056,101 A | 11/1977 | Geissler et al. | |
| 4,057,050 A | 11/1977 | Sarstedt | |
| 4,106,497 A | 8/1978 | Percarpio | |
| 4,154,229 A | 5/1979 | Nugent | |
| 4,207,870 A | 6/1980 | Eldridge | |
| 4,349,035 A | 9/1982 | Thomas et al. | |
| 4,412,548 A | 11/1983 | Hoch | |
| 4,416,290 A | 11/1983 | Lutkowski | |
| 4,444,203 A | 4/1984 | Engelman | |
| 4,813,433 A | 3/1989 | Downey | |
| 5,222,502 A | 6/1993 | Kurose | |
| 5,401,262 A | 3/1995 | Karwoski et al. | |
| 5,520,193 A | 5/1996 | Suzuki et al. | |
| 5,749,857 A | 5/1998 | Cuppy | |
| 6,398,743 B1 | 6/2002 | Halseth et al. | |
| 6,569,117 B1 | 5/2003 | Ziv et al. | |
| 8,070,725 B2 | 12/2011 | Christensen | |
| 8,197,420 B2 | 6/2012 | Patton | |
| 8,523,826 B2 | 9/2013 | Layton, Jr. | |
| 8,535,241 B2 | 9/2013 | Bullington et al. | |
| 8,540,663 B2 | 9/2013 | Davey et al. | |
| 8,568,371 B2 | 10/2013 | Siopes et al. | |
| 8,603,009 B2 | 12/2013 | Tan et al. | |
| 8,864,684 B2 | 10/2014 | Bullington et al. | |
| 9,022,950 B2 | 5/2015 | Bullington et al. | |
| 9,022,951 B2 | 5/2015 | Bullington et al. | |
| 9,060,724 B2 | 6/2015 | Bullington et al. | |
| 9,138,572 B2 | 9/2015 | Zeytoonian et al. | |
| 9,155,495 B2 | 10/2015 | Bullington et al. | |
| 9,204,864 B2 | 12/2015 | Bullington et al. | |
| 9,820,682 B2 | 11/2017 | Rogers et al. | |
| 9,877,675 B2 | 1/2018 | Baid | |
| 10,010,282 B2 | 7/2018 | Rogers et al. | |
| 10,143,412 B2 | 12/2018 | Rogers et al. | |
| 10,827,964 B2 * | 11/2020 | Rogers ............. | A61B 5/150732 |
| 2002/0004647 A1 | 1/2002 | Leong | |
| 2003/0105414 A1 | 6/2003 | Leong | |
| 2003/0208151 A1 | 11/2003 | Kraus et al. | |
| 2004/0054333 A1 | 3/2004 | Theeuwes et al. | |
| 2004/0073171 A1 | 4/2004 | Rogers et al. | |
| 2004/0147855 A1 | 7/2004 | Marsden | |
| 2005/0004524 A1 | 1/2005 | Newby et al. | |
| 2005/0005635 A1 | 1/2005 | Metais | |
| 2005/0007524 A1 | 1/2005 | Luo et al. | |
| 2005/0240161 A1 | 10/2005 | Crawford | |
| 2007/0083162 A1 | 4/2007 | O'Reagan et al. | |
| 2007/0088279 A1 | 4/2007 | Shue et al. | |
| 2008/0086085 A1 | 4/2008 | Brown | |
| 2008/0145933 A1 | 6/2008 | Patton | |
| 2008/0167577 A1 | 7/2008 | Weilbacher et al. | |
| 2008/0319346 A1 | 12/2008 | Crawford et al. | |
| 2009/0227953 A1 | 9/2009 | Tan et al. | |
| 2010/0010372 A1 | 1/2010 | Brown et al. | |
| 2010/0057004 A1 | 3/2010 | Christensen et al. | |
| 2012/0016266 A1 | 1/2012 | Burkholz | |
| 2013/0317391 A1 | 11/2013 | Bullington et al. | |
| 2014/0039348 A1 | 2/2014 | Bullington et al. | |
| 2014/0107564 A1 | 4/2014 | Bullington et al. | |
| 2014/0155782 A1 | 6/2014 | Bullington et al. | |
| 2014/0276578 A1 | 9/2014 | Bullington et al. | |
| 2015/0246352 A1 | 9/2015 | Bullington et al. | |
| 2015/0342510 A1 | 12/2015 | Bullington et al. | |
| 2016/0008579 A1 | 1/2016 | Burkholz et al. | |
| 2016/0017488 A1 | 1/2016 | Kobayashi et al. | |
| 2016/0174888 A1 | 6/2016 | Berthier et al. | |
| 2016/0361006 A1 | 12/2016 | Bullington et al. | |
| 2017/0020427 A1 | 1/2017 | Rogers et al. | |
| 2017/0020428 A1 | 1/2017 | Rogers et al. | |
| 2017/0065733 A1 | 3/2017 | Bullington et al. | |
| 2018/0140240 A1 | 5/2018 | Bullington et al. | |
| 2018/0177445 A1 | 6/2018 | Rogers et al. | |
| 2018/0271425 A1 | 9/2018 | Rogers et al. | |
| 2018/0353117 A1 | 12/2018 | Bullington et al. | |
| 2019/0159711 A1 | 5/2019 | Rogers et al. | |

FOREIGN PATENT DOCUMENTS

| | | |
|---|---|---|
| EP | 3324845 B1 | 10/2019 |
| EP | 3622890 A1 | 10/2019 |
| EP | 3562397 B1 | 9/2020 |
| JP | H08257018 A | 10/1996 |
| JP | H09504726 A | 5/1997 |
| JP | 2001000424 A | 1/2001 |
| JP | 2012016496 A | 1/2012 |
| JP | 5789869 B2 | 10/2015 |
| JP | 5867238 B2 | 2/2016 |
| JP | 2016504075 A | 2/2016 |
| JP | 2019534792 A | 12/2019 |
| JP | 6643474 B2 | 2/2020 |
| JP | 6734490 B2 | 8/2020 |
| WO | 9605875 A1 | 2/1996 |
| WO | 2011162772 A1 | 12/2011 |
| WO | 2013181352 A1 | 12/2013 |
| WO | 2014058945 A1 | 4/2014 |
| WO | 2017019552 A1 | 2/2017 |
| WO | 2018125929 A1 | 7/2018 |
| WO | 2019055487 A1 | 3/2019 |
| WO | 2019232196 A1 | 12/2019 |

OTHER PUBLICATIONS

Bullington, et al., Systems and Methods for Sample Collection with Reduced Hemolysis, Exhibit H in U.S. Appl. No. 62/517,681, dated Jun. 9, 2017, 131 pages.
Communication Under Rule 71(3) EPC dated Apr. 22, 2020 for EP application No. 17840467.9.
European Patent Application No. EP19200766.4 extended European Search Report dated Dec. 2, 2019, 11 pages.
European Patent Office; Communication pursuant to Article 94(3) EPC; dated Oct. 31, 2018; 11 pages.
Examination Report No. 1 dated Apr. 29, 2020, for Australian Patent Application No. 2016297849.
International Search Report and Written Opinion for PCT/US16/43709, dated Oct. 19, 2016.
International Search Report/Written Opinion for PCT/US17/68569 dated Apr. 25, 2018.
Japanese Patent Office, Notice of Reasons for Rejection, Japanese patent application No. JP2018-523384, dated Jul. 23, 2019, 5 pages.
European Patent Office, Extended European Search Report for European Patent Application 20197213.0-1132, dated Dec. 9, 2020, 6 pages.

(56) References Cited

OTHER PUBLICATIONS

Japanese Patent Office, Notice of Reasons for Rejection dated Jun. 15, 2021, Application No. JP 2019-534792, 4 pages.
Japanese Patent Office, Notice of Reasons for Rejection for JP Application No. JP 2020-118498 date Aug. 10, 2021.

* cited by examiner

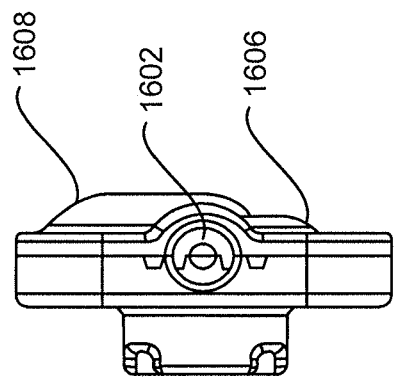
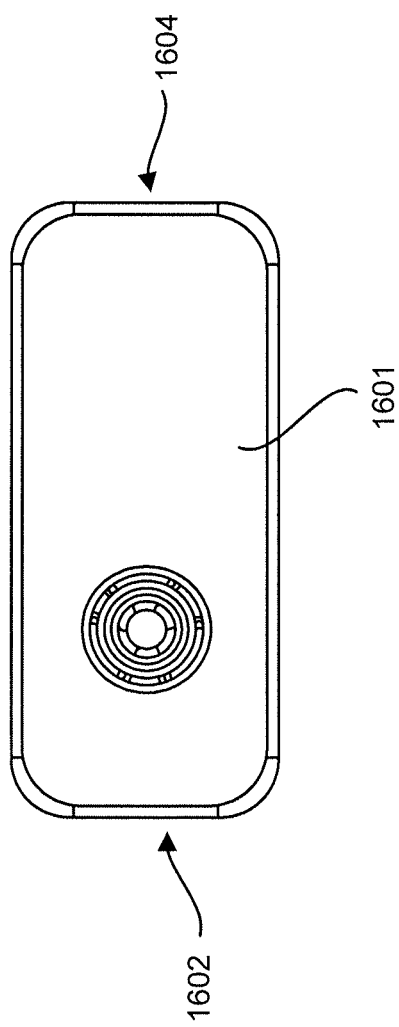
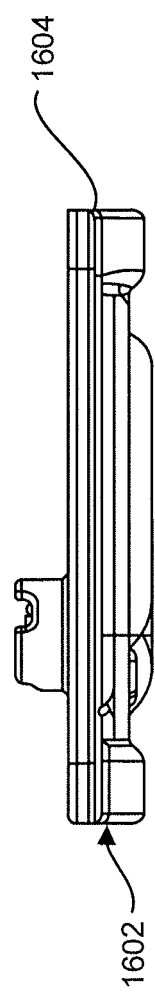
FIG. 16C
FIG. 16A
FIG. 16B

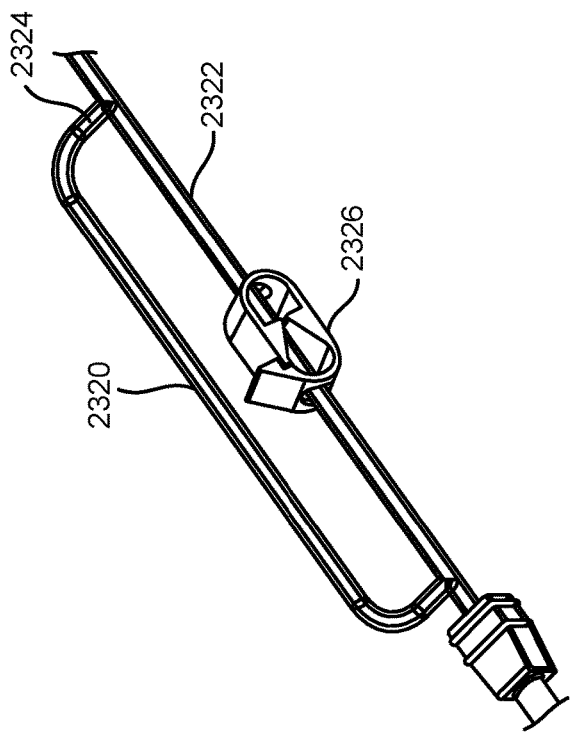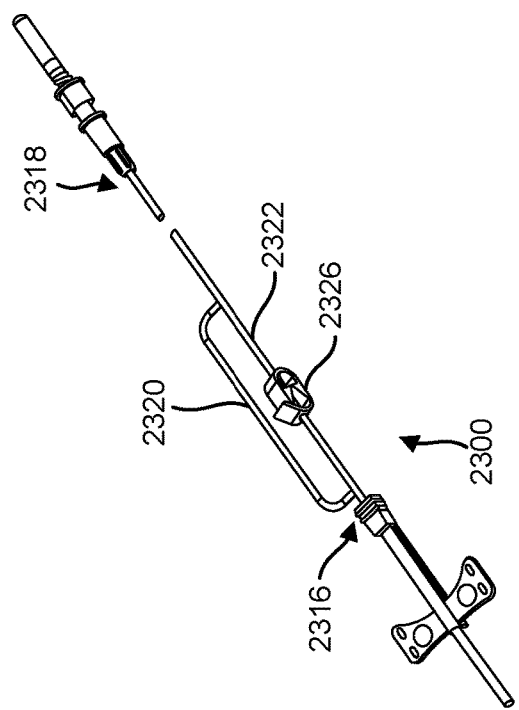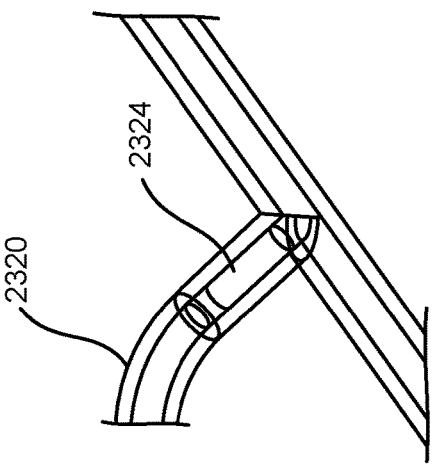

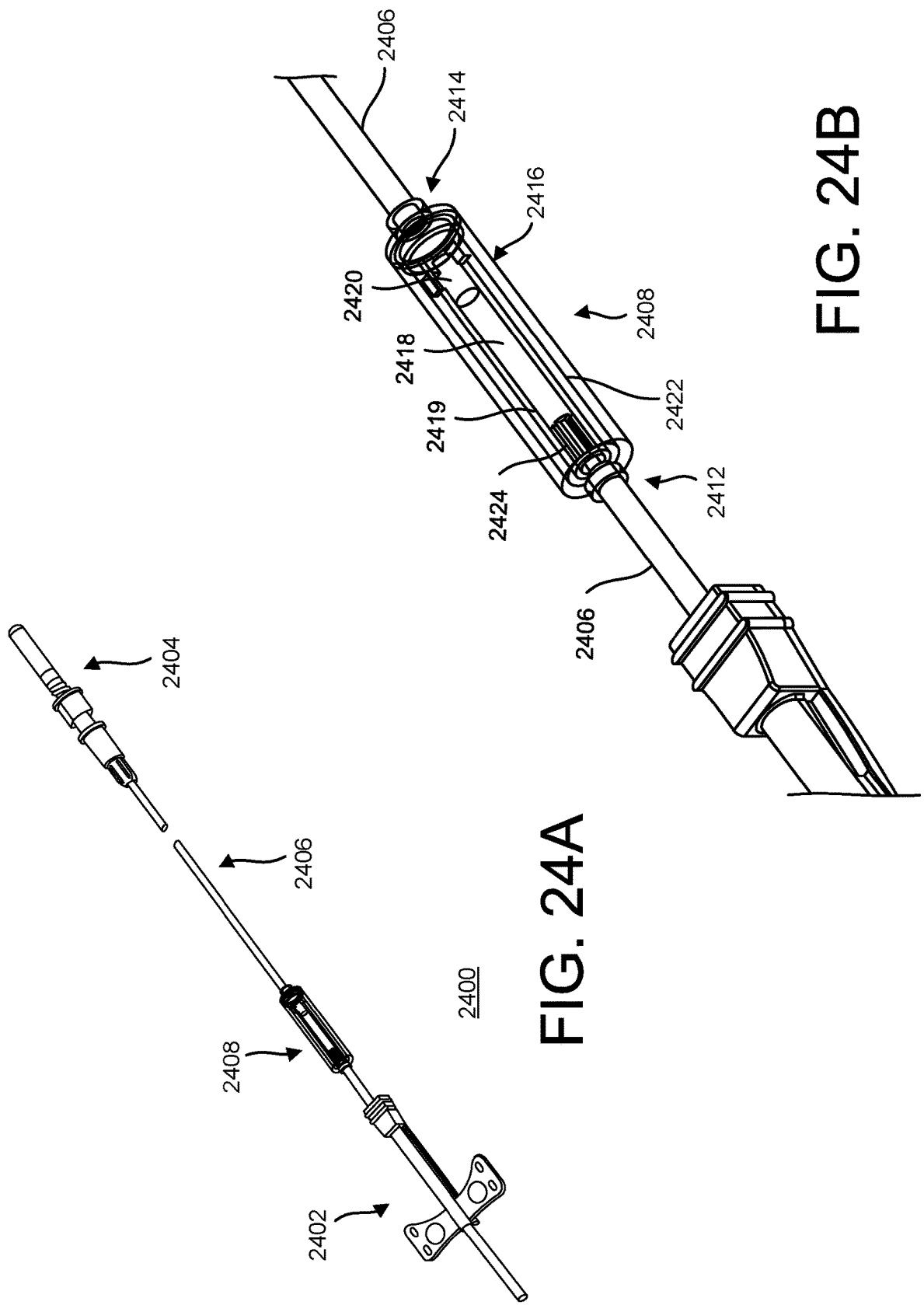

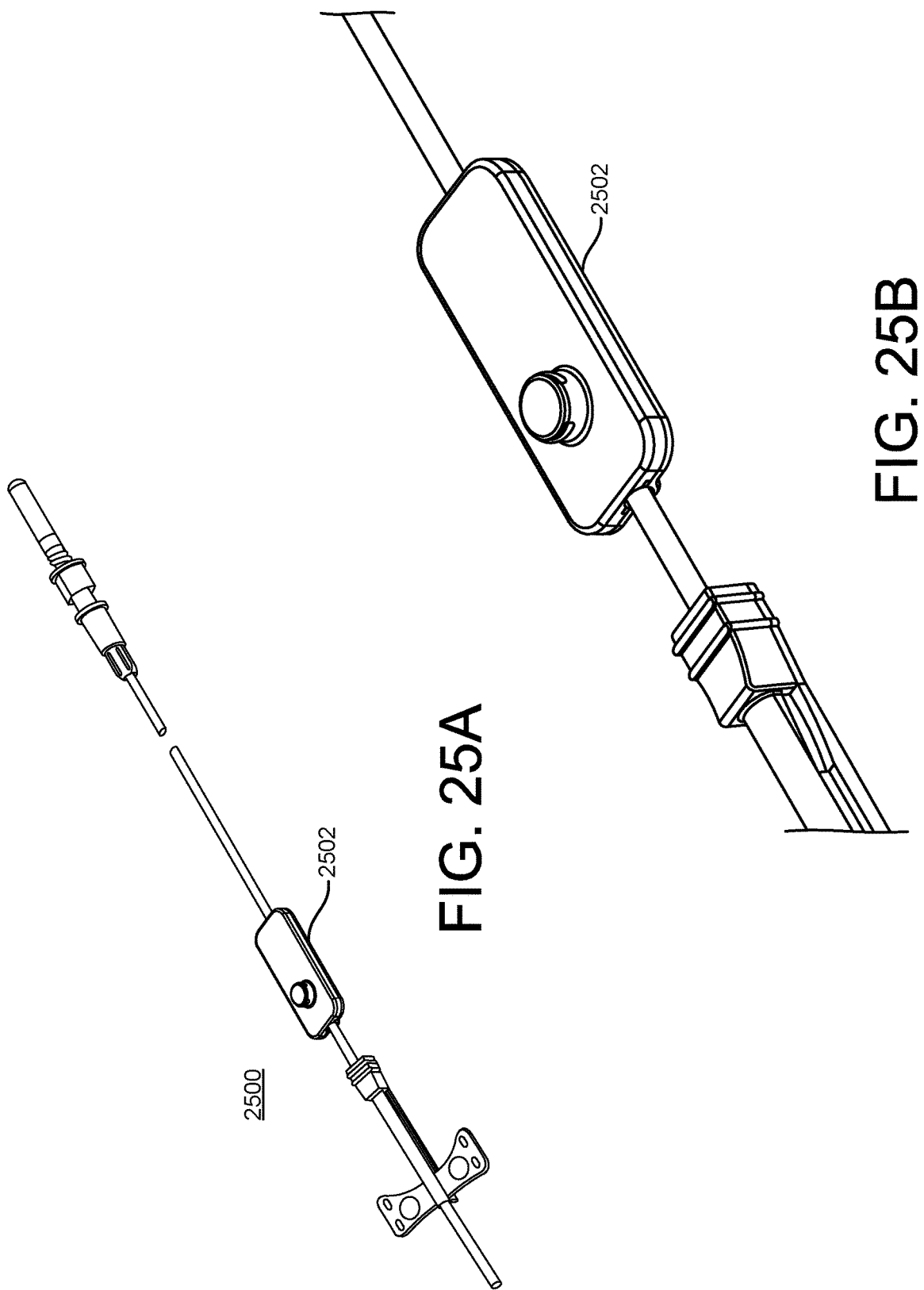

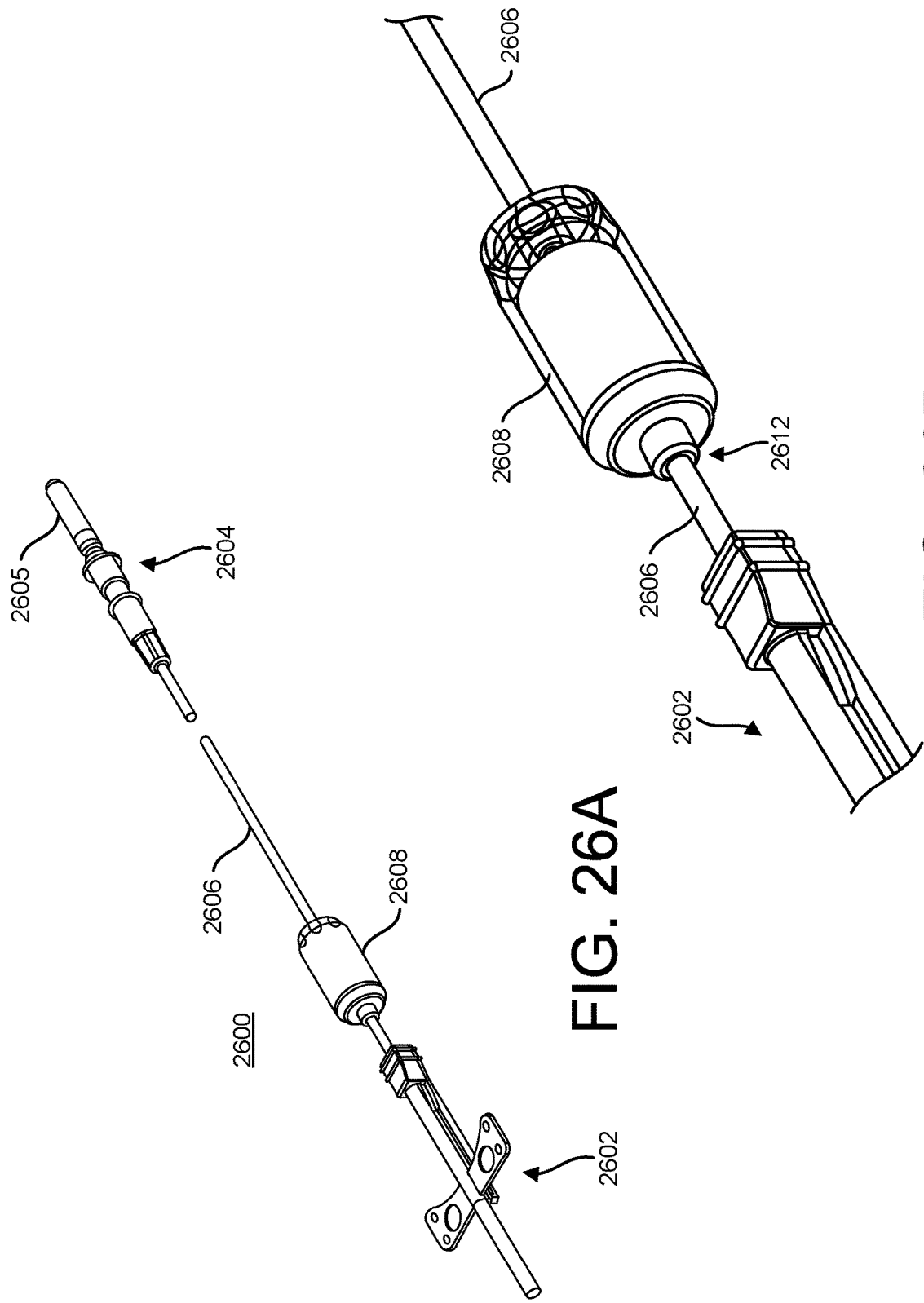

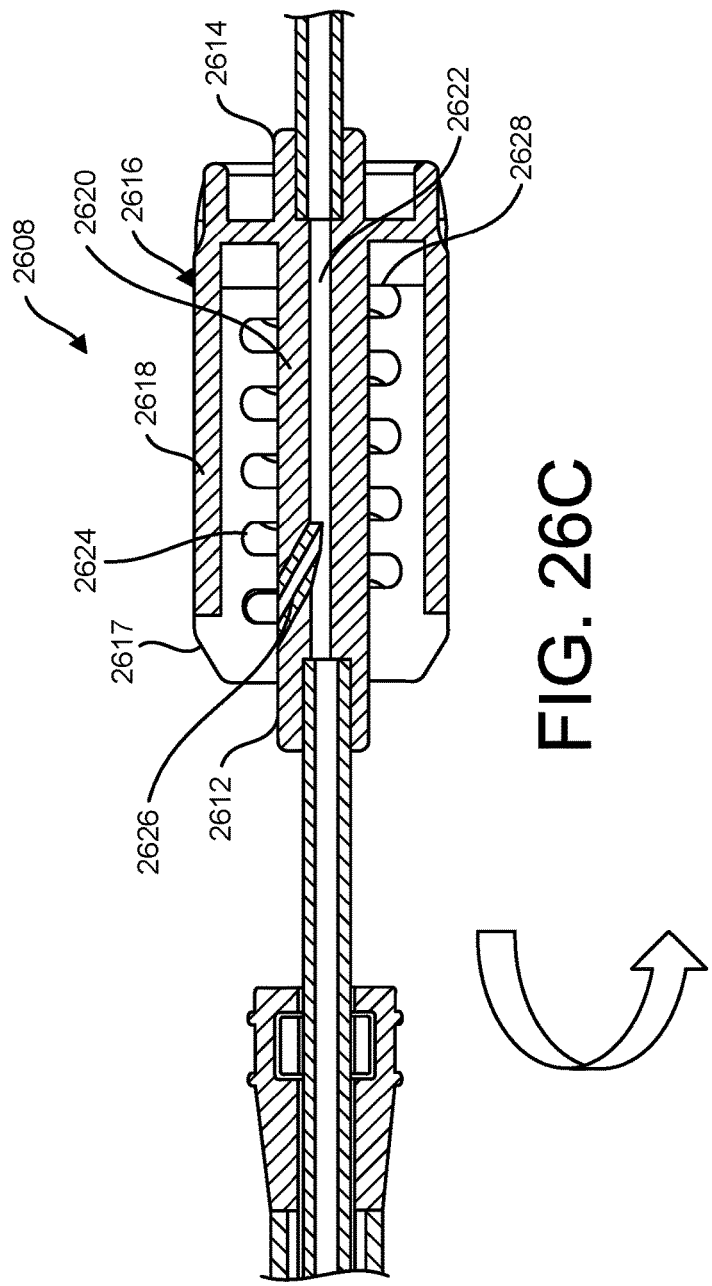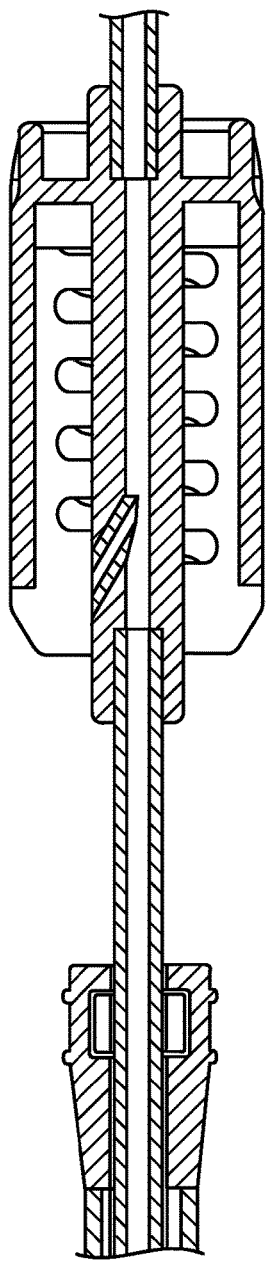

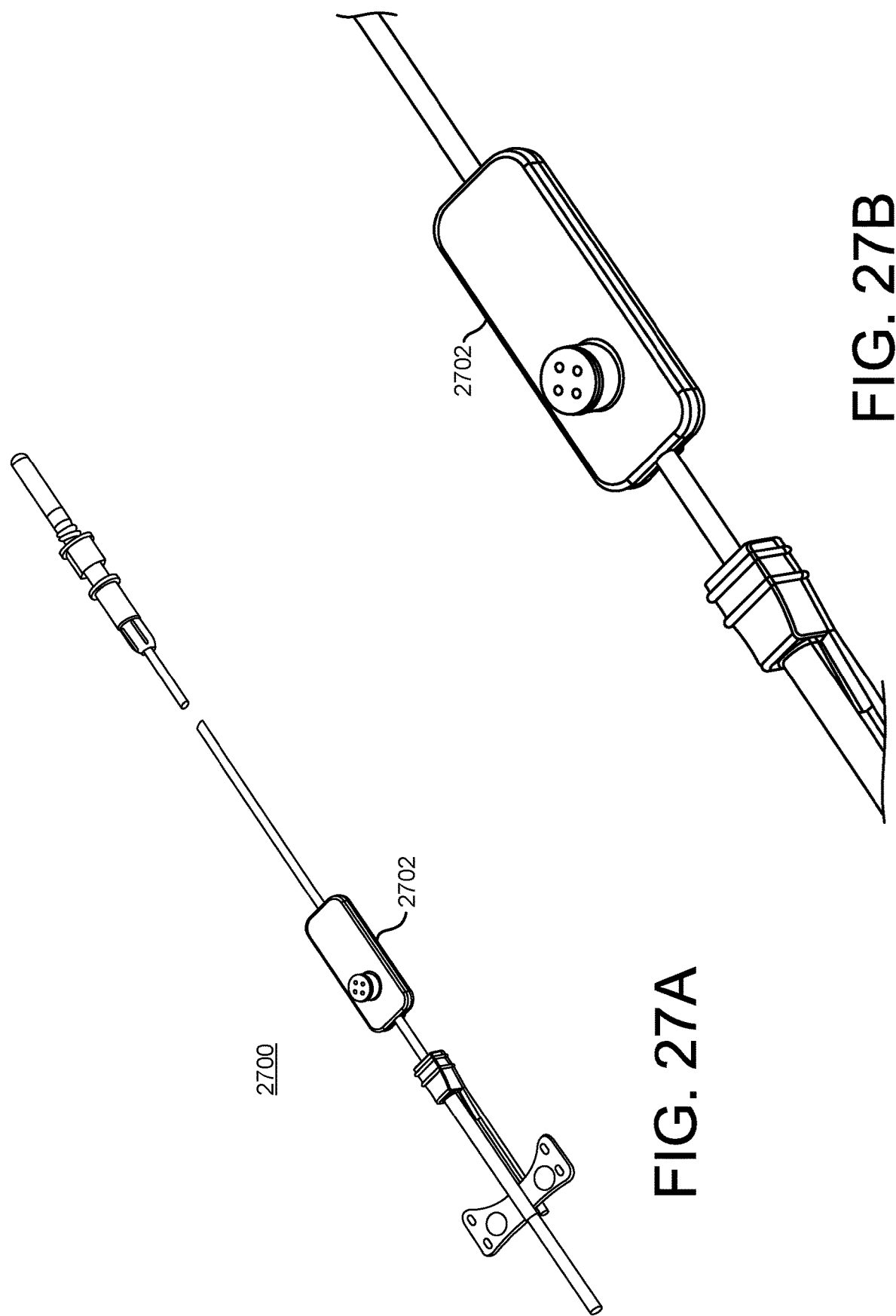

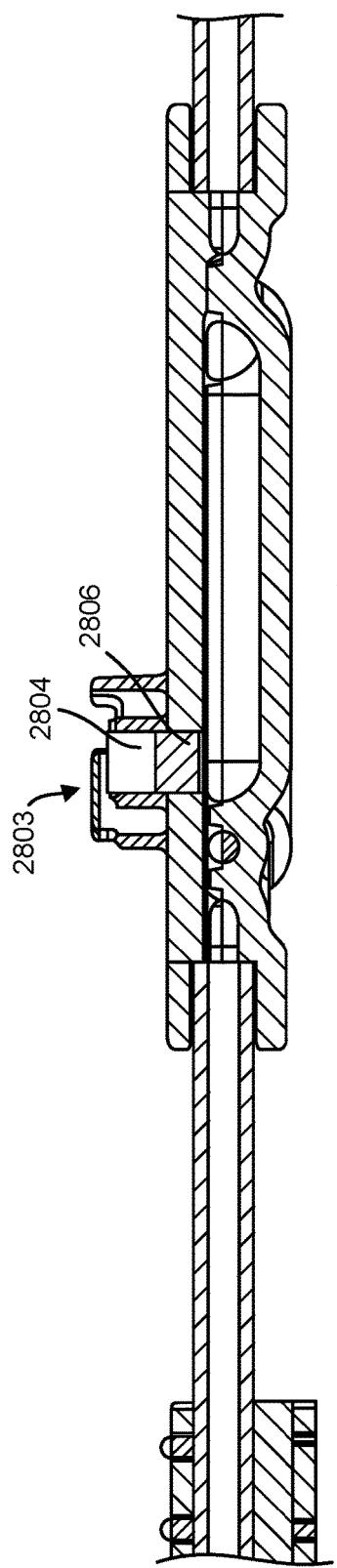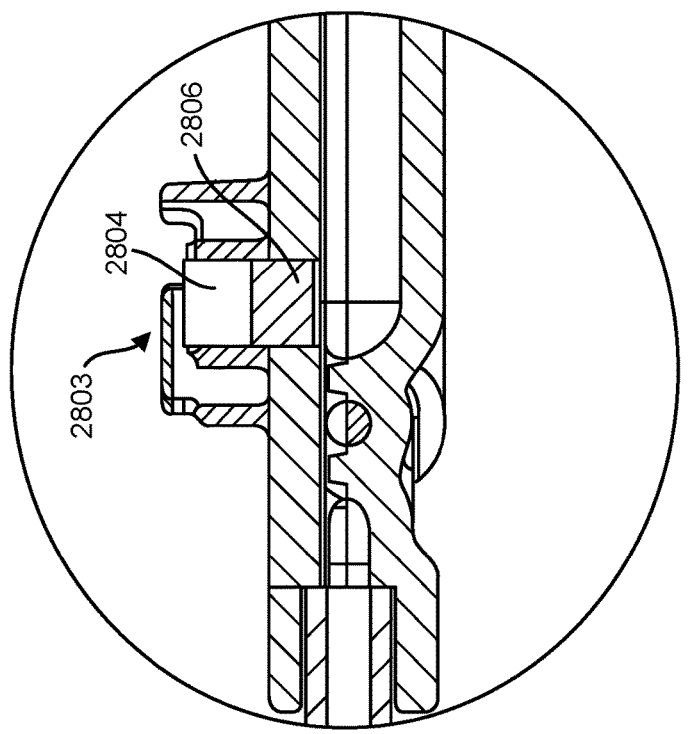

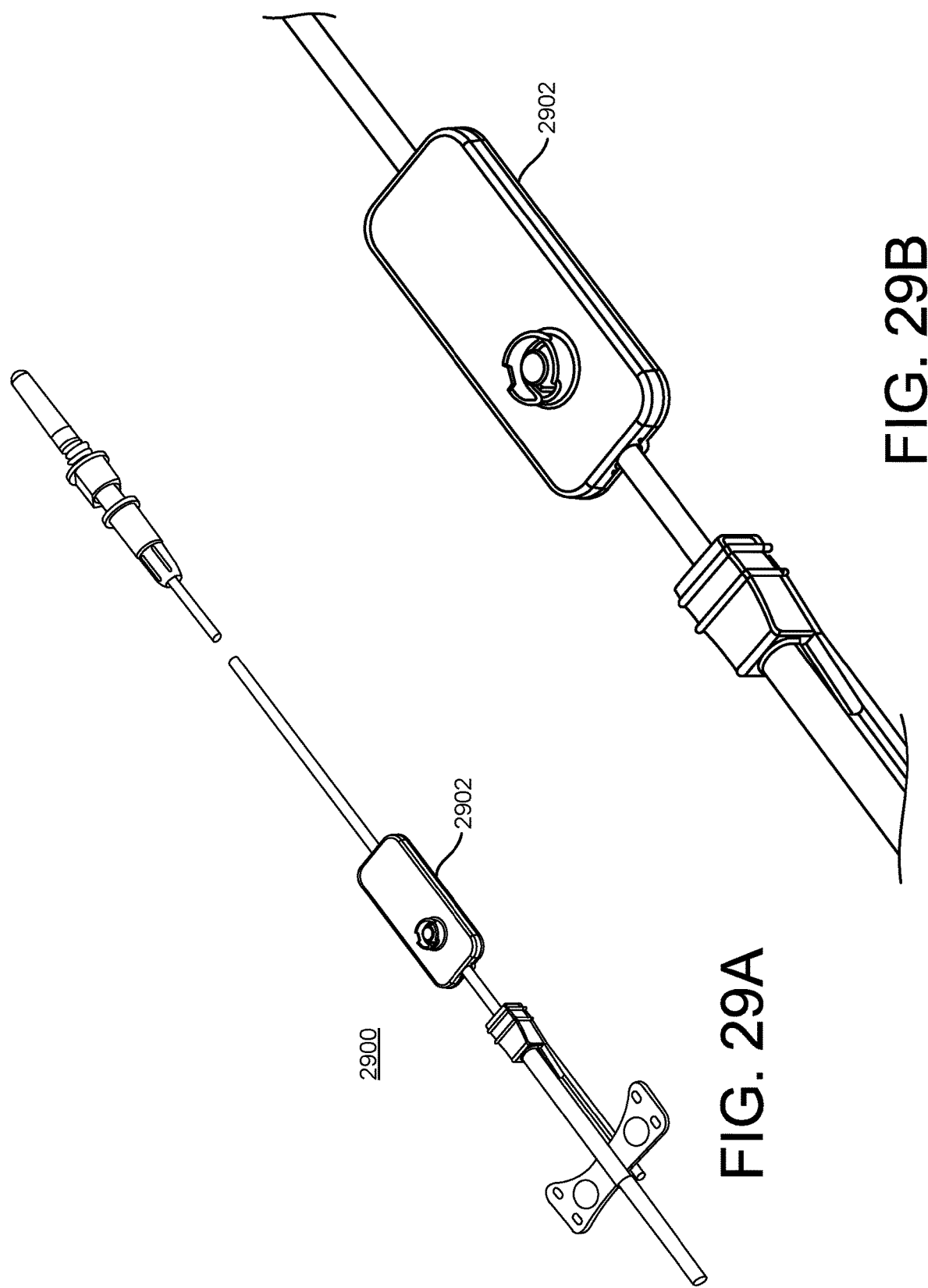

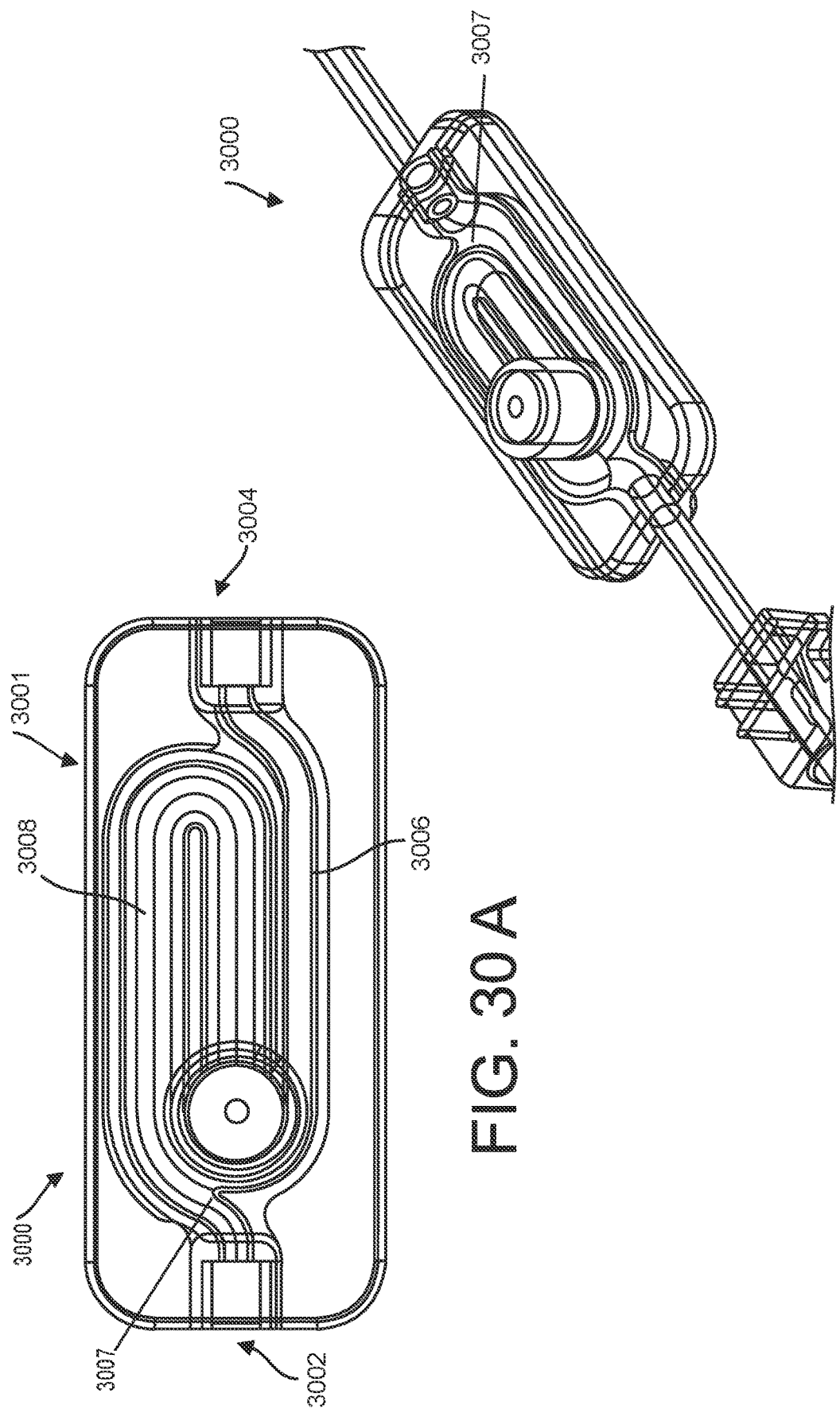

BLOOD SAMPLE OPTIMIZATION SYSTEM AND BLOOD CONTAMINANT SEQUESTRATION DEVICE AND METHOD

The present application claims priority from U.S. Provisional Patent Application No. 62/439,426, filed Dec. 27, 2016, entitled "BLOOD SAMPLE OPTIMIZATION SYSTEM AND BLOOD CONTAMINANT SEQUESTRATION DEVICE AND METHOD", the disclosure of which is incorporated herein by reference in its entirety.

BACKGROUND

Bacteraemia is the presence of microorganisms in the blood. Sepsis, on the other hand, is bacteraemia in the presence of clinical symptoms and signs such as fever, tachycardia, tachypnea and hypotension. Bacteraemia and sepsis are associated with a high mortality and an increased incidence and duration of hospital stay and associated costs. Many bacteraemias, sepsis, fungaemias and other pathogens actually occur within a hospital or other healthcare settings with catheters and venipunctures being a source of contamination as potential carriers of these pathogens.

Blood cultures are the standard test used to detect microbial pathogens related to bacteraemia and sepsis in a patient's blood. The term blood culture refers to a single venipuncture, either from a peripheral site or central or arterial line, with the blood inoculated into one or more blood culture bottles or containers. One bottle is considered a blood culture where two or more are considered a set. Multiple sets may be obtained from multiple venipunctures and are associated with different sites on the patient.

These methods allow for microbial identification and susceptibility testing to be performed, which is a critical component to managing sepsis, however the lack of rapid results and decreased sensitivity for fastidious pathogens has led to the development of improved systems and adjunctive molecular or proteomic testing.

Collection of blood samples for conducting blood cultures is a critical component of modern patient care and can either positively affect the patient outcome by providing an accurate diagnosis, or can adversely affect the outcome by prolonging unnecessary antimicrobial therapy, the length of hospital stays, and increasing costs.

One outcome of collection of blood cultures is contamination. Blood culture contamination can lead to a false positive culture result and/or significant increase in healthcare related costs. Sources of blood culture contamination include improper skin antisepsis, improper collection tube disinfection, and contamination of the initial blood draw which may then skew results.

Blood culture collection kits generally consist of a "butterfly" set, infusion set, or other type of venipuncture device as offered by companies like BD, Smiths, B. Braun and others, and aerobic and anaerobic blood culture bottles. Various different bottles are also available depending on the test requirements. These bottles are specifically designed to optimize recovery of both aerobic and anaerobic organisms. In conventional kits, a bottle used is known generally as a "Vacutainer," which is a blood collection tube formed of a sterile glass or plastic tube with a closure that is evacuated to create a vacuum inside the tube to facilitate the draw of a predetermined volume of liquid such as blood.

False positive blood cultures are typically a result of poor sampling techniques. They cause the use of antibiotics when not needed, increasing hospital costs and patient anxiety. Blood cultures are drawn from a needlestick into the skin, and then a Vacutainer is attached to capture a sample of blood. Contamination may occur from improper or incomplete disinfection of the skin area in and around the puncture site. It may also occur from the coring of the skin by the needle during insertion, with the cored skin cells and any associated contamination being pulled into the sample.

Blood flow through a hypodermic needle is laminar, and as such, a velocity gradient can be developed over the flow tube as a pressure drop is applied to the hypodermic needle. Either forceful aspiration of blood, or using a very small hypodermic needle, can cause lysis and a release of potassium from the red blood cells, thereby rendering the blood samples abnormal.

In other instances, some patients have delicate veins that can collapse under a pressure drop or vacuum, particularly as applied by a syringe's plunger that is drawn too quickly for the patient's condition. Since such condition is impossible to know beforehand, such vein collapses are a risk and very difficult to control.

Various strategies have been implemented to decrease blood culture contamination rates, e.g. training staff with regard to aseptic collection technique, feedback with regard to contamination rates and implementation of blood culture collection kits. Although skin antisepsis can reduce the burden of contamination, 20% or more of skin organisms are located deep within the dermis and are unaffected by antisepsis. Changing needles before bottle inoculation is not advisable as it increases the risk to acquire needle stick injuries without decreasing contamination rates.

Some conventional systems and techniques for reducing blood culture contamination include discarding the initial aliquot of blood taken from central venous catheters, venipunctures, and other vascular access systems. However, these systems require the user to mechanically manipulate an intravascular device, or require a complex series of steps that are difficult to ensure being followed.

SUMMARY

This document presents systems and methods for reducing blood culture contamination, lysing of cells, and vein collapse. In some implementations, a system and method can eliminate user variability in disinfection, and also eliminate the risk of skin cells getting into the blood culture sample. The systems and methods disclosed herein do not require a change in existing clinical processes, other than to potentially indicate when a vacutainer or other blood collection device (i.e., syringe) should be attached for drawing contaminant-free blood samples.

In some implementations of the systems and methods disclosed herein the withdrawal of blood is accomplished passively by use of the patient's own blood pressure, thereby reducing the risk of vein collapse and eliminating any additional user steps over current practice. The systems and methods can be applied to accommodate short-path direct stick or butterfly venipuncture systems. They can also be used with samples drawn through a catheter.

In one aspect, a blood sequestration device is presented. The blood sequestration device includes an inlet port and an outlet port. The blood sequestration device further includes a sequestration chamber connected with the inlet port, the sequestration chamber having a vent comprising an air permeable blood barrier. The blood sequestration device further includes a sampling channel having a proximal end connected with the inlet port and a distal end connected with the outlet port.

In another aspect, a blood sequestration device connected with a blood sampling pathway is described. The blood sampling pathway has a patient needle and a sample collection device. The blood sequestration device includes an inlet port connected with the patient needle, and a sequestration chamber connected with the inlet port, the sequestration chamber having a vent comprising an air permeable blood barrier. The blood sequestration device further includes a sampling channel having a proximal end connected with the inlet port, and an outlet port connected with a distal end of the sampling channel and with the sample collection device.

In yet another aspect, a blood sequestration device connected with a blood sampling system is described. The blood sampling system includes a patient needle for accessing a blood sample from a patient, and a sample needle that is sealed and adapted for receiving an evacuated blood collection tube. The blood sequestration device includes an inlet port connected with the patient needle to receive the blood sample from the patient. The blood sequestration device further includes a sequestration chamber connected with the inlet port and having a vent comprising an air permeable blood barrier, the sequestration chamber for receiving and sequestering a first portion of the blood sample prior to the sample needle being unsealed by the evacuated blood collection tube. The blood sequestration device further includes a sampling channel having a proximal end connected with the inlet port, the sampling channel for conveying a subsequent portion of the blood sample once the sample needle is unsealed by the evacuated blood collection tube. The blood sequestration device further includes an outlet port connected with a distal end of the sampling channel for conveying the subsequent portion of the blood sample to the sample needle.

In yet another aspect, a blood sample optimization system is disclosed and described. The blood sample optimization system includes a blood sampling system for accessing and acquiring one or more samples of a patient's blood, and a blood sequestration device for receiving and sequestering a first portion of the one or more samples of the patient's blood which might be contaminated by a venipuncture process and which could result in a false positive identification of a pathogen in the patient's blood.

The blood sampling system includes a patient needle configured for a venipuncture of a patient to access a sample of blood of a patient, a blood sampling pathway connected with the patient needle for conveying the sample of blood, and a sample needle configured for receiving an evacuated blood collection container to collect and contain a subsequent portion of the sample of blood.

In yet another aspect, a blood sequestration device is disclosed and described. In some implementations, the blood sequestration device can include an inlet port, an outlet port connected with the inlet port, and a sequestration chamber connected with the inlet port. The sequestration chamber can have a vent comprising an air permeable blood barrier.

The blood sequestration device, in one aspect can include an inlet port, an outlet port, a sequestration chamber connected with the inlet port via a junction, the sequestration chamber having a vent that includes an air permeable blood barrier, the vent being defined by an outer wall that at least partially circumscribes the air permeable blood barrier and includes one or more air vents, the vent further includes a cap that at least partially covers the wall and a one-way seal abutting the air permeable blood barrier that inhibits air from entering the sequestration chamber, and a sampling channel having a proximal end connected with the inlet port via the junction, and a distal end connected with the outlet port. In certain related aspects, the sequestration chamber, the sampling channel and the junction are sized and configured such that a first portion of blood flows into the sequestration chamber toward the air permeable blood barrier for sequestration therein, and a second portion of blood bypasses the sequestration chamber and the first portion of blood sequestered therein and is directed into the sampling channel toward the outlet port.

In another aspect, the sampling channel and the junction is sized and configured such that a first portion of blood flows into and fills the sequestration chamber to displace air therein through the vent, and such that a second portion of blood bypasses the sequestration chamber and the first portion of blood sequestered therein and is directed into the sampling channel toward the outlet port.

The blood sequestration and sampling system sequestration device, in certain aspects can include a blood sampling pathway having a patient needle on a proximal end and a sample collection device on a distal end; and a blood sequestration device attached on the blood sampling pathway between the proximal end and distal end of the blood sampling pathway. The blood sequestration device in one aspect can include an inlet port coupled with the blood sampling pathway toward the patient needle, an outlet port coupled with the blood sampling pathway toward the sample collection device, a sequestration chamber connected with the inlet port via a junction, which chamber has a vent that includes an air permeable blood barrier, the vent being defined by an outer wall that at least partially circumscribes the air permeable blood barrier and includes one or more air vents, the vent further including a cap that at least partially covers the wall and a one-way seal abutting the air permeable blood barrier that inhibits air from entering the sequestration chamber; and a sampling channel having a proximal end connected with the inlet port via the junction, and a distal end connected with the outlet port. In a certain related aspect, the sequestration chamber, the sampling channel and the junction can be sized and configured such that a first portion of blood flows into the sequestration chamber toward the air permeable blood barrier for sequestration therein, and a second portion of blood bypasses the sequestration chamber and the first portion of blood sequestered therein and is directed into the sampling channel toward the outlet port.

The blood sequestration device is connected along the blood sampling pathway between the patient needle and the sample needle, and includes an inlet port for receiving the sample of blood. The blood sequestration device further includes a sequestration chamber connected with the inlet port for receiving a first amount of the sample of blood, the sequestration chamber having a vent comprising an air permeable blood barrier for sequestering at least a first portion of the first amount of the sample of blood. The blood sequestration device may further include a sampling channel having a proximal end connected with the inlet port, the sampling channel conveying a subsequent amount of the sample of blood to the evacuated blood collection container upon the sequestration chamber sequestering at least the first portion of the first amount of the sample of blood. The blood sequestration device further includes an outlet port connected with a distal end of the sampling channel, the outlet port for outputting the subsequent amount of the sample of blood.

The details of one or more embodiments are set forth in the accompanying drawings and the description below.

Other features and advantages will be apparent from the description and drawings, and from the claims.

BRIEF DESCRIPTION OF THE DRAWINGS

These and other aspects will now be described in detail with reference to the following drawings.

FIGS. 16A-16D illustrate a blood sequestration device in accordance with yet another implementation.

FIGS. 23A-23E illustrate another implementation of a blood sequestration device that uses a vacuum force from a blood collection device.

FIGS. 24A-24D illustrate another implementation of a blood optimization system and blood sequestration device.

FIGS. 25A-25D illustrate another implementation of a blood optimization system and blood sequestration device.

FIGS. 26A-26E illustrate another implementation of a blood optimization system and blood sequestration device.

FIGS. 27A-27D illustrate another implementation of a blood optimization system and blood sequestration device.

FIGS. 28A-28F illustrate another implementation of a blood optimization system and blood sequestration device.

FIGS. 29A-29C illustrate another implementation of a blood optimization system and blood sequestration device.

FIGS. 30A-30G illustrate another implementation of a blood optimization system and blood sequestration device.

Like reference symbols in the various drawings indicate like elements.

DETAILED DESCRIPTION

This document describes blood sample optimization systems and methods for reducing or eliminating contaminates in collected blood samples, which in turn reduces or eliminates false positive readings in blood cultures or other testing of collected blood samples. In some implementations, a blood sample optimization system includes a patient needle for vascular access to a patient's bloodstream, a sample needle for providing a blood sample to a blood collection container, such as an evacuated blood collection container or tube like a Vacutainer™ or the like, or other sampling device, and a blood sequestration device located between the patient needle and the sample needle. The blood sequestration device includes a sequestration chamber for sequestering an initial, potentially contaminated aliquot of blood, and may further include a sampling channel that bypasses the sequestration chamber to convey likely uncontaminated blood between the patient needle and the sample needle after the initial aliquot of blood is sequestered in the sequestration chamber.

Figure 1:
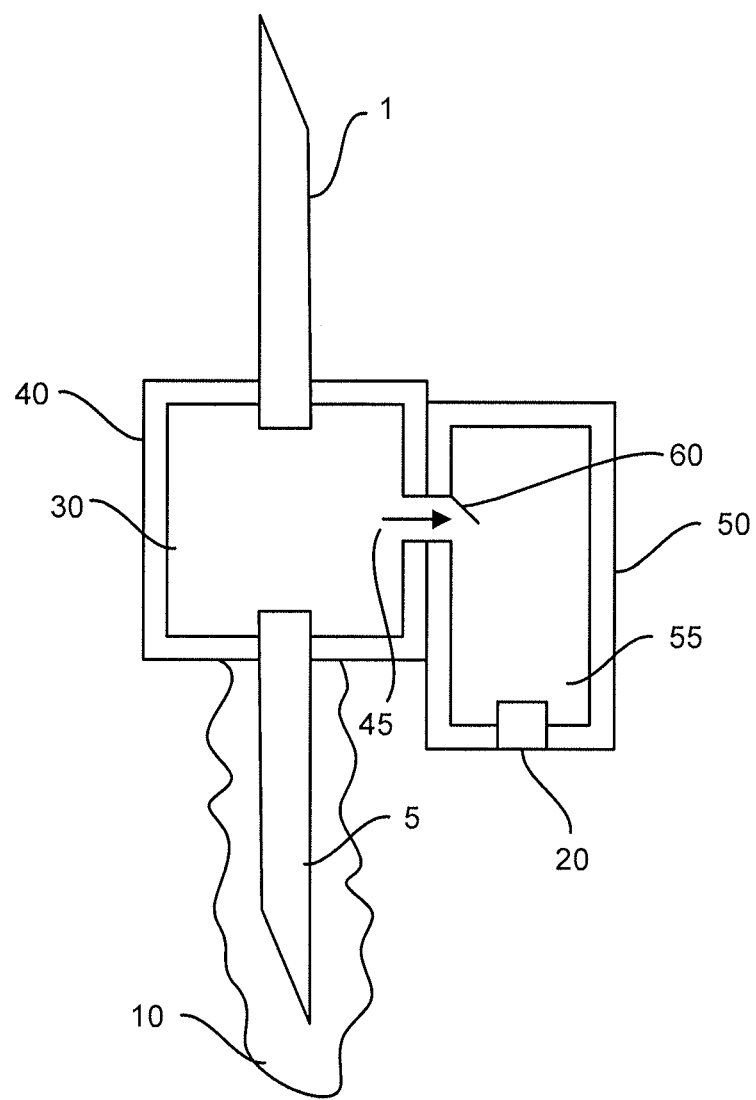
FIG. 1 illustrates a blood sample optimization system.

FIG. 1 illustrates a blood sample optimization system in accordance with some implementations. The system includes a patient needle 1 to puncture the skin of a patient to access the patient's vein and blood therein. The system further includes a sample needle (i.e., a resealably closed needle for use with Vacutainers™ or the like) 5, which may be contained within and initially sealed by a resealable boot 10, a Luer activated valve, or another collection interface or device. The resealable boot 10 can be pushed aside or around the sample needle 5 by application of a Vacutainer™ bottle (not shown) for drawing the patient's blood. The system can further include a low volume chamber 30 that leads to the sample needle 5, but also includes an orifice or one or more channels 45 that lead to a sequestration chamber 55 formed by a housing 50.

The sequestration chamber 55 is a chamber, channel, pathway, lock, or other structure for receiving and holding a first aliquot of the patient's blood, which may be in a predetermined or measured amount, depending on a volume of the sequestration chamber 55. The first draw of blood typically contains or is more susceptible to containing organisms that cause bacteraemia and sepsis or other pathogens than subsequent blood draws. The sequestration chamber 55 can be a vessel encased in a solid housing, formed in or defined by the housing itself, or can be implemented as tubing or a lumen. The sequestration chamber 55, regardless how formed and implemented, may have a predetermined volume. In some implementations, the predetermined volume may be based on a volume of the patient needle, i.e. ranging from less than the volume of the patient needle to any volume up to or greater than 20 times or more of the volume of the patient needle. The predetermined volume of the sequestration chamber 55 may also be established to economize or minimize an amount of blood to be sequestered and disposed of.

The sequestration chamber 55 can be formed, contained or housed in a chamber housing 50, and can be made of plastic, rubber, steel, aluminum or other suitable material. For example, the sequestration chamber 55 could be formed of flexible tubing or other elastomeric materials. The sequestration chamber 55 further includes an air permeable blood barrier 20 that allows air to exit the sequestration chamber 55. As used herein the term "air permeable blood barrier" means an air permeable but substantially blood impermeable substance, material, or structure. Examples may include hydrophobic membranes and coatings, a hydrophilic membrane or coating combined with a hydrophobic membrane or coating, mesh, a filter, a mechanical valve, antimicrobial material, or any other means of allowing air to be displaced from the sequestration chamber 55 as it is filled with blood. In various exemplary embodiments, an air permeable blood barrier may be formed by one or more materials that allow air to pass through until contacted by a liquid, such material then becomes completely or partially sealed to prevent or inhibit the passage of air and/or liquid. In other words, prior to contact with liquid, the material forms a barrier that is air permeable. After contact with a liquid, the material substantially or completely prevents the further passage of air and/or liquid.

The orifice or channel 45 can be any desired length, cross-sectional shape or size, and/or can be formed to depart from the low volume chamber 30 at any desired angle or orientation. The orifice or channel 45 may also include a one-way flap or valve 60 that maintains an initial aliquot of blood sample within the sequestration chamber 55. In some specific implementations, the orifice or channel 45 can include a "duck bill" or flapper valve 60, or the like, for one-way flow of blood from low volume chamber 30 to the sequestration chamber 55. The air permeable blood barrier 20 can also be constructed of a material that allows air to exit but then seals upon contact with blood, thereby not allowing external air to enter sequestration chamber 55. This sealing would eliminate the need for a valve.

Valve 60 can be any type of valve or closing mechanism. Chamber 30 is designed to hold virtually no residual blood, and can be designed to be adapted to hold or allow pass-through of a particular volume or rate of blood into sequestration chamber 55. Likewise, sequestration chamber 55 may also include any type of coating, such as an antimicrobial coating, or a coating that aids identification and/or diagnosis of components of the first, sequestered blood draw.

Housing 50 and 40 can be formed of any suitable material, including plastic, such as acrylonitrile butadiene styrene (ABS) or other thermoplastic or polymeric material, rubber, steel, or aluminum. The air permeable blood barrier 20 can include a color-providing substance, or other signaling mechanism, that is activated upon contact with blood from the initial blood draw, or when air displacement is stopped, or any combination of events with blood in the sequestration chamber 55. The air permeable barrier may also include an outer layer such as a hydrophobic membrane or cover that inhibits or prevents the inadvertent or premature sealing of the filter by an external fluid source, splash etc. Sequestration chamber 55 can also be translucent or clear to enable a user to visually confirm the chamber is filled.

Figure 2:
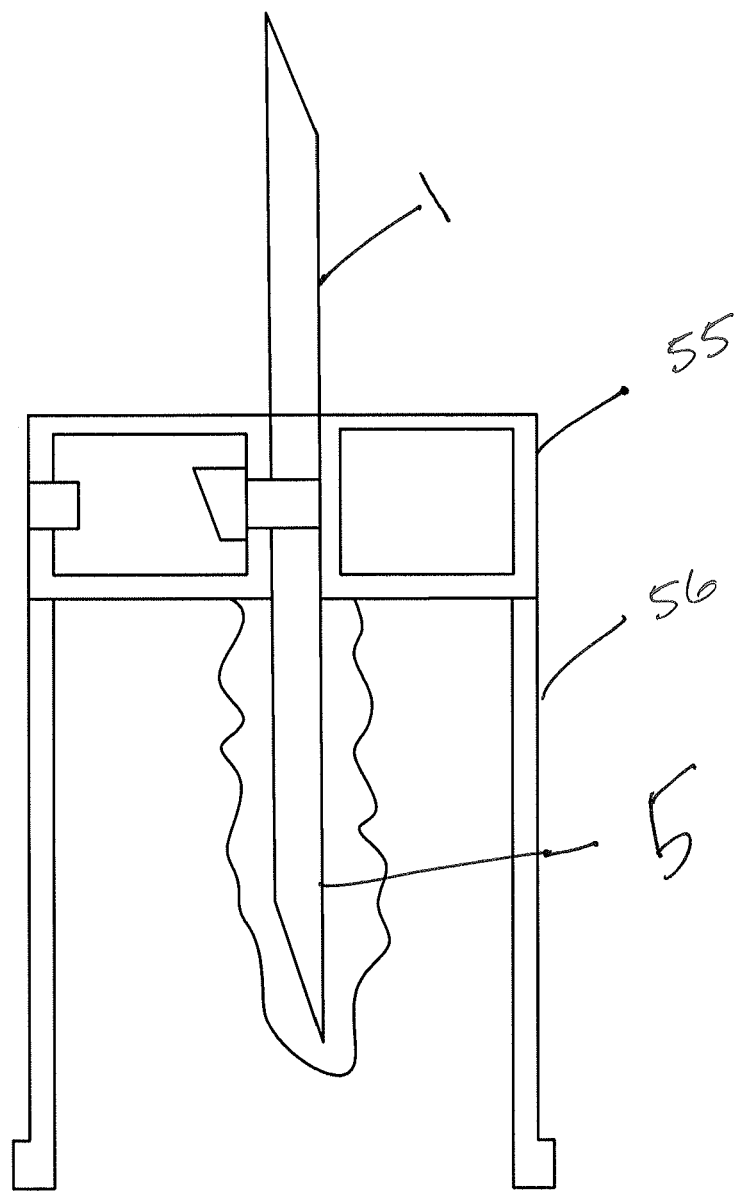
FIG. 2 illustrates a blood sample optimization system in accordance with an alternative implementation.

FIG. 2 illustrates a blood sample optimization system in accordance with some alternative implementations. In the implementation shown in FIG. 2, a sequestration chamber 55, or waste chamber, surrounds the patient needle 1, with an open-ended cuff or housing connected with the waste chamber and encircling the sample needle housing base and housing. The patient needle 1 and sample needle 5 are connected together by a boot 56, which forms a continuous blood draw channel therethrough. The boot 56 includes a single orifice or channel leading from the blood draw channel into sequestration chamber 55. The device can include more than one single orifice or channel, in other implementations. Each orifice or channel can include a one-way valve, and can be sized and adapted for predetermined amount of blood flow.

The sequestration chamber 55 includes an air permeable blood barrier. The filter can further include a sensor or indicator to sense and/or indicate, respectively, when a predetermined volume of blood has been collected in the sequestration chamber 55. That indication will alert a user to attach an evacuated blood collection tube or bottle, such as a Vacutainer™ to the sample needle 5. The housing for the sequestration chamber 55 can be any size or shape, and can include any type of material to define an interior space or volume therein. The interior space is initially filled only with air, but can also be coated with an agent or substance, such as a decontaminate, solidifying agent, or the like. Once evacuated blood collection tube is attached to the sample needle 5, blood will flow automatically into the patient needle 1, through the blood draw channel and sample needle 5, and into the bottle. The sample needle 5 is covered by a resealable boot, coating or membrane that seals the sample needle when a blood collection bottle is not attached thereon or thereto.

Figure 3:
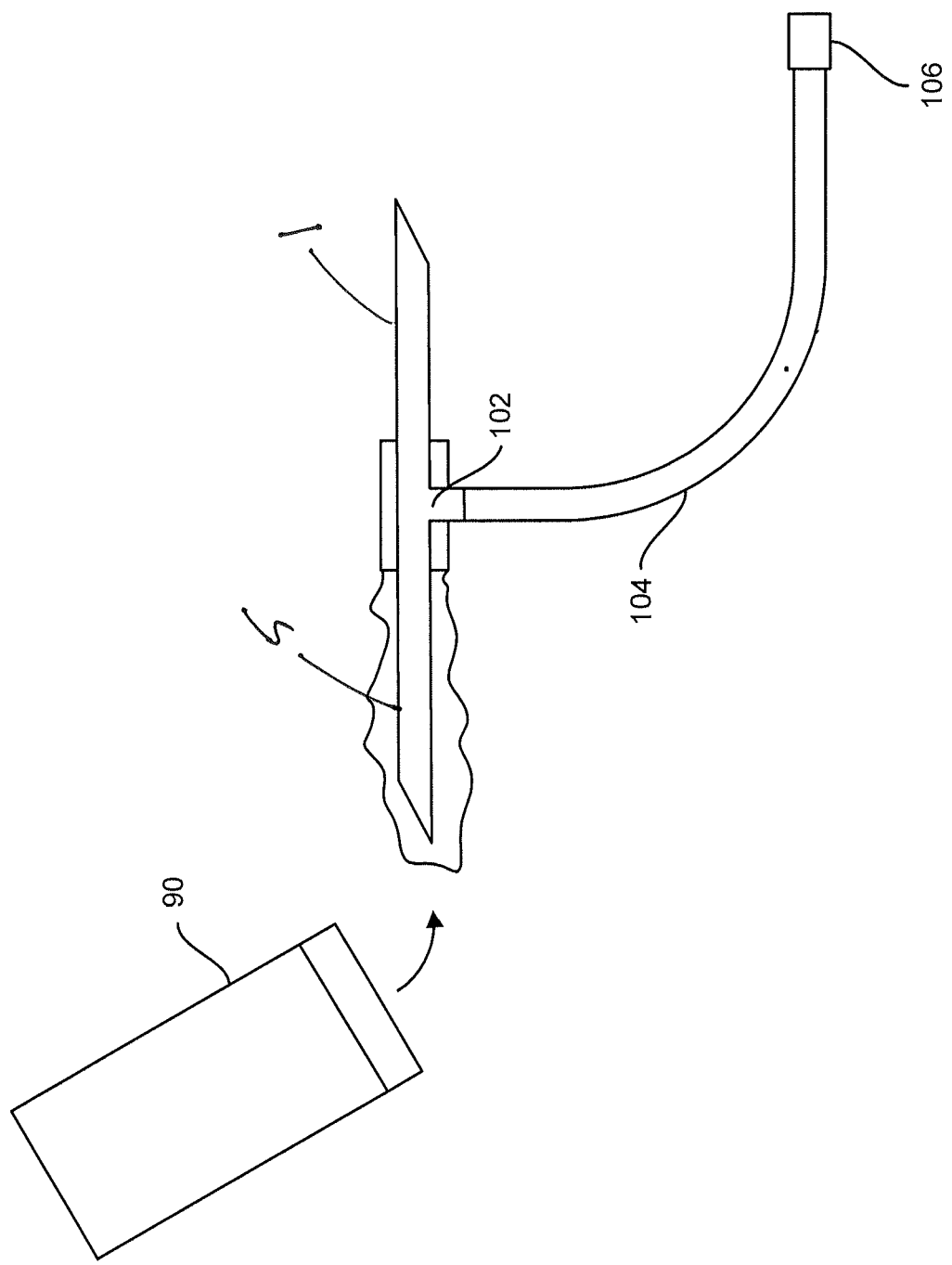
FIG. 3 illustrates a blood sample optimization system in accordance with another alternative implementation.

FIG. 3 illustrates a blood sample optimization system in accordance with some alternative implementations. In the implementation shown, a sample needle 5 is surrounded by a resealable boot or membrane, and is further connected with a patient needle 1. A blood flow channel is formed through the sample needle and the patient needle. The connection between the sample needle and patient needle includes a "T" or "Y" connector 102, which includes a channel, port or aperture leading out from the main blood flow channel to a sequestration chamber 104.

The T or Y connector 102 may include a flap or one-way valve, and have an opening that is sized and adapted for a predetermined rate of flow of blood. The sequestration chamber 104 can be formed from tubing, or be formed by a solid housing, and is initially filled with air. The sequestration chamber 104 will receive blood that flows out of a patient automatically, i.e. under pressure from the patient's own blood pressure. The sequestration chamber 104 includes an air permeable blood barrier 106, preferably at the distal end of tubing that forms the sequestration chamber 104, and which is connected at the proximal end to the T or Y connector 102. The T or Y connector 102 can branch off at any desired angle for most efficient blood flow, and can be formed so as to minimize an interface between the aperture and channel and the main blood flow channel, so as to minimize or eliminate mixing of the initial aliquot of blood with main blood draw samples.

Figure 4:
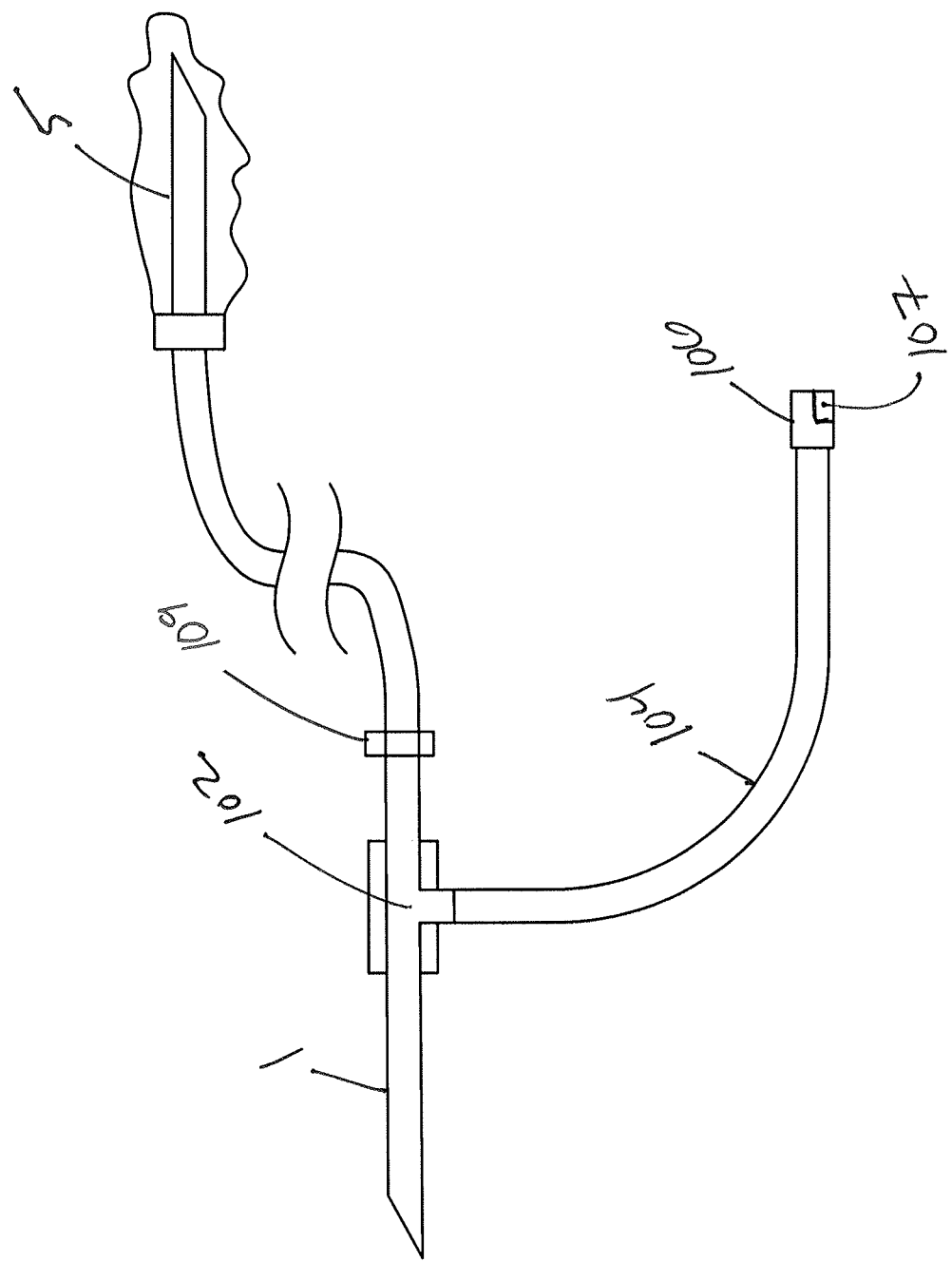
FIG. 4 illustrates a blood sample optimization system in accordance with another alternative implementation.

In some alternative implementations, the sample needle may be affixed to a tubing of any length, as shown in FIG. 4, connecting at its opposite end to the T or Y connector 102. The sequestration chamber 104 can be any shape or volume so long as it will contain a predetermined amount of blood sample in the initial aliquot. The T or Y connector 102 may also include an opening or channel that is parallel to the main blood flow channel. The air permeable blood barrier may further include an indicator 107 or other mechanism to indicate when a predetermined amount of blood has been collected in the sequestration chamber, or when air being expelled reaches a certain threshold, i.e. to zero. The tubing can also include a clip 109 that can be used to pinch off and prevent fluid flow therethrough.

Once the air permeable blood barrier and primary chamber are sealed the initial aliquot of blood is trapped in the sequestration chamber 104, an evacuated blood collection tube, such as a Vacutainer™ bottle may be attached to the sample needle 5 to obtain the sample. The blood collection tube can be removed, and the sample needle 5 will be resealed. Any number of follow-on blood collection tubes can then be attached for further blood draws or samples. Upon completion of all blood draws, the system can be discarded, with the initial aliquot of blood remaining trapped in the sequestration chamber 104.

Figure 5:
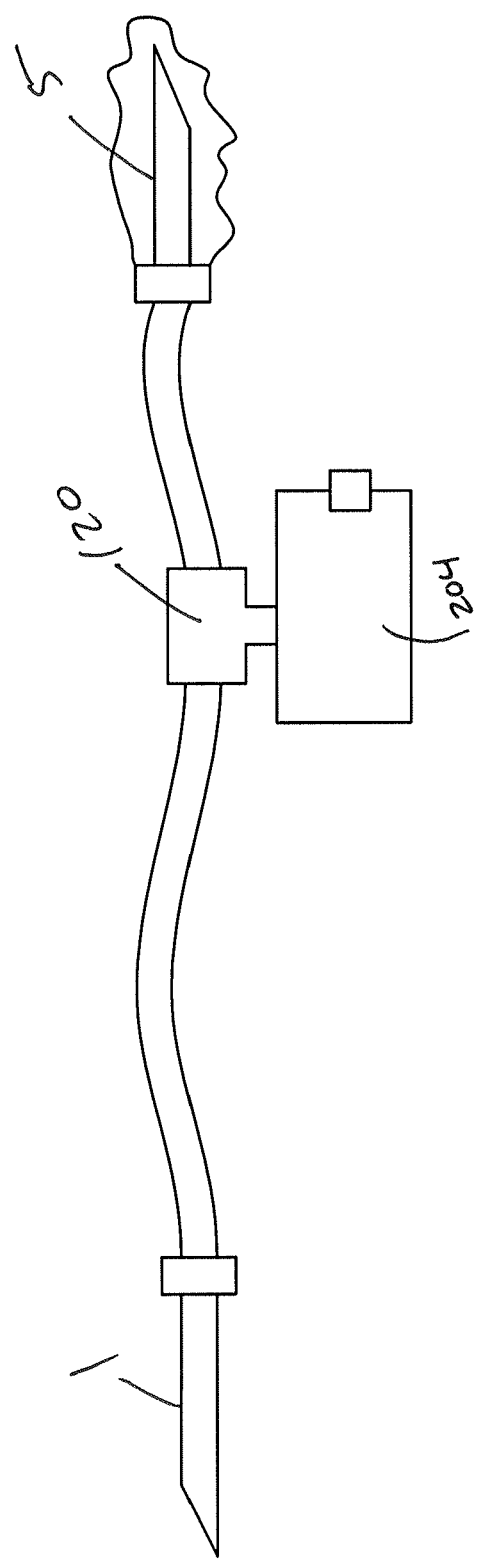
FIG. 5 illustrates a blood sample optimization system in accordance with another alternative implementation.

FIG. 5 illustrates a blood sample optimization system in accordance with some alternative implementations. In the implementation shown, a sample needle 5 is connected with a patient needle by tubing. A "T" or "Y" connector 120 is added along the tubing at any desired location, and includes an aperture, port or channel leading to a sequestration chamber 204, substantially as described above.

Figure 6:
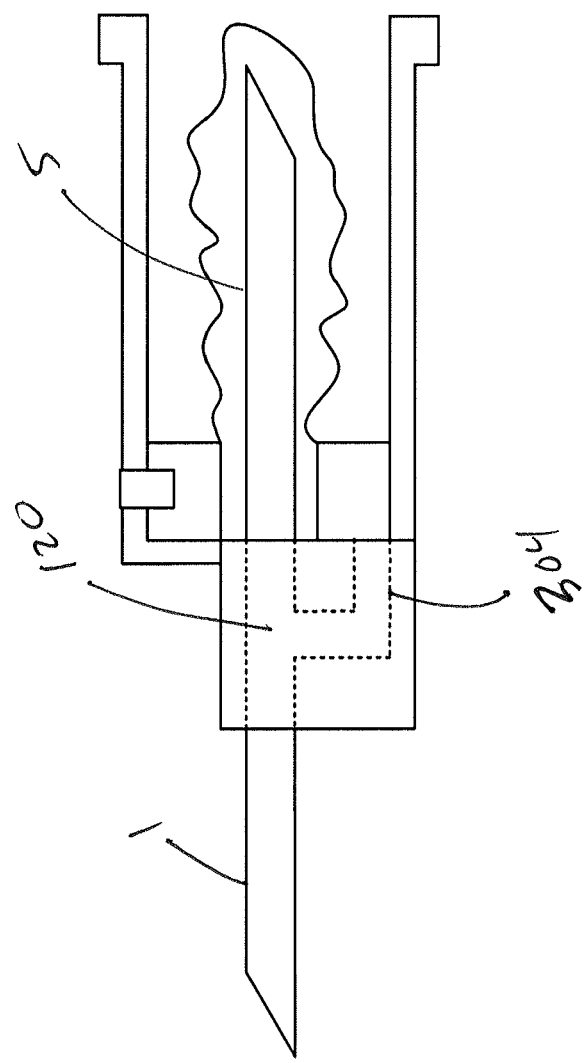
FIG. 6 illustrates a blood sample optimization system in accordance with an alternative implementation.

FIG. 6 illustrates a blood sample optimization system in accordance with some alternative implementations, in which a sequestration chamber 304, formed as a primary collection channel, receives an initial aliquot of blood, and is provided adjacent to the blood sampling channel. The sequestration chamber 304 can encircle the blood sampling channel, the patient needle 1, and/or the sample needle 5. The primary collection channel can include a T or Y connector 120, or other type of aperture or channel. The sequestration chamber 304 includes an air permeable blood barrier, which can also include an indicator of being contacted by a fluid such as blood, as described above.

In some implementations, either the patient needle 1 or the sample needle 5, or both, can be replaced by a Luer lock male or female connector. However, in various implementations, the connector at a sample needle end of the blood sample optimization system is initially sealed to permit the diversion of the initial aliquot of blood to the sequestration chamber, which is pressured at ambient air pressure and includes the air outlet of the air permeable blood barrier. In this way, the system passively and automatically uses a patient's own blood pressure to overcome the ambient air pressure of the sequestration chamber to push out air through the air permeable blood barrier and displace air in the sequestration chamber with blood.

Figure 7:
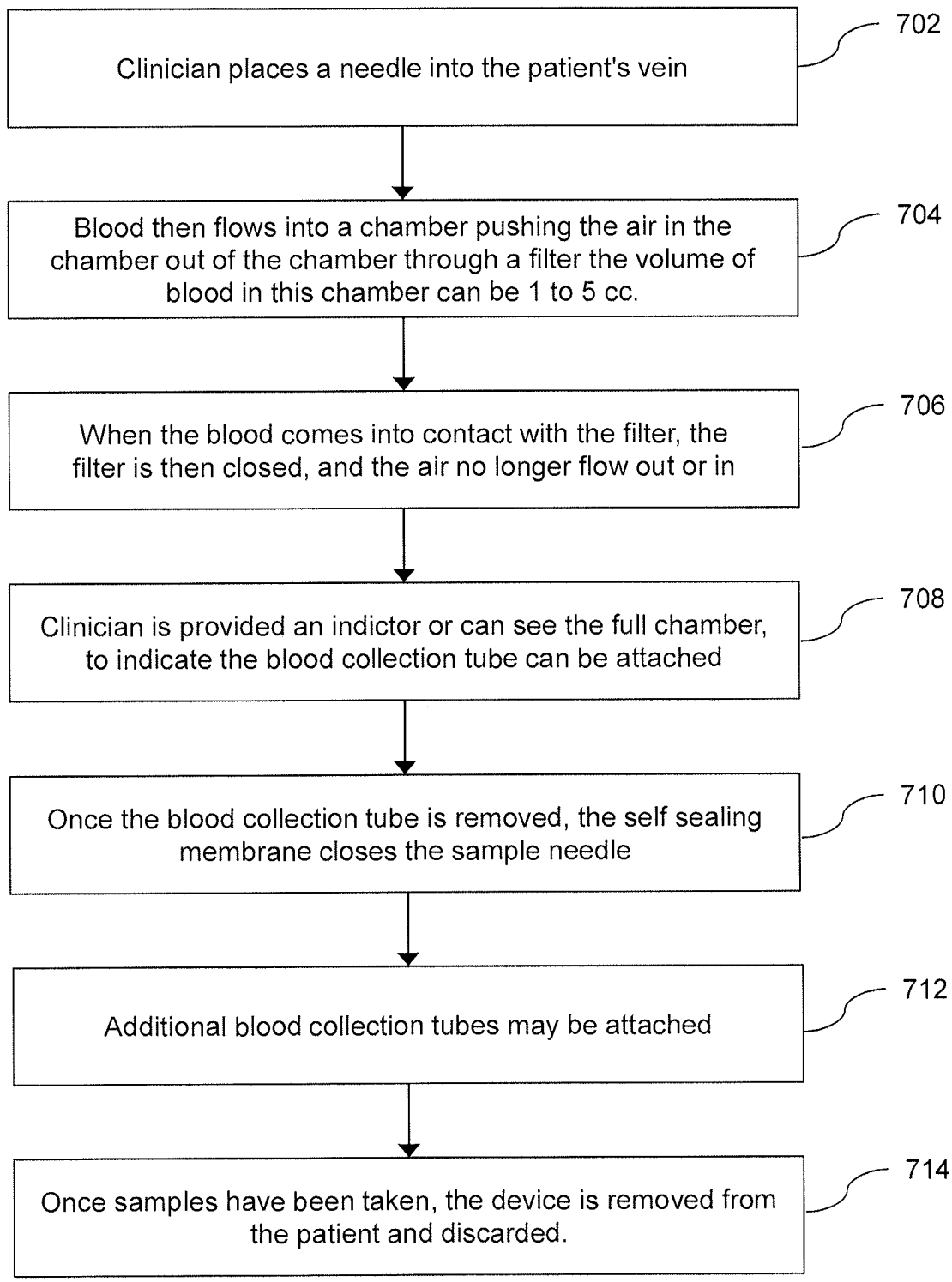
FIG. 7 is a flowchart of a method for optimizing a quality of a blood culture.

FIG. 7 is a flowchart of an exemplary method for optimizing the quality of a blood culture. At 702, a clinician places a needle into a patient's vein. At 704, blood then flows into a sequestration chamber, pushing the air in the sequestration chamber out of the sequestration chamber through an air permeable blood barrier. In some implementations, the volume of the sequestration chamber is less than 0.1 to more than 5 cubic centimeters (cc's), or more. The sequestration chamber is sized and adapted to collect a first portion of a blood sample, which is more prone to contamination than secondary and other subsequent portion of the blood sample or subsequent draws. Since the sequestration chamber has an air-permeable blood barrier through which air can be displaced by blood pushed from the patient's vein, such blood will naturally and automatically flow into the sequestration chamber before it is drawn into or otherwise enters into a Vacutainer or other bottle for receiving and storing a blood sample.

When the sequestration chamber fills, the blood will gather at or otherwise make contact with the air permeable blood barrier, which will inhibit or prevent blood from passing therethrough. At 706, when the blood comes into contact with the entire internal surface area of the air permeable blood barrier, the air permeable blood barrier is then closed and air no longer flows out or in. At 708, the clinician may be provided an indictor or can see the full chamber, to indicate the evacuated blood collection tube, such as a Vacutainer™ can be attached. The indicator can include visibility into the primary chamber to see whether it is full, the blood barrier changing color, for example, or other indicator. The fill time of the sequestration chamber may be substantially instantaneous, so such indicator, if present, may be only that the sequestration chamber is filled.

Prior to an evacuated blood collection tube being attached, communication between the needle, sampling channel, and the sequestration chamber is restricted by the sealing of the sequestration chamber blood barrier thereby not permitting air to reenter the system through the sequestration. Sealing the communication path could also be accomplished with a mechanical twist or other movement, a small orifice or tortuous pathway, eliminating the need for a separate valve or mechanical movement or operation by the clinician. At 710, once the evacuated blood collection tube is removed, the self-sealing membrane closes the sample needle, and at 712, additional subsequent evacuated blood collection tubes may be attached. Once samples have been taken, at 714 the device is removed from the patient and discarded.

FIGS. 8A-8E illustrate an exemplary blood sample optimization system 800 for non-contaminated blood sampling, in accordance with some implementations. The blood sample optimization system 800 includes an inlet port 802 that can be connected to tubing, a patient needle (or both), or other vascular or venous access device, and a pathway splitter 804 having a first outlet to a sequestration chamber tubing 806 and a second outlet to sample collection tubing 808. One or both of the sequestration chamber tubing 806 and the sample collection tubing 808 can be formed of tubing. In some implementations, the sequestration chamber tubing 806 is sized so as to contain a particular volume of initial blood sample. The sample collection tubing 808 will receive a blood sample once the sequestration chamber tubing 806 is filled. The sample collection tubing 808 can be connected to a Vacutainer™ base or housing 810, or other blood sample collection device.

Figure 8A:
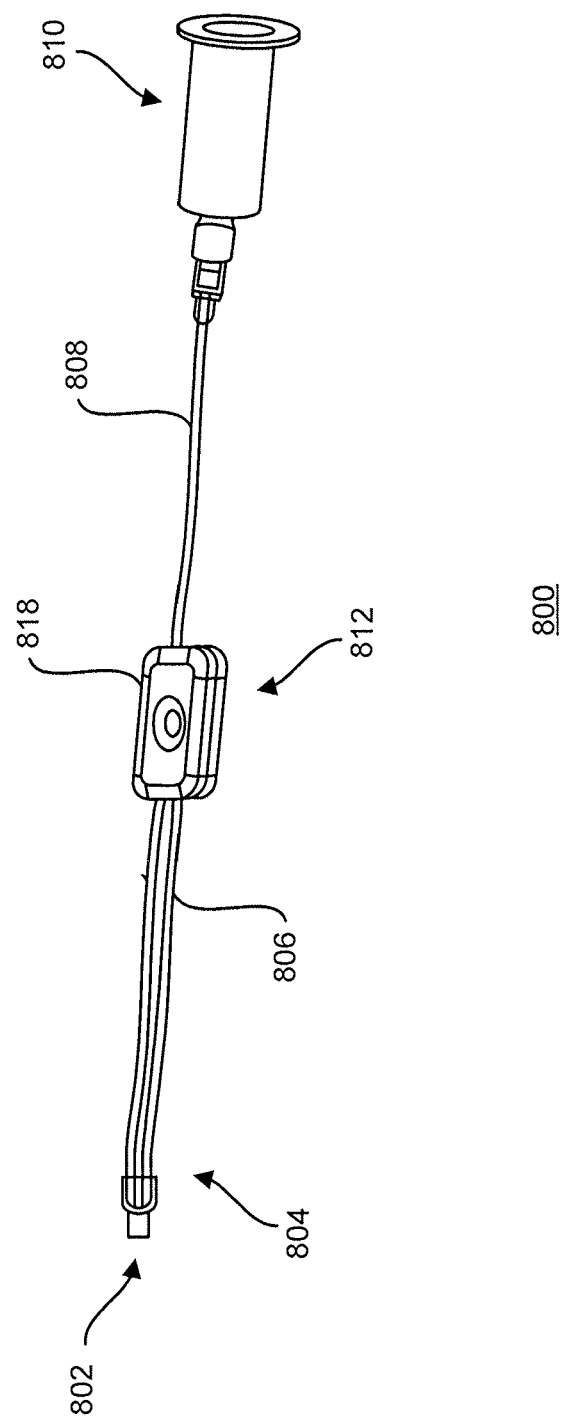
FIGS. 8A-8E illustrate a blood sequestration system for non-contaminated blood sampling, in accordance with some implementations.
Figure 8B:
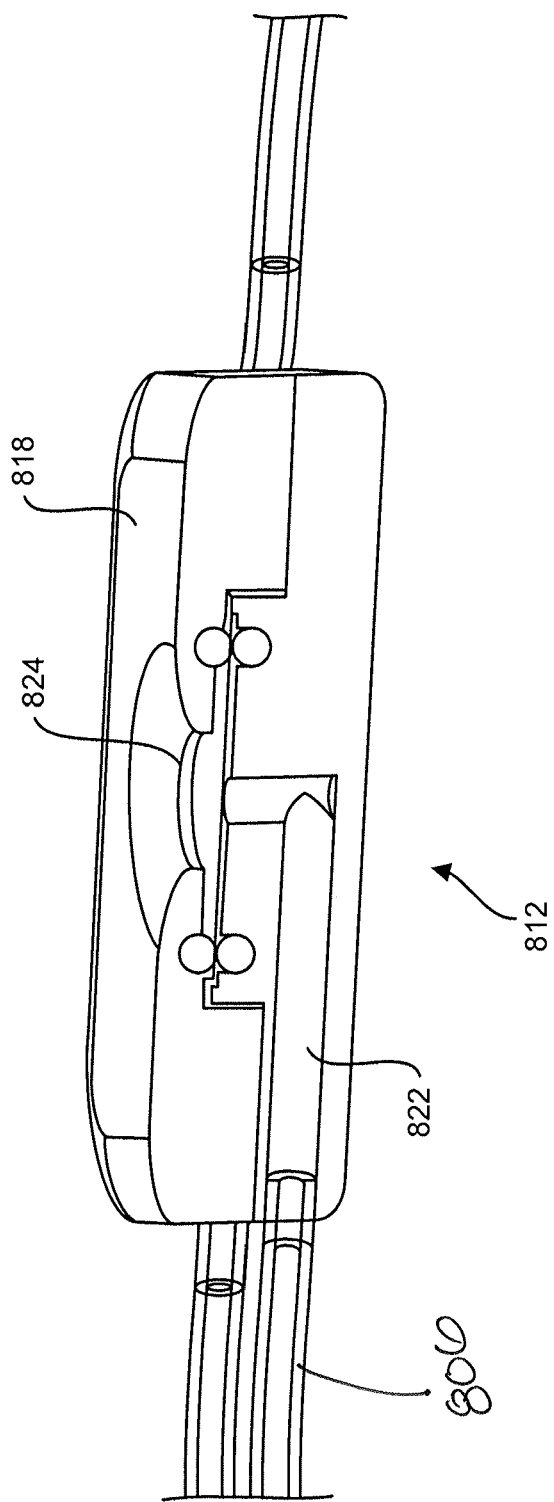
Figure 8C:
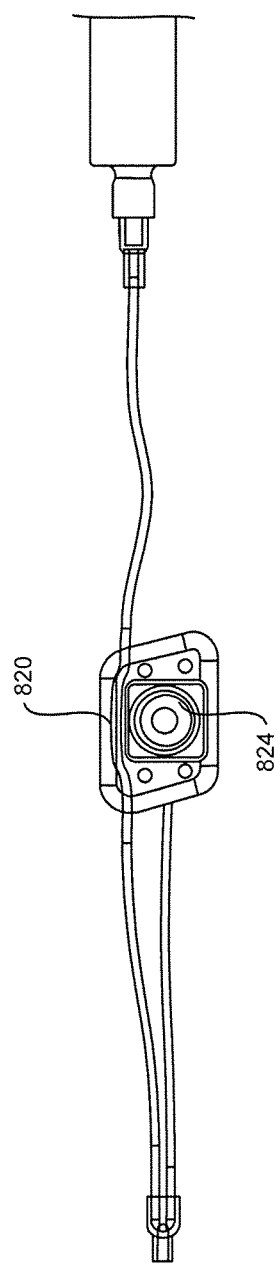
Figure 8D:
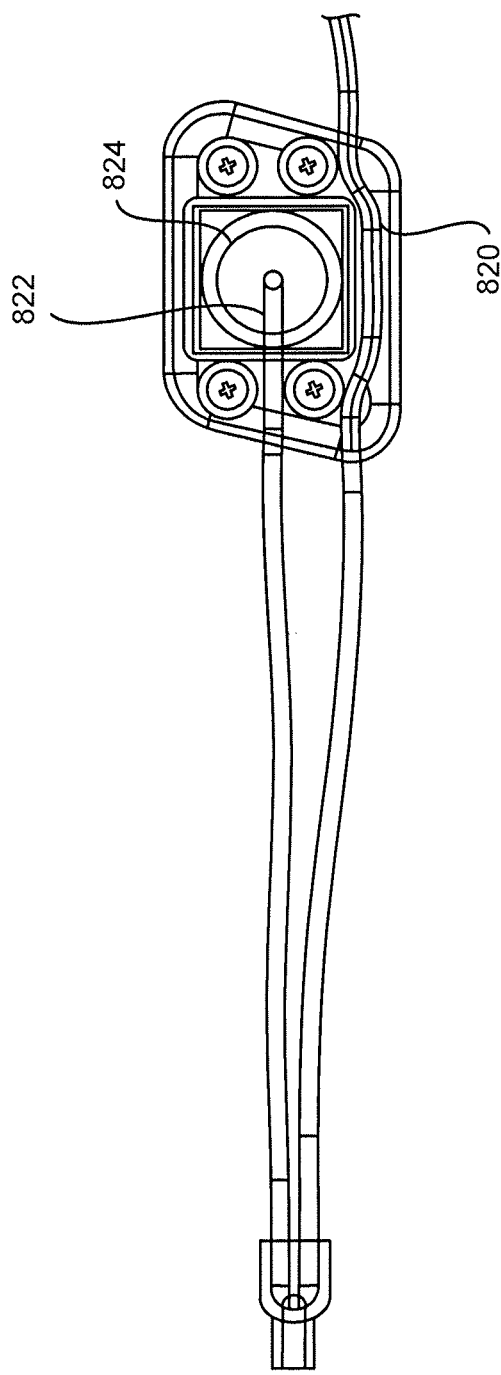
Figure 8E:
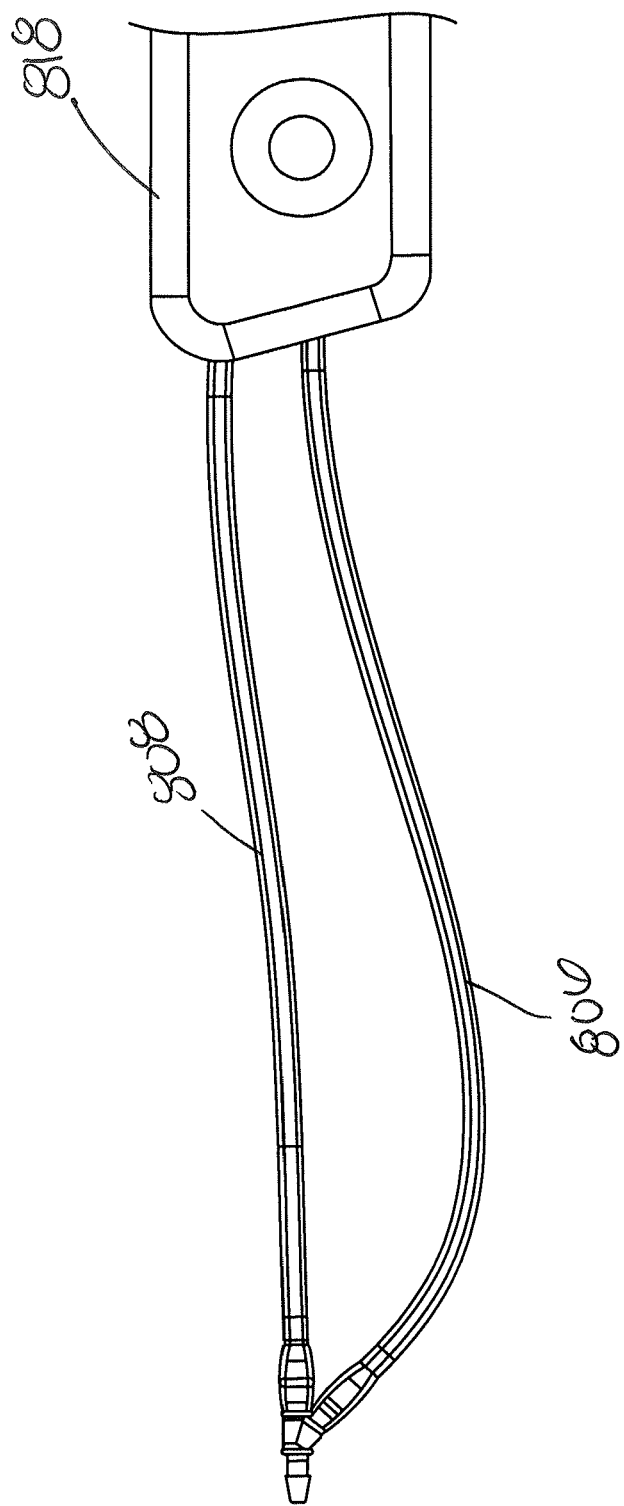

The blood sequestration system 800 further includes a blood sequestration device 812 which, as shown in more detail in FIGS. 8B-8D, includes a housing 818 that includes a sampling channel 820 defining a pathway for the non-contaminated sample collection tubing 808 or connected at either end to the non-contaminated sample collection tubing 808. The sampling channel 820 can be curved through the housing 818 so as to better affix and stabilize the housing 818 at a location along the non-contaminated sample collection tubing 808.

The blood sequestration device 812 further includes a sequestration chamber 822 connected with the sequestration chamber tubing 806 or other chamber. The sequestration chamber 822 terminates at an air permeable blood barrier 824. The air permeable blood barrier 824 can also include a coloring agent that turns a different color upon full contact with blood, as an indicator that the regular collection of blood samples (i.e. the non-contaminated blood samples) can be initiated. Other indicators may be used, such as a small light, a sound generation mechanism, or the like. In some implementations, the air permeable blood barrier is positioned at a right angle from the direction of sequestration chamber 822, but can be positioned at any distance or orientation in order to conserve space and materials used for the housing 818. The housing 818 and its contents can be formed of any rigid or semi-rigid material or set of materials.

Figure 9:
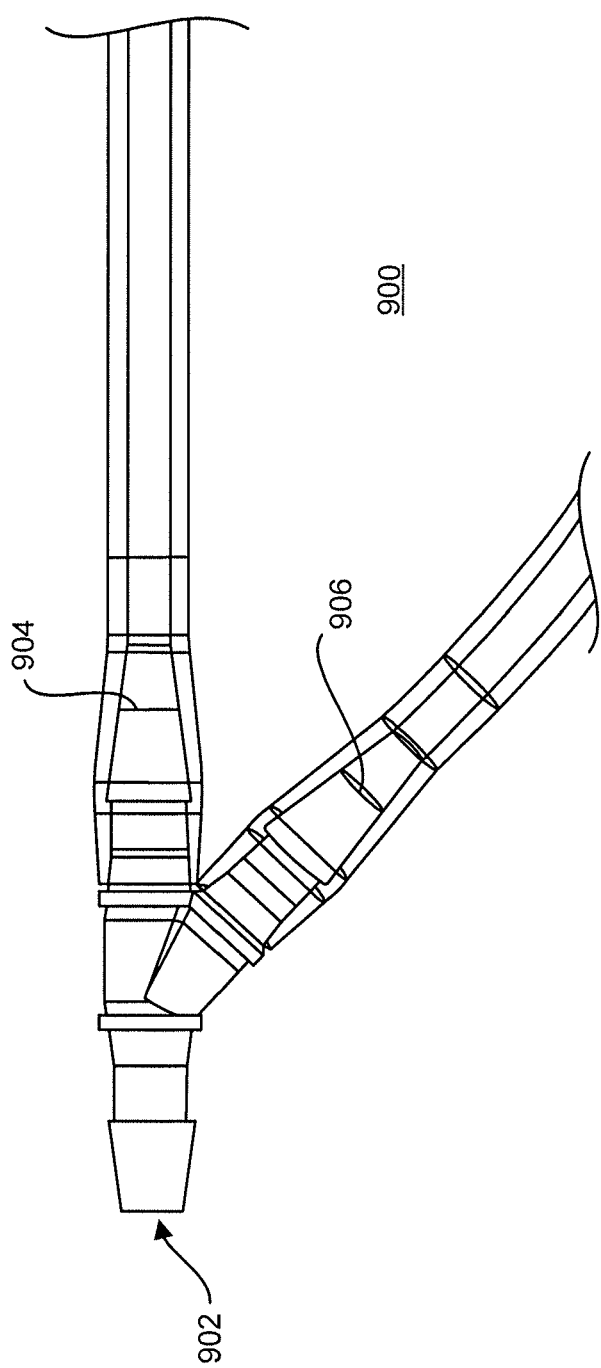
FIG. 9 illustrates a pathway splitter for use in a blood sequestrations system.
Figure 10A:
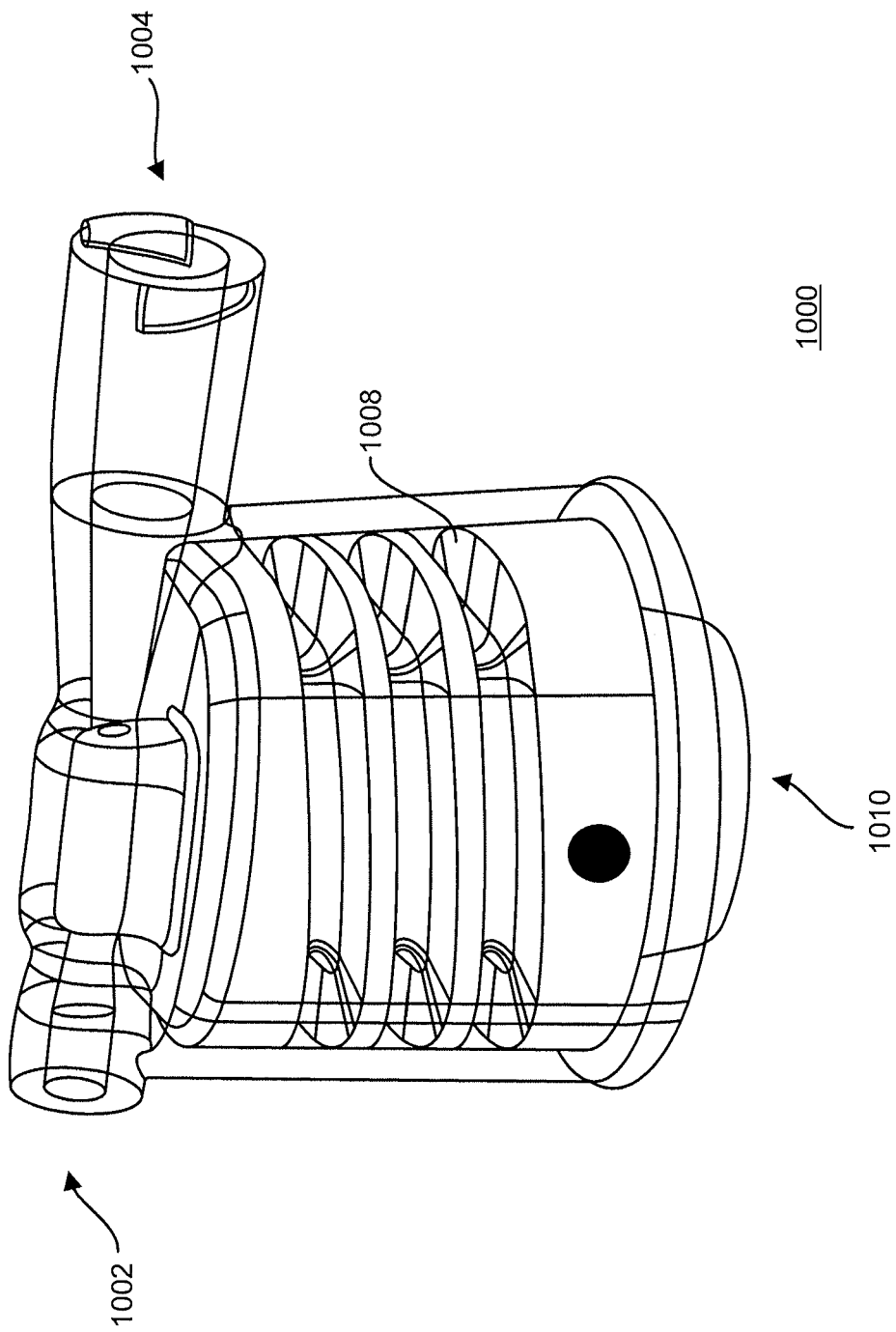
FIGS. 10A-10D illustrate a blood sequestration system for non-contaminated blood sampling, in accordance with alternative implementations.
Figure 10B:
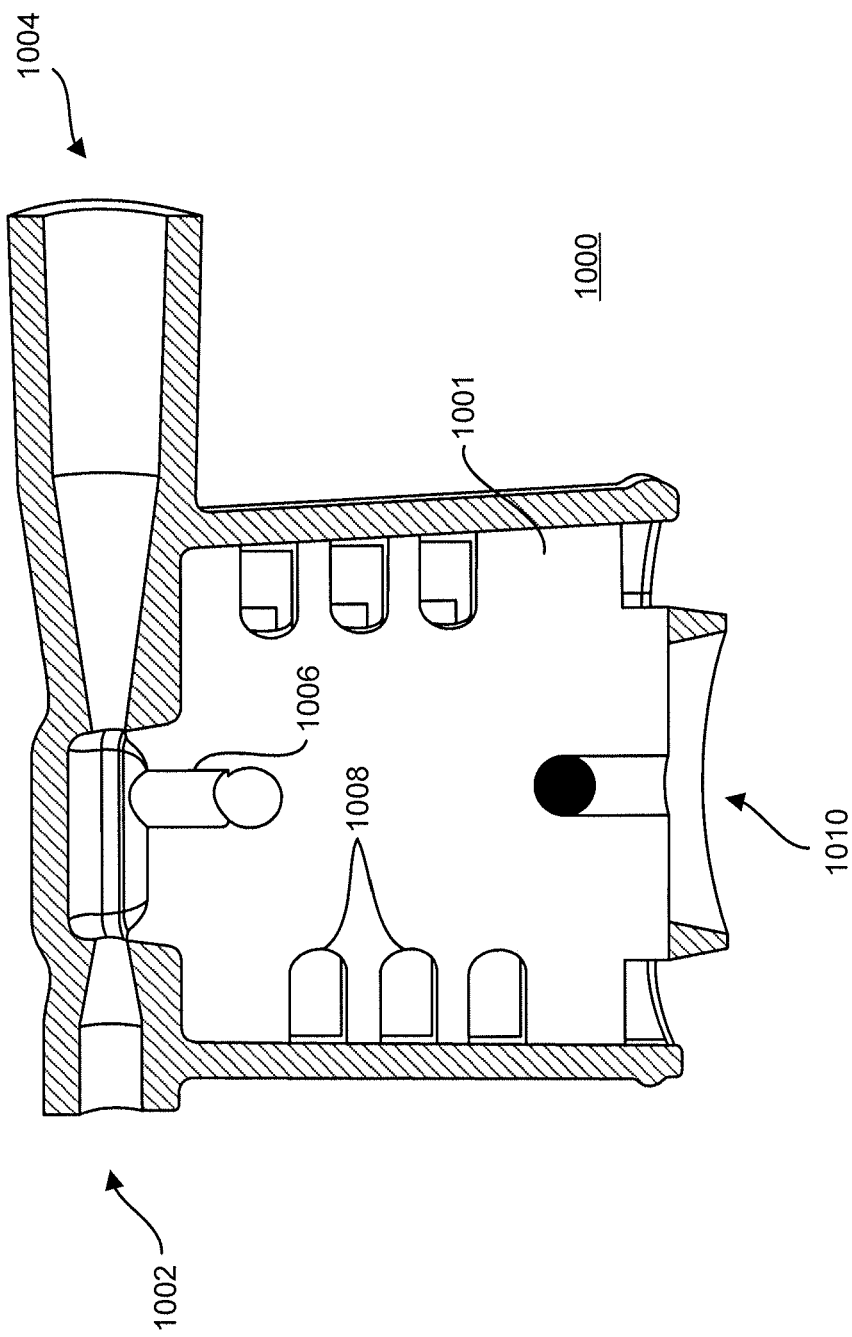
Figure 10C:
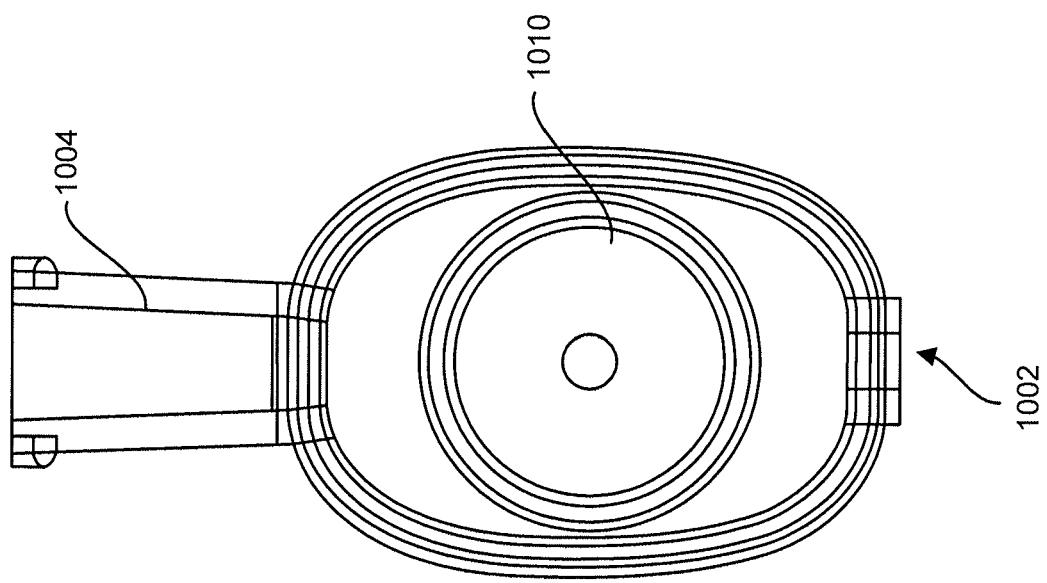
Figure 10D:
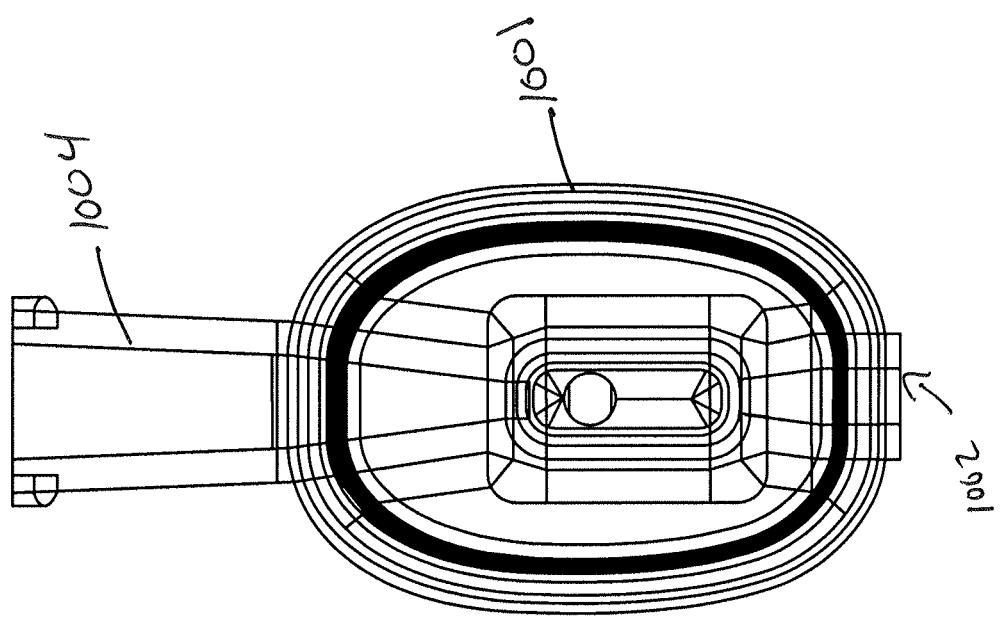
Figure 11A:
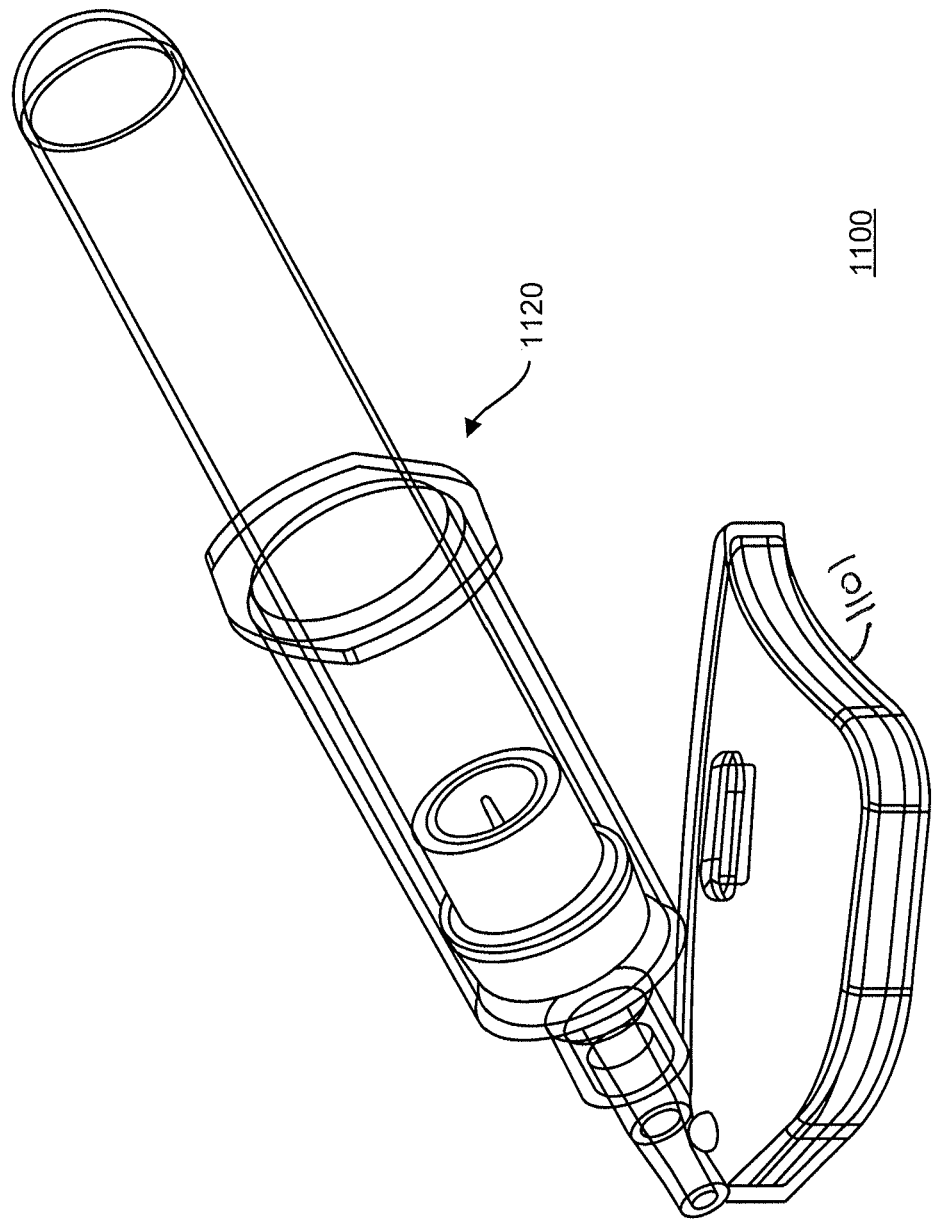
FIGS. 11A-11E illustrate a blood sequestration system for non-contaminated blood sampling, in accordance with other alternative implementations.
Figure 11B:
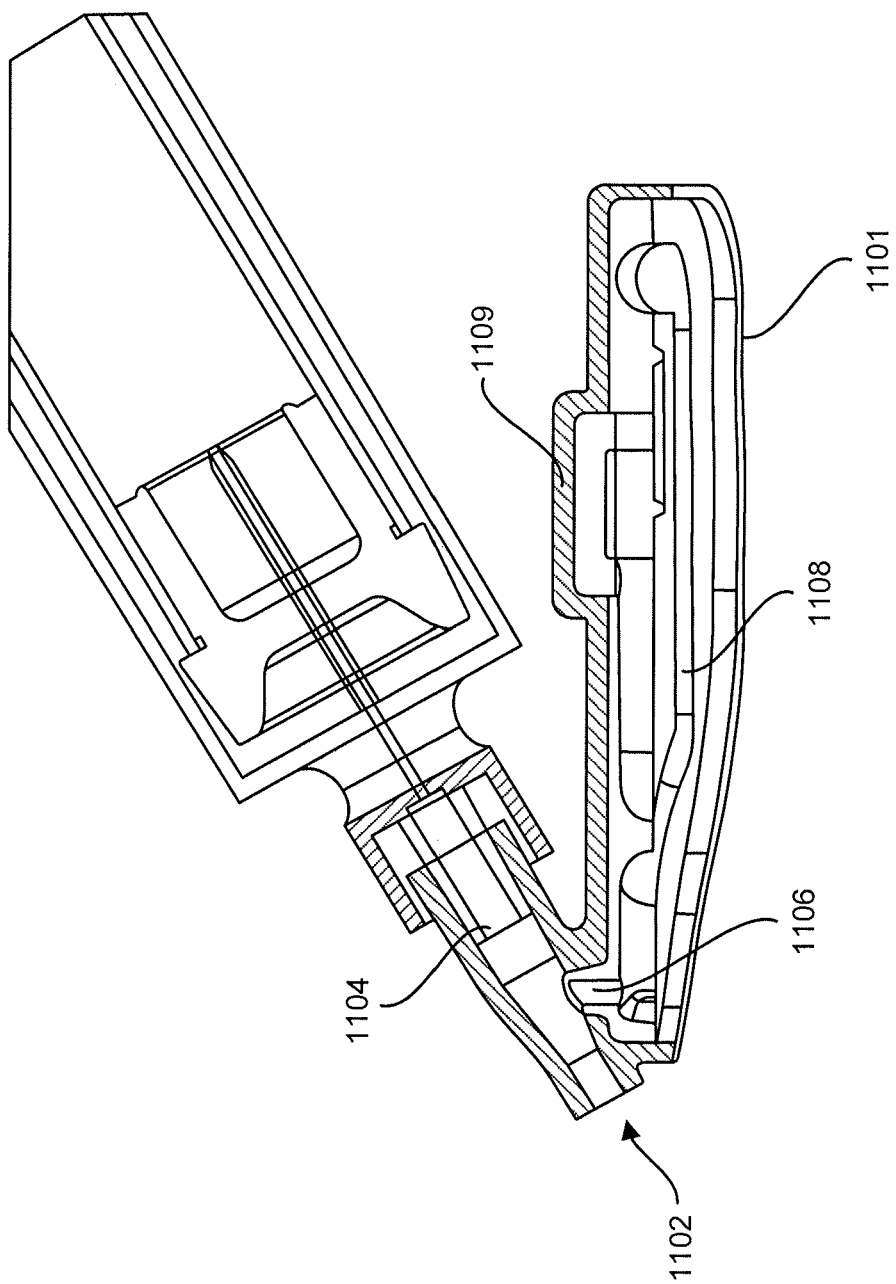
Figure 11C:
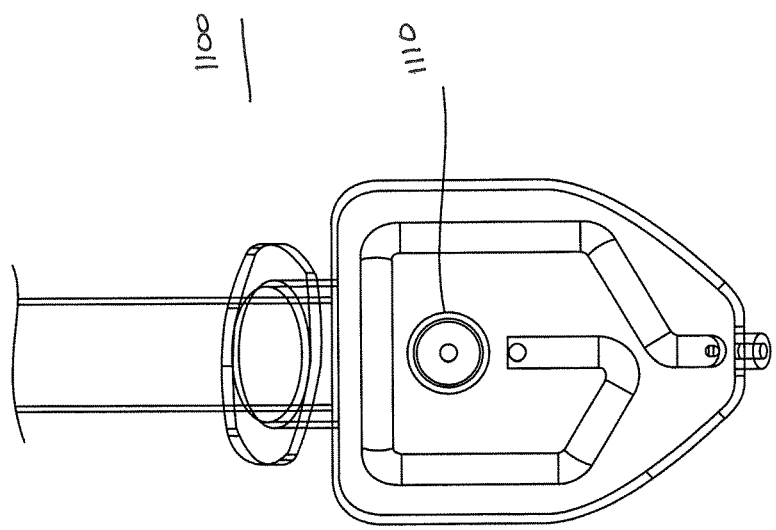
Figure 11D:
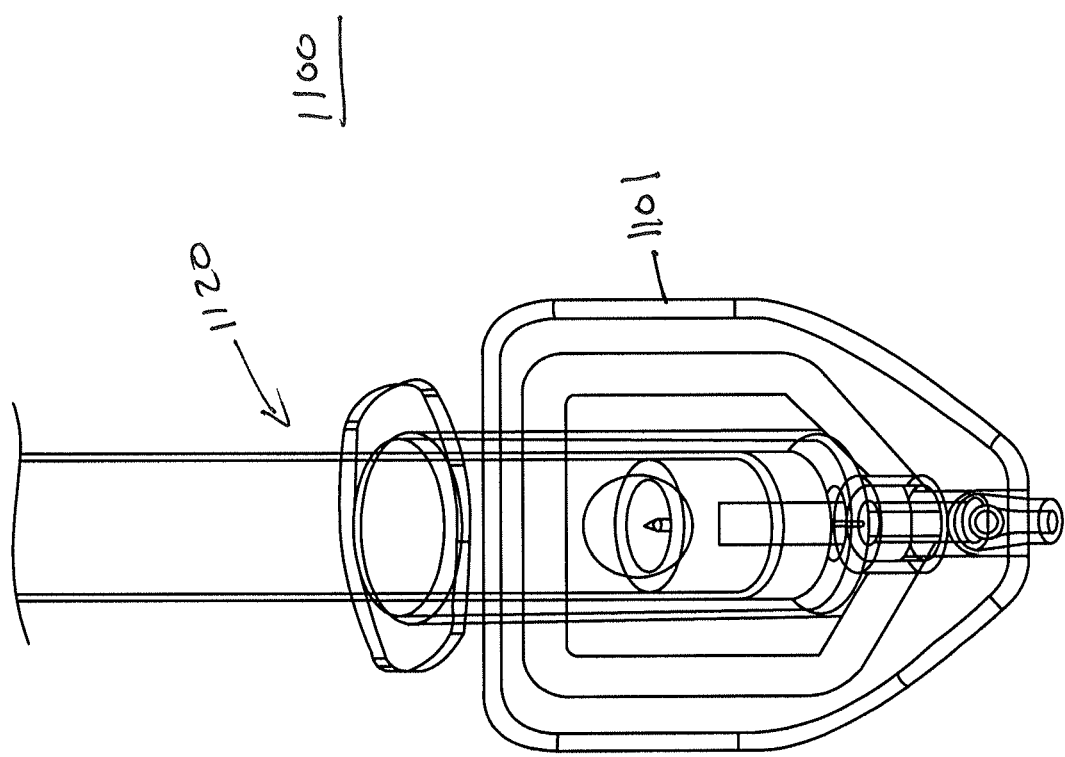
Figure 11E:
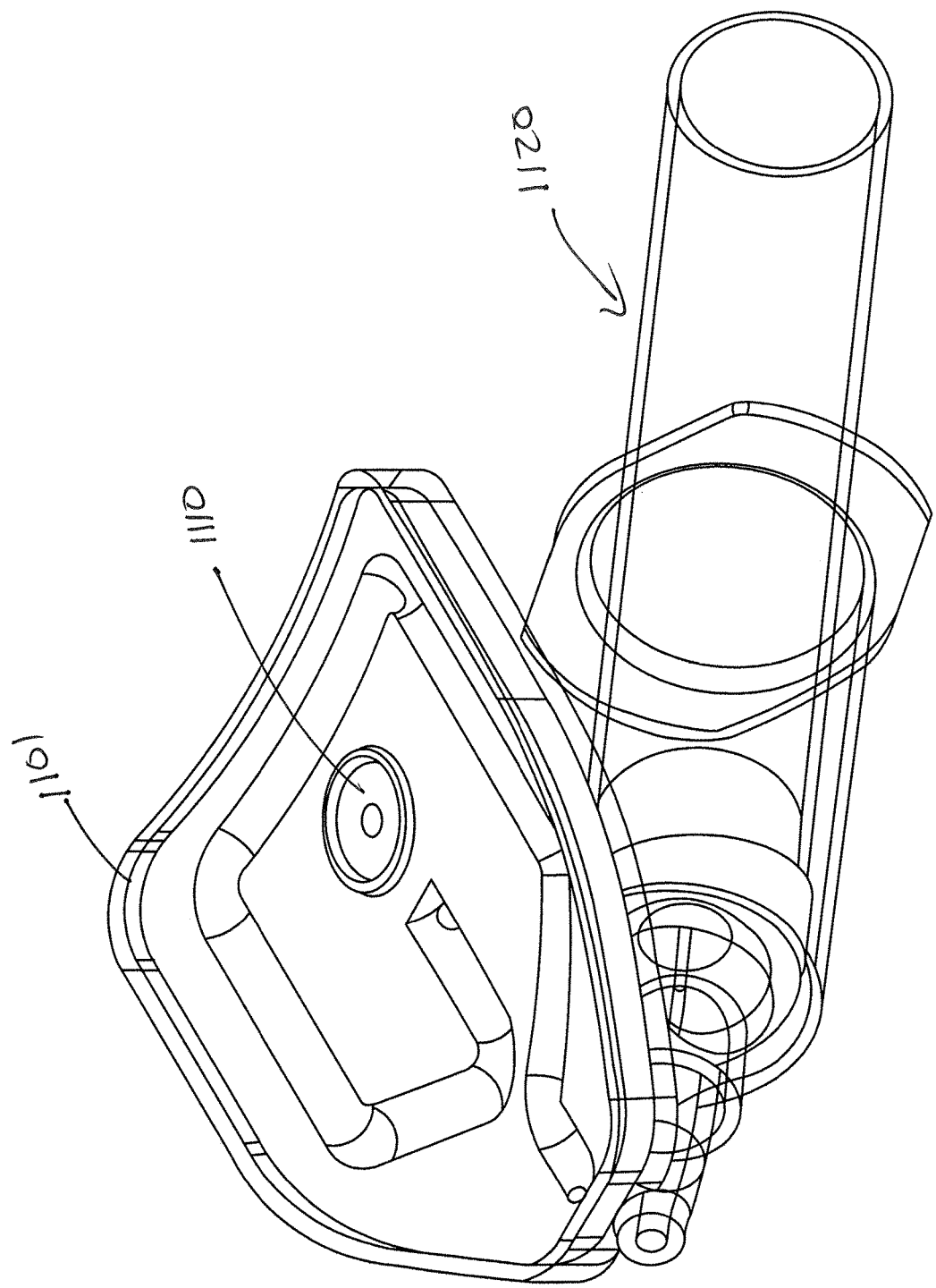

FIG. 9 illustrates a pathway splitter 900 for use in a blood sequestrations system, such as those shown in FIGS. 8A-8E, for example. The pathway splitter 900 includes an inlet port 902, a main line outlet port 904, and a sequestration channel outlet port 906. The inlet port 902 can be connected to main tubing that is in turn connected to a patient needle system, or directly to a patient needle. The main line outlet port 904 can be connected to main line tubing to a blood sampling system, such as a vacutainer base or housing, or directly to such blood sampling system. The sequestration channel outlet port 906 can be connected to sequestration tubing for receiving and sequestering a first sample of blood, up to a measured amount or predetermined threshold. Alternatively, the sequestration channel outlet port 906 can be connected to a sequestration chamber. The sequestration channel outlet port 906 is preferably 20-70 degrees angled from the main line outlet port 904, which in turn is preferably in-line with the inlet port 902. Once the predetermined amount of initial blood sample is sequestered in the sequestration tubing or chamber, in accordance with mechanisms and techniques described herein, follow-on blood samples will flow into the inlet port 902 and directly out the main line outlet port 904, without impedance.

FIGS. 10A-10D illustrate a blood sequestration device 1000 in accordance with alternative implementations. The blood sequestration device 1000 includes an inlet port 1002, a main outlet port 1004, and a sequestration channel port 1006. The inlet port 1002 can be connected to a patient needle or related tubing. The main outlet port 1004 can be connected to a blood sample collection device such as a Vacutainer, associated tubing, or a Luer activated valve, or the like. The sequestration channel port 1006 splits off from the main outlet port 1004 to a sequestration chamber 1008. In some implementations, the sequestration chamber 1008 is formed as a helical channel within a housing or other container 1001.

The sequestration chamber 1008 is connected at the distal end to an air permeable blood barrier 1010, substantially as described above. Air in the sequestration chamber 1008 is displaced through the air permeable blood barrier 1010 by an initial aliquot of blood that is guided into the sequestration channel port 1006. Once the sequestration chamber 1008 is filled, further blood draws through the main outlet port 1004 can be accomplished, where these samples will be non-contaminated.

FIGS. 11A-11E illustrate a blood sequestration device 1100 in accordance with other alternative implementations. The blood sequestration device 1100 includes an inlet port 1102, similar to the inlet ports described above, a main outlet port 1104, and a sequestration channel port 1106 that splits off from the main outlet port 1104 and inlet port 1102. The sequestration channel port is connected to a sequestration chamber 1108. In the implementation shown in FIGS. 11A-11E, the blood sequestration device includes a base member 1101 having a channel therein, which functions as the sequestration chamber 1108. The channel can be formed as a tortuous path through the base member 1101, which is in turn shaped and formed to rest on a limb of a patient.

A portion of the sequestration chamber 1108 can protrude from the base member or near a top surface of the base member, just before exiting to an air permeable blood barrier 1110, to serve as a blood sequestration indicator 1109. The indicator 1109 can be formed of a clear material, or a material that changes color when in contact with blood.

In some implementations, the blood sequestration device 1100 can include a blood sampling device 1120 such as a normally closed needle, Vacutainer™ shield or other collection device. The blood sampling device 1120 can be manufactured and sold with the blood sequestration device 1100 for efficiency and convenience, so that a first aliquot of blood that may be contaminated by a patient needle insertion process can be sequestered. Thereafter, the blood sampling device 1120 can draw non-contaminated blood samples to reduce the risk of false positive testing and ensure a non-contaminated sample.

FIGS. 12A-12D illustrate a blood sample optimization system 1200 in accordance with yet other alternative implementations. The system 1200 includes a blood sequestration device 1202 for attaching to a blood sampling device 1204, such as a Vacutainer™ or other collection and sampling device. The blood sequestration device 1202 is configured and arranged to receive, prior to a Vacutainer™ container or vial being attached to a collection needle of the blood sampling device 1204, a first aliquot or amount of blood, and sequester that first aliquot or amount in a sequestration channel of the blood sequestration device 1202.

In some implementations, the blood sequestration device 1202 can include an inlet port 1212, a main outlet port, and a sequestration channel port. The inlet port 1212 can be connected to a patient needle or related tubing. The main outlet port 1214 can be connected to a normally closed needle or device to enable connection with an evacuated blood collection container or other collection device such as a Vacutainer™, associated tubing, luer connectors, syringe, a Luer activated valve, or the like. The sequestration channel port splits off from the main outlet port to a sequestration chamber 1218.

Figure 12A:
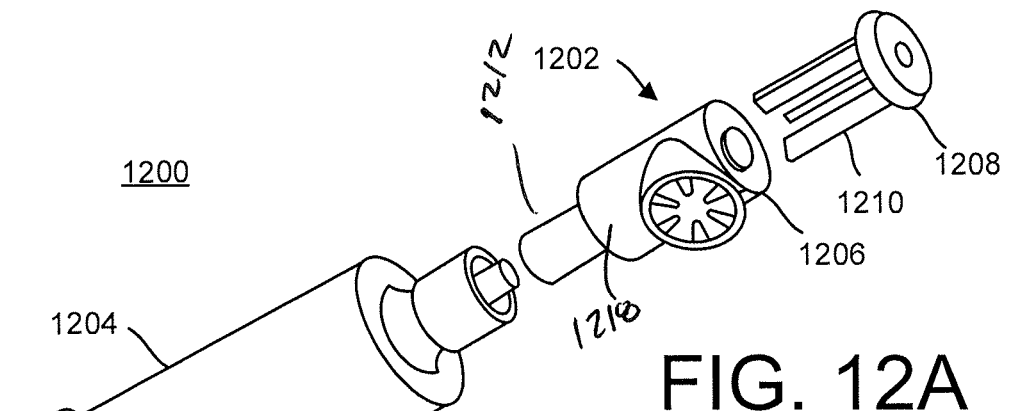
FIGS. 12A-12D illustrate a blood sample optimization system including a blood sequestration device in accordance with yet other alternative implementations.
Figure 12B:
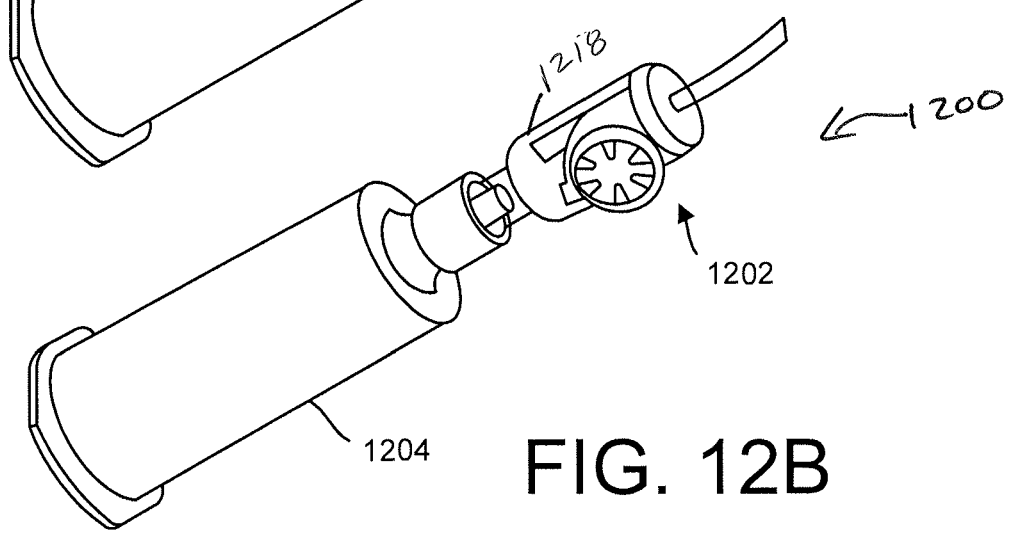
Figure 12C:
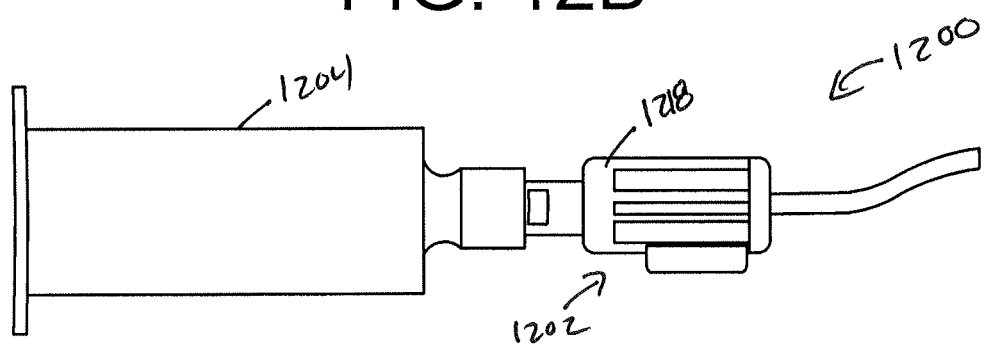
Figure 12D:
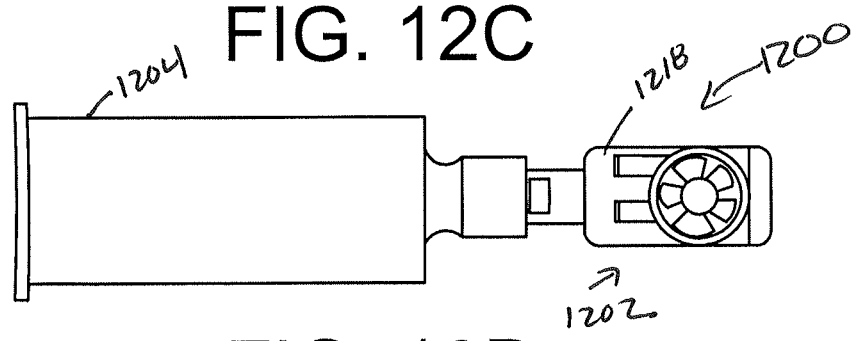
Figure 13A:
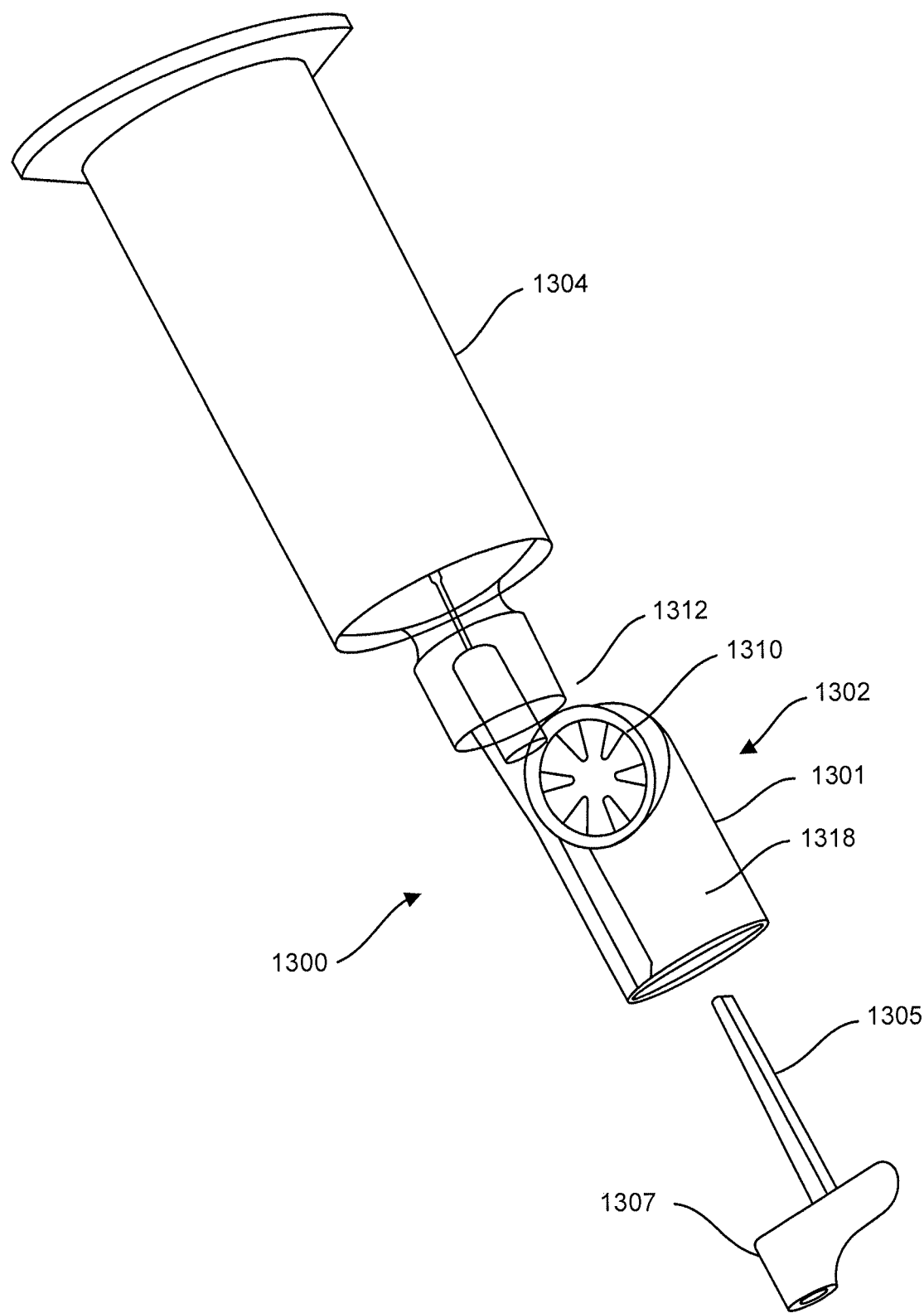
FIGS. 13A-13D illustrate a blood sample optimization system 1300 in accordance with yet another alternative implementations.
Figure 13B:
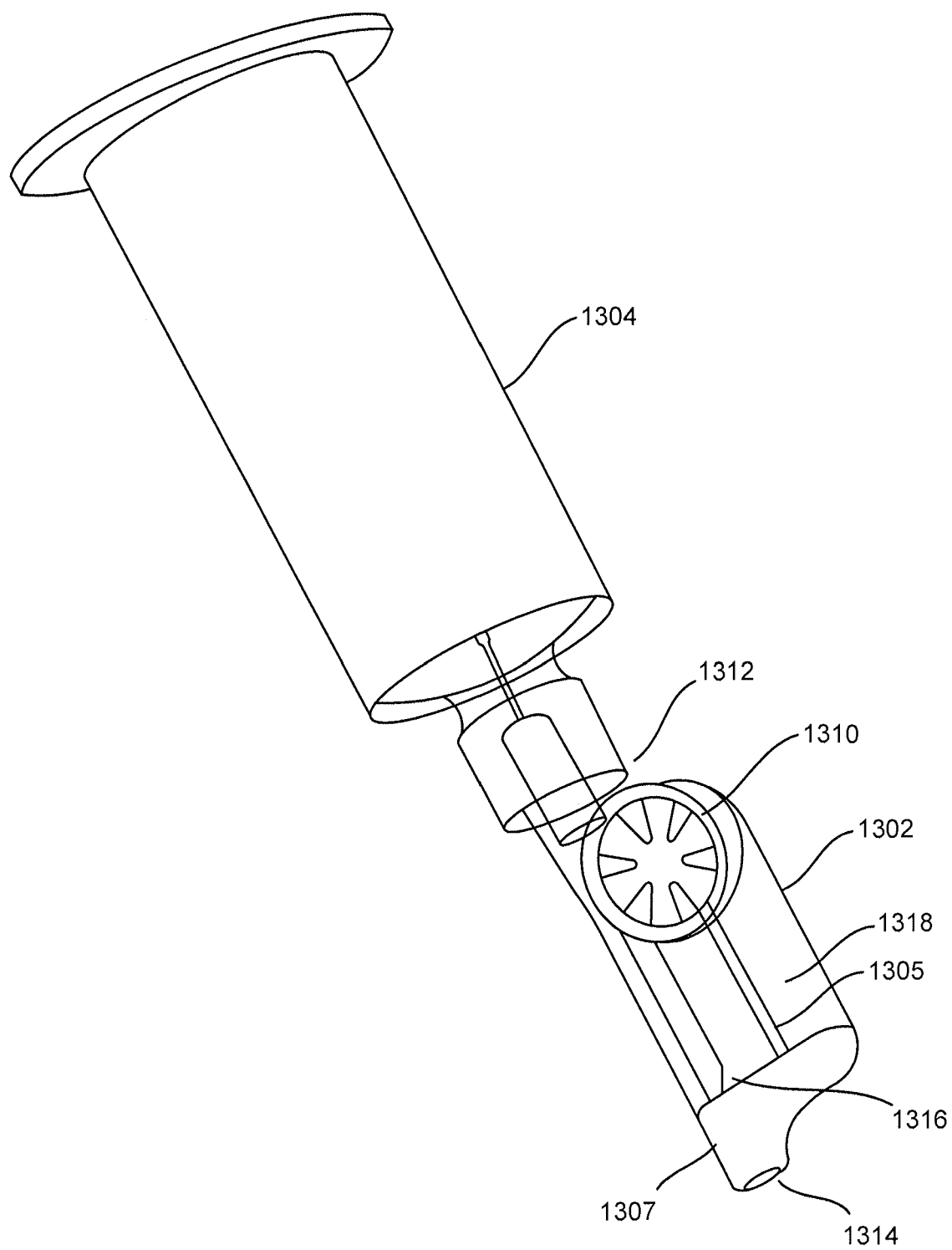
Figure 13C:
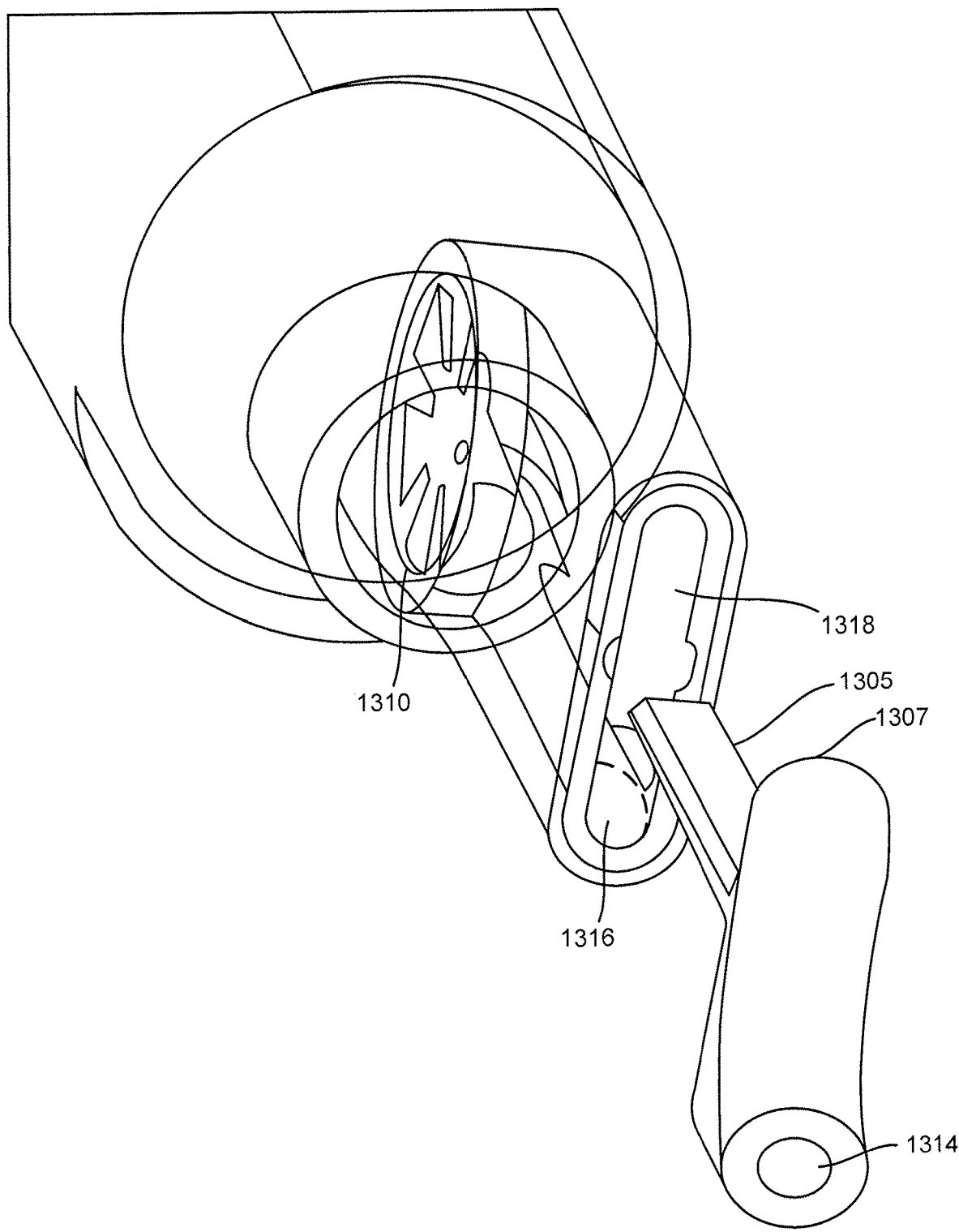
Figure 13D:
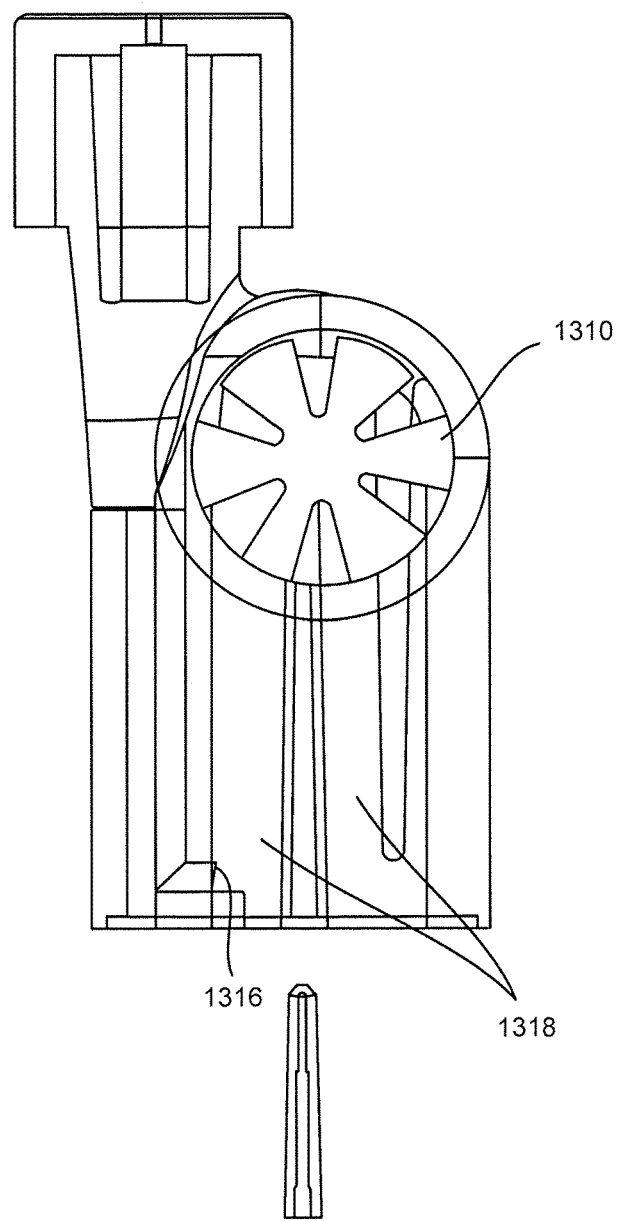

In some implementations, the sequestration chamber 1218 is formed as a channel within the body of a sequestration device 1202. The sequestration chamber 1218 can be a winding channel, such as a U-shaped channel, an S-shaped channel, a helical channel, or any other winding channel. The sequestration device 1202 can include a housing or other containing body, and one or more channels formed therein. As shown in FIGS. 12A and 12B, the sequestration device 1202 includes a main body 1206 and a cap 1208. The main body 1206 is formed with one or more cavities or channels, which are further formed with one or more arms 1210 that extend from the cap 1208, and which abut the cavities or channels in the main body 1206 to form the primary collection port and main outlet port.

FIGS. 13A-13D illustrate a blood sample optimization system 1300 in accordance with yet other alternative implementations. The system 1300 includes a blood sequestration device 1302 for attaching to a blood sampling device 1304, such as a Vacutainer or other bodily fluid collection and sampling device. The blood sequestration device 1302 is configured and arranged to receive, prior to a Vacutainer container or vial being attached to a collection needle of the blood sampling device 1304, a first aliquot or amount of blood, and to sequester that first aliquot or amount of blood or other bodily fluid in a sequestration channel of the blood sequestration device 1302.

The blood sequestration device 1302 includes a housing 1301 having an inlet port 1314, a main outlet port 1312, and a sequestration channel port 1316. The inlet port 1314 can be connected to a patient needle or associated tubing. The main outlet port 1312 can be connected to a normally closed needle or device to enable connection with an evacuated blood collection container or other collection device such as a Vacutainer™ associated tubing, luer connectors, syringe, a Luer activated valve, or the like. The sequestration channel port 1316 splits off from the main inlet port 1314 to a sequestration chamber 1318.

In the implementation shown in FIGS. 13A-D, the sequestration chamber 1318 is formed as a cavity or chamber within housing 1301 or formed by walls that define housing 1301. The sequestration chamber 1318 can be a winding channel, such as a U-shaped channel, an S-shaped channel, a helical channel, or any other winding channel, that is defined by the cooperation and connection of housing 1301 with cap 1307 which cap 1307 can include a protrusion 1305 that provides one or more walls or directors for the winding channel in the sequestration chamber 1318. The protrusion 1305 from the cap 1307 can be straight or curved, and may have various channels, apertures or grooves embedded therein, and can extend from the cap 1307 any angle or orientation. When the cap 1307 is connected with the housing 1301 to complete the formation of the sequestration chamber 1318, the protrusion 1305 forms at least part of the winding channel to sequester a first aliquot or amount of blood or other bodily fluid in a sequestration channel formed in the sequestration chamber 1318 and by the winding channel.

The sequestration chamber 1318 includes an air permeable blood barrier 1310, substantially as described above. Air in the sequestration chamber 1318 is displaced through the air permeable blood barrier 1310 by an initial aliquot of blood that is provided into the sequestration chamber 1318 by the blood pressure of the patient. Once the sequestration chamber 1318 is filled and the air in the sequestration chamber 1318 displaced, the blood pressure of the patient will be insufficient to drive or provide further blood into the blood sequestration device 1302, and in particular the outlet port 1312, until a force such as a vacuum or other pressure, such as provided by the blood sample collection device like Vacutainer is provided to draw out a next aliquot or amount of blood or bodily fluid. Further blood draws through the main outlet port 1312 can be accomplished, where these samples will be non-contaminated since any contaminants would be sequestered in the sequestration chamber 1318 with the first aliquot of blood.

FIGS. 14A-14E illustrate yet another implementation of a blood sampling system 1400 to sequester contaminates of an initial aliquot or sample to reduce false positives in blood cultures or tests performed on a patient's blood sample. The blood sampling system 1400 includes a blood sequestration device 1401 that can be connected between a blood sample collection device 1403 and a patient needle (not shown). The blood sample collection device 1403 can be a Vacutainer or the like. The blood sequestration device 1401 includes an inlet port 1402 that can be connected with a patient needle that is inserted into a patient's vascular system for access to and withdrawing of a blood sample. The inlet port 1402 may also be connected with tubing or other conduit that is in turn connected with the patient needle.

The inlet port 1402 defines an opening into the blood sequestration device 1401, which opening can be the same cross sectional dimensions as tubing or other conduit connected with the patient needle or the patient needle itself. For instance, the opening can be circular with a diameter of approximately 0.045 inches, but can have a diameter of between 0.01 inches or less to 0.2 inches or more. The blood sequestration device 1401 further includes an outlet port 1404, which defines an opening out of the blood sequestration device 1401 and to the blood sample collection device 1403. The outlet port 1404 may also be connected with tubing or other conduit that is in turn connected with the blood sequestration device 1403. The outlet port 1404 can further include a connector device such as a threaded cap, a Luer connector (male or female), a non threaded interference or glue joint fitting for attachment of various devices including but not limited to tubing, or the like.

The blood sequestration device 1401 further includes a sampling channel 1406 between the inlet port 1402 and the outlet port 1404, and which functions as a blood sample pathway once a first aliquot of blood has been sequestered. The sampling channel 1406 can be any sized, shaped or configured channel, or conduit. In some implementations, the sampling channel 1406 has a substantially similar cross sectional area as the opening of the inlet port 1402. In other implementations, the sampling channel 1406 can gradually widen from the inlet port 1402 to the outlet port 1404.

Figure 14A:
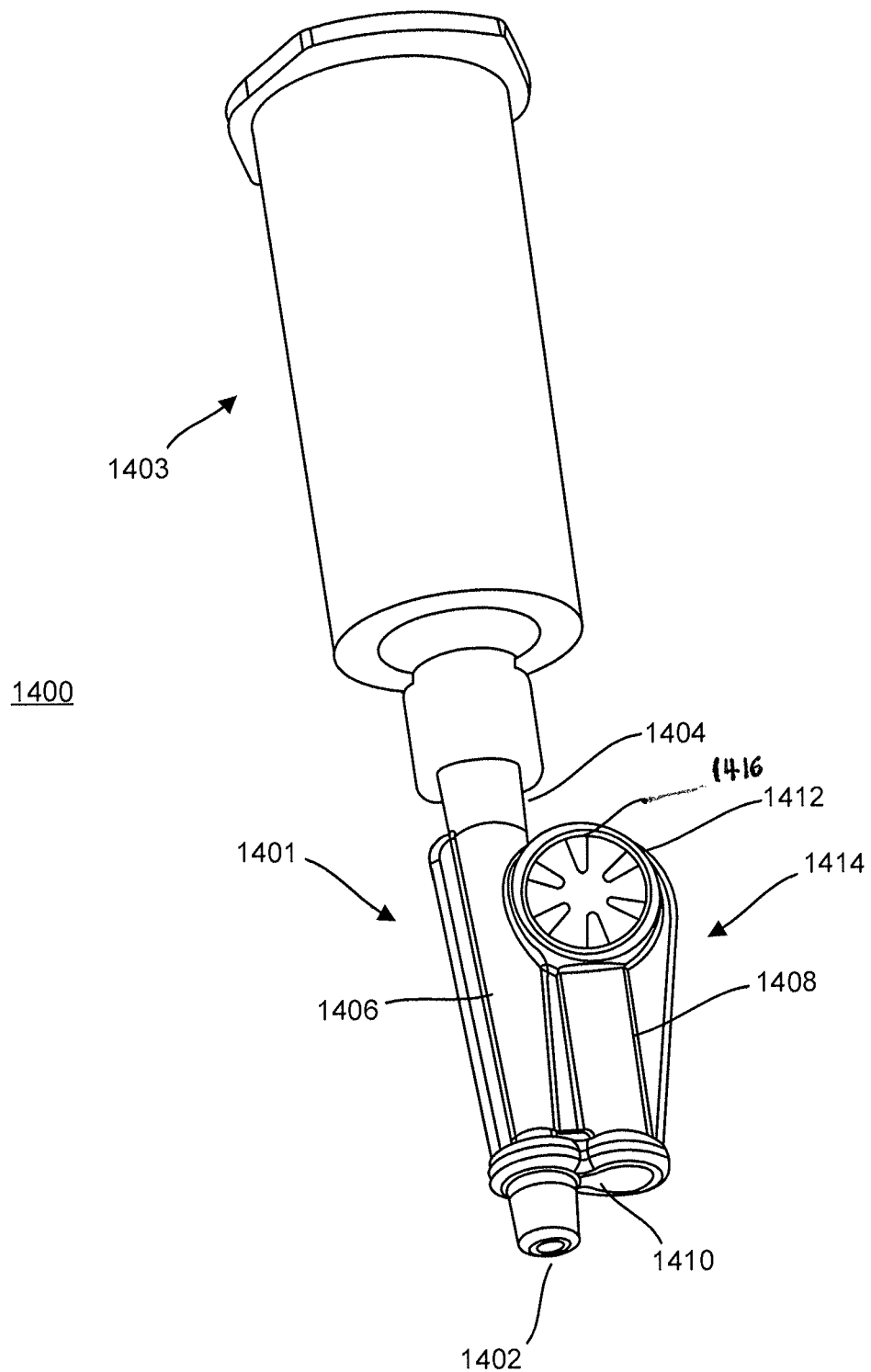
FIGS. 14A-14E illustrate yet another implementation of a blood sampling system to sequester contaminates of an initial aliquot or sample to reduce false positives in blood cultures or tests performed on a patient's blood sample.
Figure 14B:
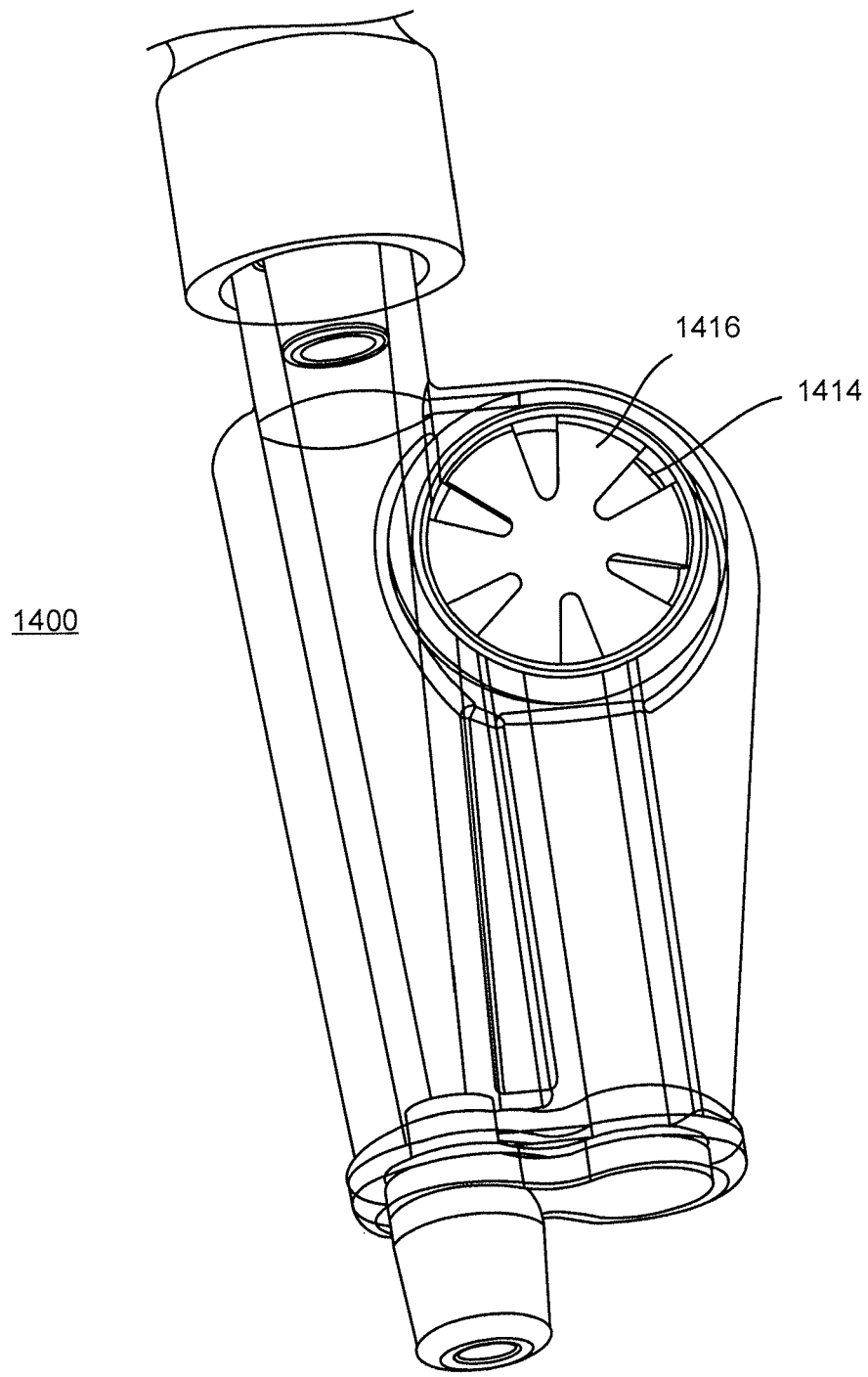

The blood sequestration device 1401 further includes a sequestration chamber 1408 that is connected to and split off or diverted from the sampling channel 1406 at any point between the inlet port 1402 and the outlet port 1404, but preferably from a proximal end of the sampling channel 1406 near the inlet port 1402. The sequestration chamber 1408 is at first maintained at atmospheric pressure, and includes an air outlet 1412 at or near a distal end of the sequestration chamber 1408 opposite the diversion point from the sampling channel 1406. The air outlet 1412 includes an air permeable blood barrier 1412. As shown in FIG. 14B, the air permeable blood barrier 1412 can be overlaid with a protective cover 1416. The protective cover 1416 can be sized and configured to inhibit a user from touching the air permeable blood barrier 1412 with their finger or other external implement, while still allowing air to exit the air permeable blood barrier 1412 as the air is displaced from the sequestration chamber 1408 by blood being forced into the sequestration chamber 1408 by a patient's own blood pressure. In addition the protective cover 1416 can be constructed to inhibit or prevent accidental exposure of the air permeable blood barrier to environmental fluids or splashes. This can be accomplished in a variety of mechanical ways including but not limited to the addition of a hydrophobic membrane to the protective cover.

Figure 14C:
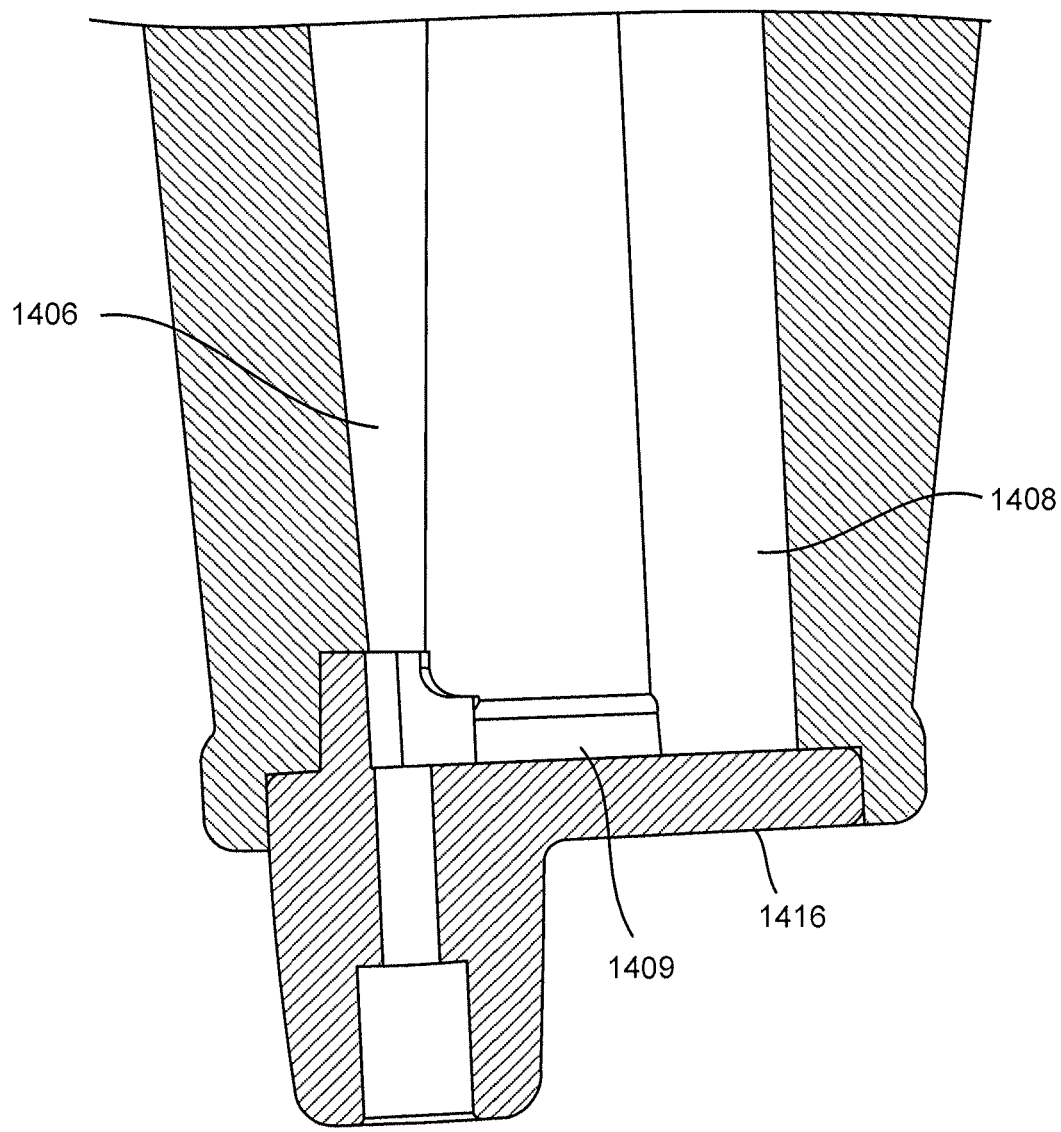
Figure 14D:
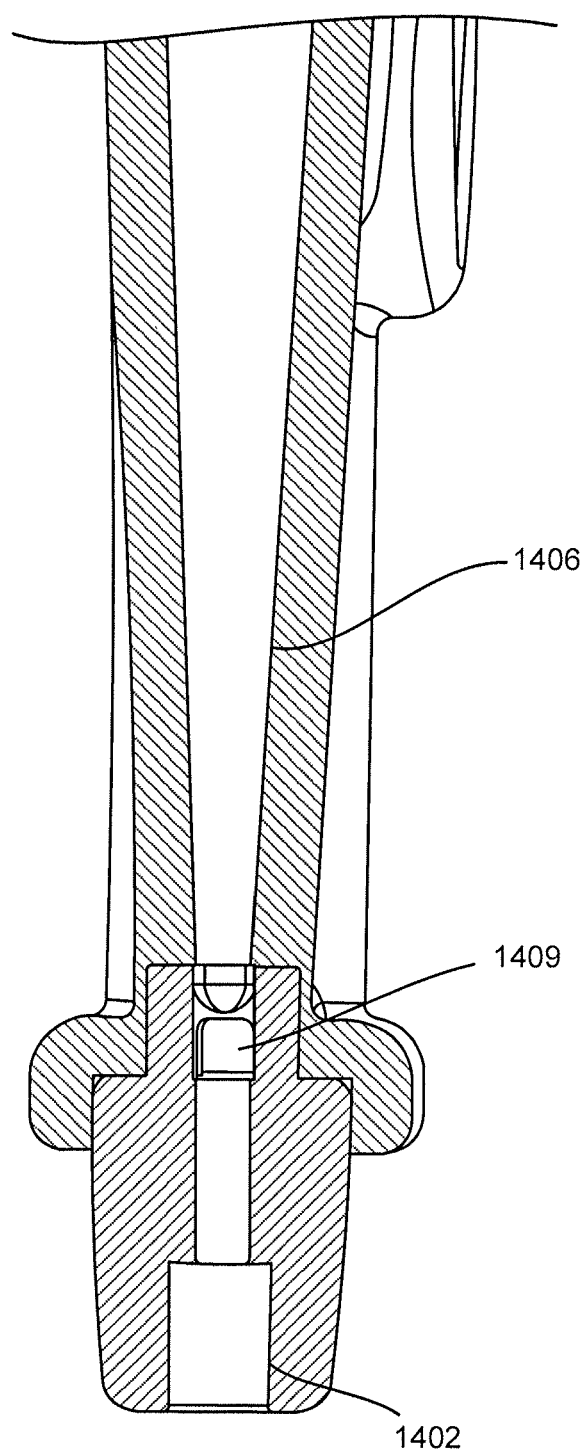
Figure 14E:
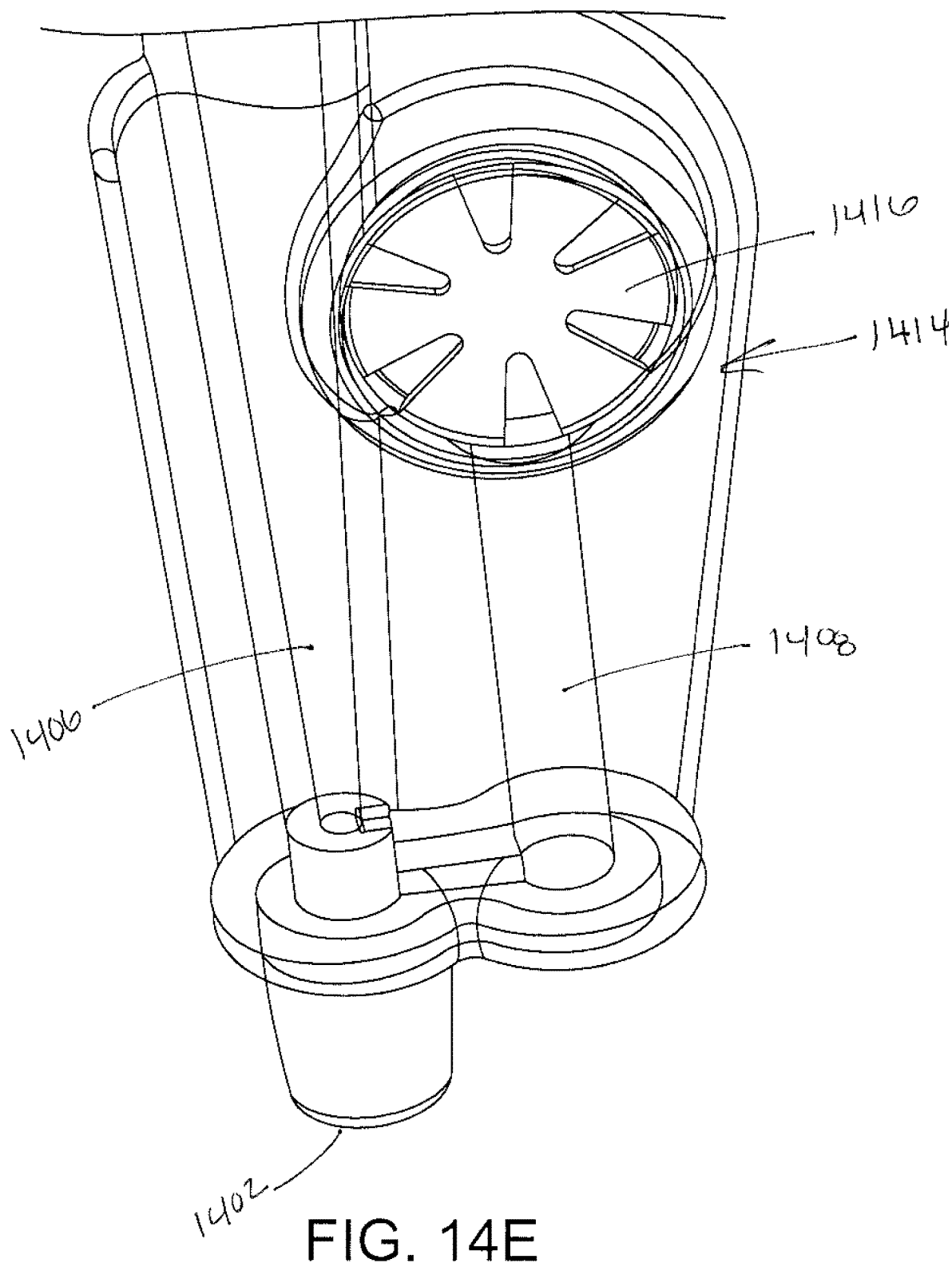

As shown in FIGS. 14C and 14D, the sampling channel 1406 can be cylindrical or frusto-conical in shape, going from a smaller diameter to a larger diameter, to minimize a potential to lyse red blood cells. Likewise, the sampling channel 1406 is formed with a minimal amount of or no sharp turns or edges, which can also lyse red blood cells. The sampling channel 1406 splits off to the sequestration chamber 1408 near the inlet port 1402 via a diversion pathway 1409. The diversion pathway 1409 can have any cross-sectional shape or size, but is preferably similar to the cross-sectional shape of at least part of the inlet port 1402.

In some implementations, the sampling channel 1406 and the sequestration chamber 1408 are formed by grooves, channels, locks or other pathways formed in housing 1414. The housing 1414 can be made of plastic, metal or other rigid or semi-rigid material. The housing 1414 can have a bottom member that sealably mates with a top member. One or both of the bottom member and the top member can include the sampling channel 1406 and the sequestration chamber 1408, as well as the diversion pathway 1409, the inlet port 1402, and the outlet port 1404. In some other implementations, one or more of the diversion pathway 1409, the inlet port 1402, and/or the outlet port 1404 can be at least partially formed by a cap member that is connected to either end of the housing 1414. In some implementations, the top member and the bottom member, as well as the cap member(s), can be coupled together by laser welding, heat sealing, gluing, snapping, screwing, bolting, or the like. In other implementations, some or all of the interior surface of the diversion pathway 1409 and/or sequestration chamber 1408 can be coated or loaded with an agent or substance, such as a decontaminate, solidifying agent, or the like. For instance, a solidifying agent can be provided at the diversion pathway 1409 such that when the sequestration chamber 1408 is filled and the initial aliquot of blood backs up to the diversion pathway 1409, that last amount of sequestered blood could solidify, creating a barrier between the sequestration chamber 1408 and the sampling channel 1406.

FIGS. 15A-15G illustrate a blood sequestration device 1500. The blood sequestration device 1500 can be connected to a normally closed needle or device to enable connection with an evacuated blood collection container or other collection device such as a Vacutainer™, associated tubing, luer connectors, syringe, a Luer activated valve, or the like.

The blood sequestration device 1500 includes an inlet port 1502 that can be connected with a patient needle that is inserted into a patient's vascular system for access to and withdrawing of a blood sample. The inlet port 1502 may also be connected with tubing or other conduit that is in turn connected with the patient needle. The inlet port 1502 defines an opening into the blood sequestration device 1500, which opening may be the same cross sectional dimensions as tubing or other conduit connected with the patient needle or the patient needle itself. For instance, the opening can be circular with a diameter of approximately 0.045 inches, but can have a diameter of between 0.01 inches or less to 0.2 inches or more.

The inlet port 1502 can also include a sealing or fluid-tight connector or connection, such as threading or Luer fitting, or the like. In some implementations, tubing or other conduit associated with the patient needle can be integral with the inlet port 1502, such as by co-molding, gluing, laser weld, or thermally bonding the parts together. In this manner, the blood sequestration device 1500 can be fabricated and sold with the patient needle as a single unit, eliminating the need for connecting the patient needle to the blood sequestration device 1500 at the time of blood draw or sampling.

The blood sequestration device 1500 further includes an outlet port 1504, which defines an opening out of the blood sequestration device 1500 and to the blood sample collection device. The outlet port 1504 may also be connected with tubing or other conduit that is in turn connected with the blood sequestration device, and may also include a sealing or fluid-tight connector or connection, such as threading or Luer fitting, or the like. Accordingly, as discussed above, the blood sequestration device 1500 can be fabricated and sold with the patient needle and/or tubing and the blood sample collection device as a single unit, eliminating the need for connecting the patient needle and the blood sample collection device to the blood sequestration device 1500 at the time of blood draw or sampling.

The blood sequestration device 1500 further includes a sampling channel 1506 between the inlet port 1502 and the outlet port 1504, and which functions as a blood sample pathway once a first aliquot of blood has been sequestered. The sampling channel 1506 can be any sized, shaped or configured channel or conduit. In some implementations, the sampling channel 1506 has a substantially similar cross sectional area as the opening of the inlet port 1502. In other implementations, the sampling channel 1506 can gradually widen from the inlet port 1502 to the outlet port 1504.

The blood sequestration device 1500 further includes a sequestration chamber 1508 that is connected to and split off or diverted from the sampling channel 1506 at any point between the inlet port 1502 and the outlet port 1504, but preferably from a proximal end of the sampling channel 1506 near the inlet port 1502. In some implementations, the diversion includes a Y-shaped junction. The sequestration chamber 1508 is preferably maintained at atmospheric pressure, and includes a vent 1510 at or near a distal end of the sequestration chamber 1508. The vent 1510 includes an air permeable blood barrier 1512. FIG. 15C illustrates the blood sequestration device 1500 with the sequestration chamber 1508 filled with a first aliquot or sample of blood from the patient.

The air permeable blood barrier 1512 can be covered with a protective cover 1516. The protective cover 1516 can be sized and configured to inhibit a user from touching the air permeable blood barrier 1512 with their finger or other external implement, while still allowing air to exit the air permeable blood barrier 1512 as the air is displaced from the sequestration chamber 1508 by blood being forced into the sequestration chamber 1508 by a patient's own blood pressure. The protective cover 1516 can be constructed to inhibit or prevent accidental exposure of the filter to environmental fluids or splashes. This can be accomplished in a variety of mechanical ways including but not limited to the addition of a hydrophobic membrane to the protective cover.

Figure 15A:
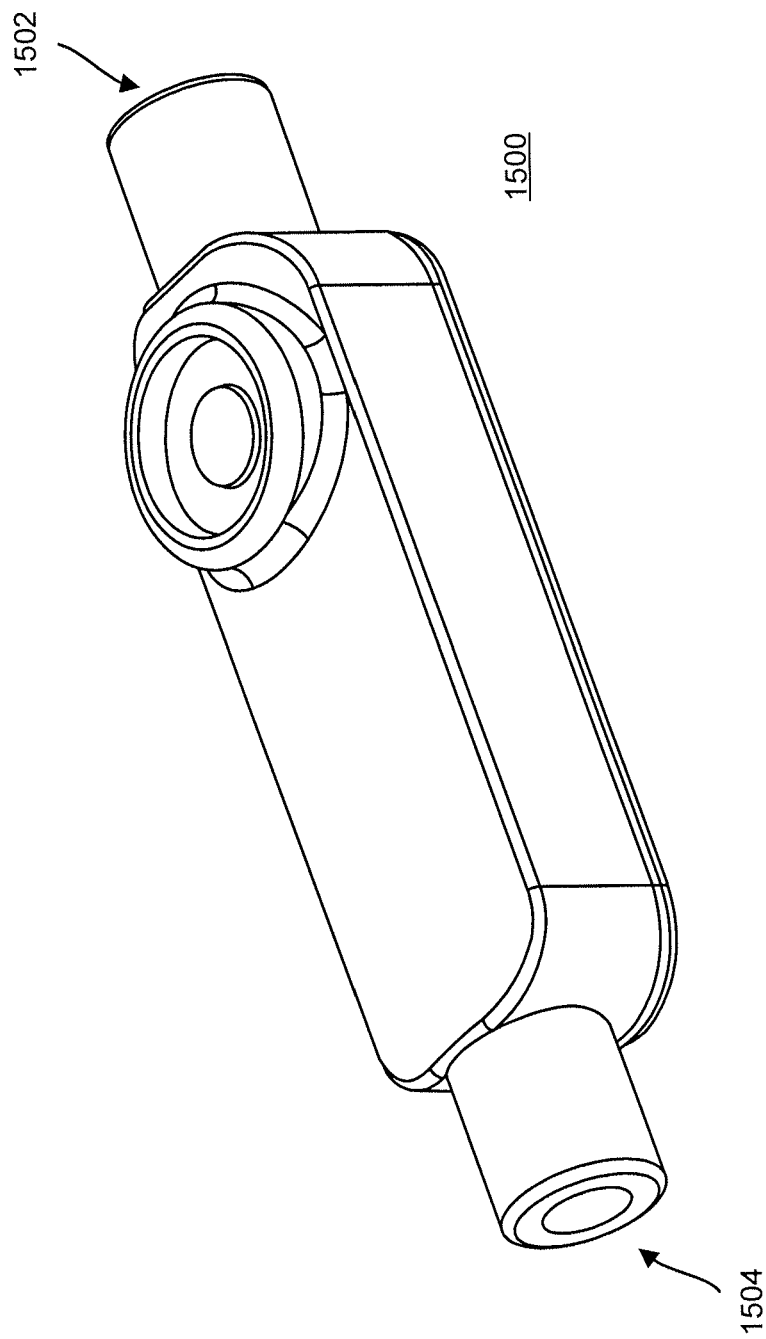
FIGS. 15A-15G illustrate a blood sequestration device and method of using the same, in accordance with yet another implementation.
Figure 15B:
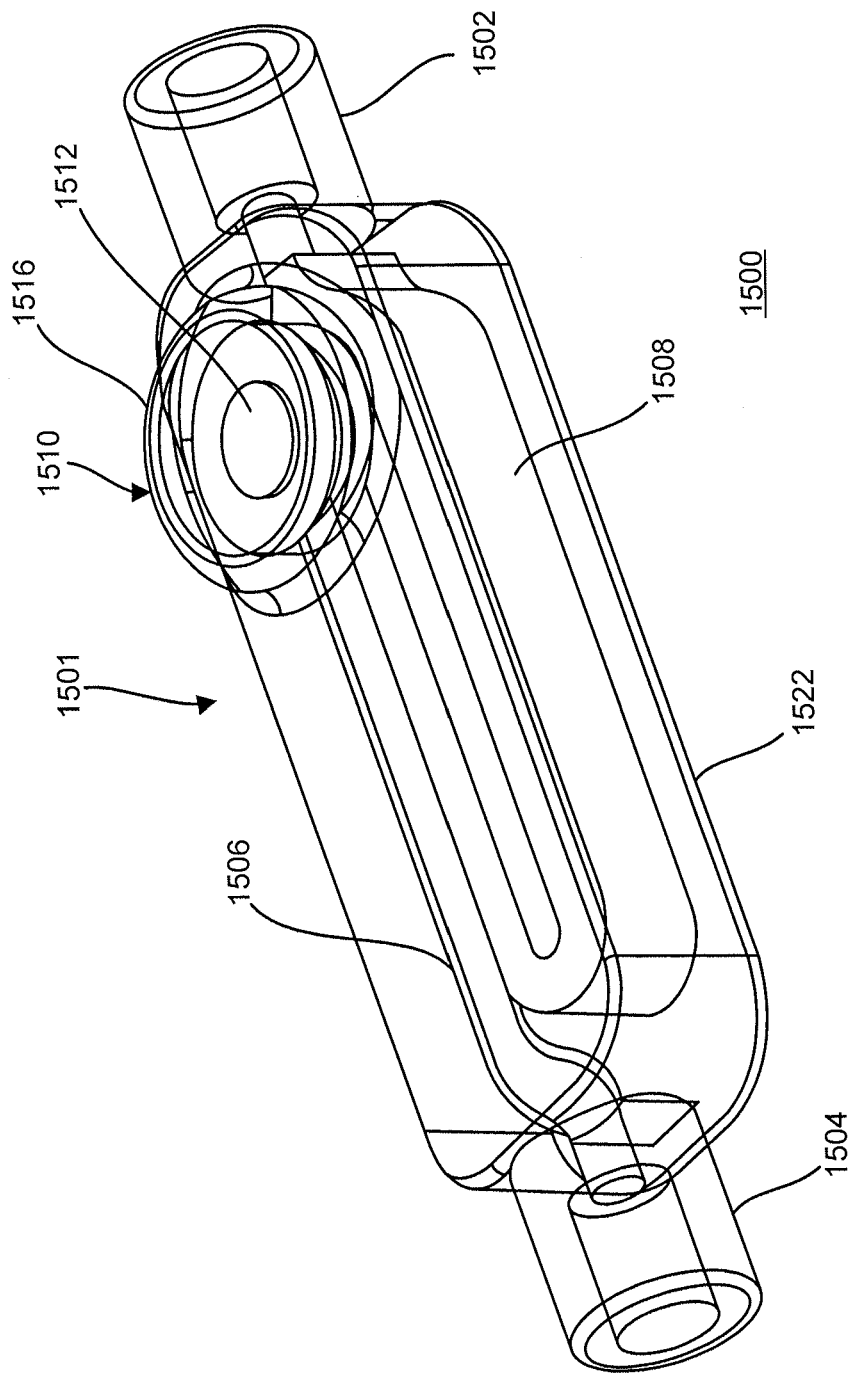
Figure 15C:
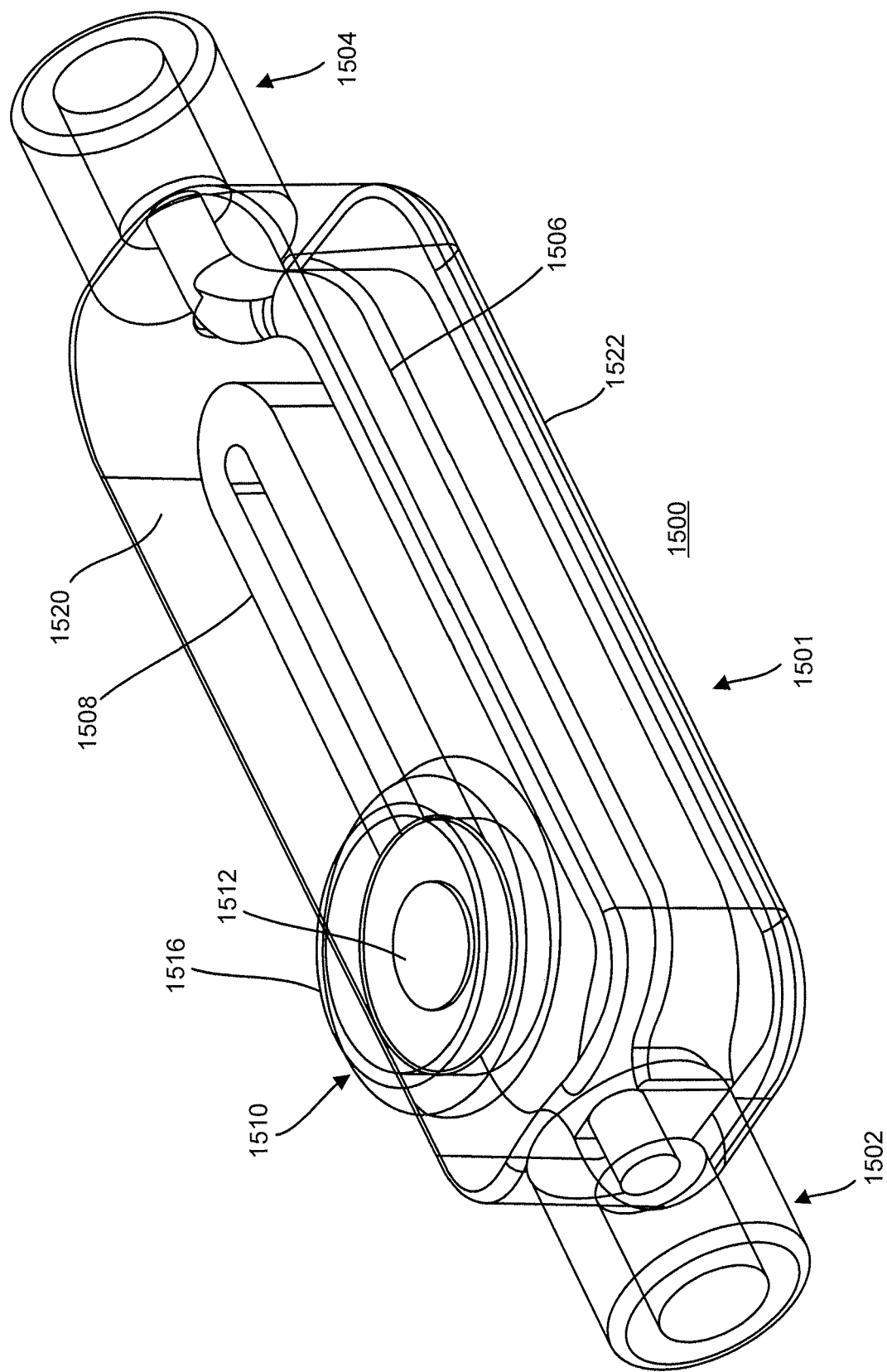

FIG. 15B is a perspective view of the blood sequestration device 1500 from the outlet port 1504 and top side of a housing 1501 of the blood sequestration device 1500 that includes the vent 1510, and illustrating an initial aliquot of blood filling sequestration chamber 1508 while the sampling channel 1506 is empty, before a sample collection device is activated. FIG. 15G is a perspective view of the blood sequestration device 1500 from the outlet port 1504 and bottom side of the housing 1501 of the blood sequestration device 1500, and illustrating the initial aliquot of blood filling sequestration chamber 1508 while the sampling channel 1506 is empty, before the sample collection device is activated. FIG. 15C is another perspective view of the blood sequestration device 1500 from the inlet port 1502 and top side of a housing 1501 of the blood sequestration device 1500 that includes the vent 1510, and illustrating blood now being drawn through sampling channel 1506 while the sequestered blood remains substantially in the sequestration chamber 1508.

Figure 15D:
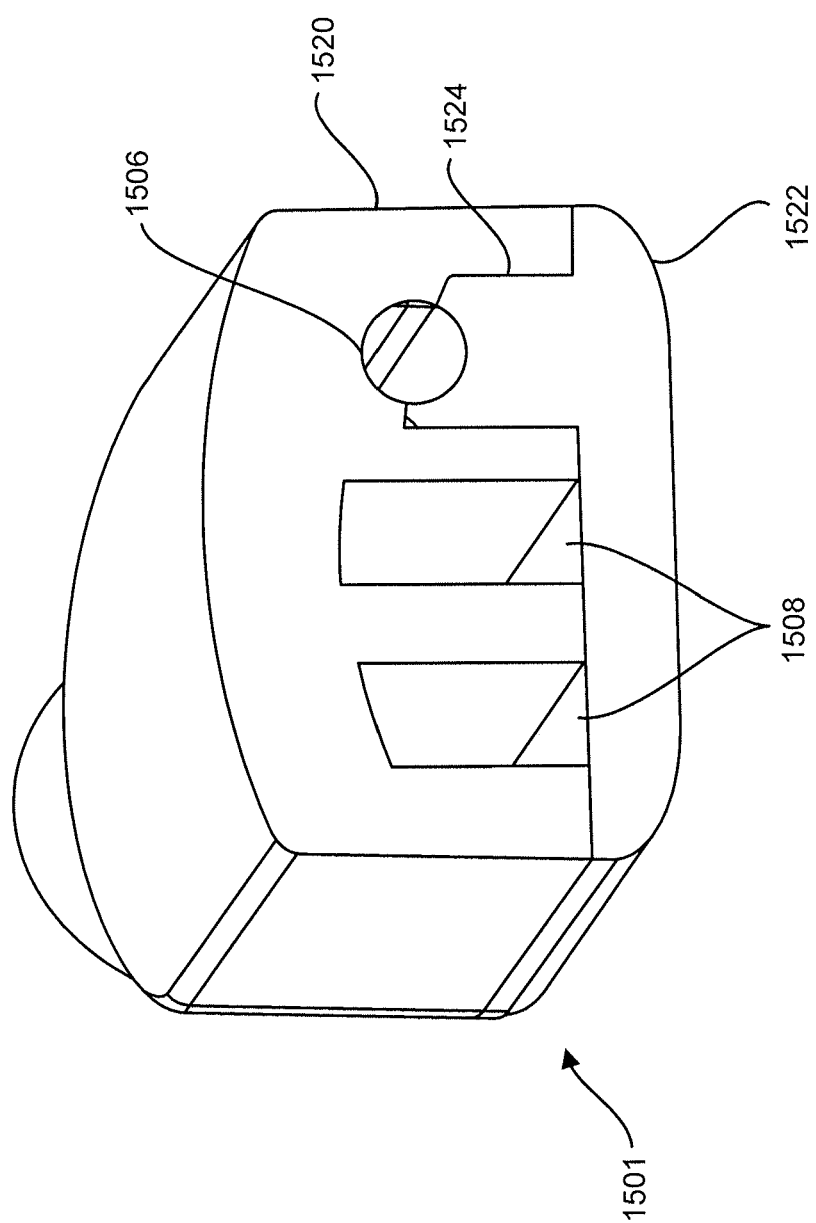
Figures 15E, 15F:
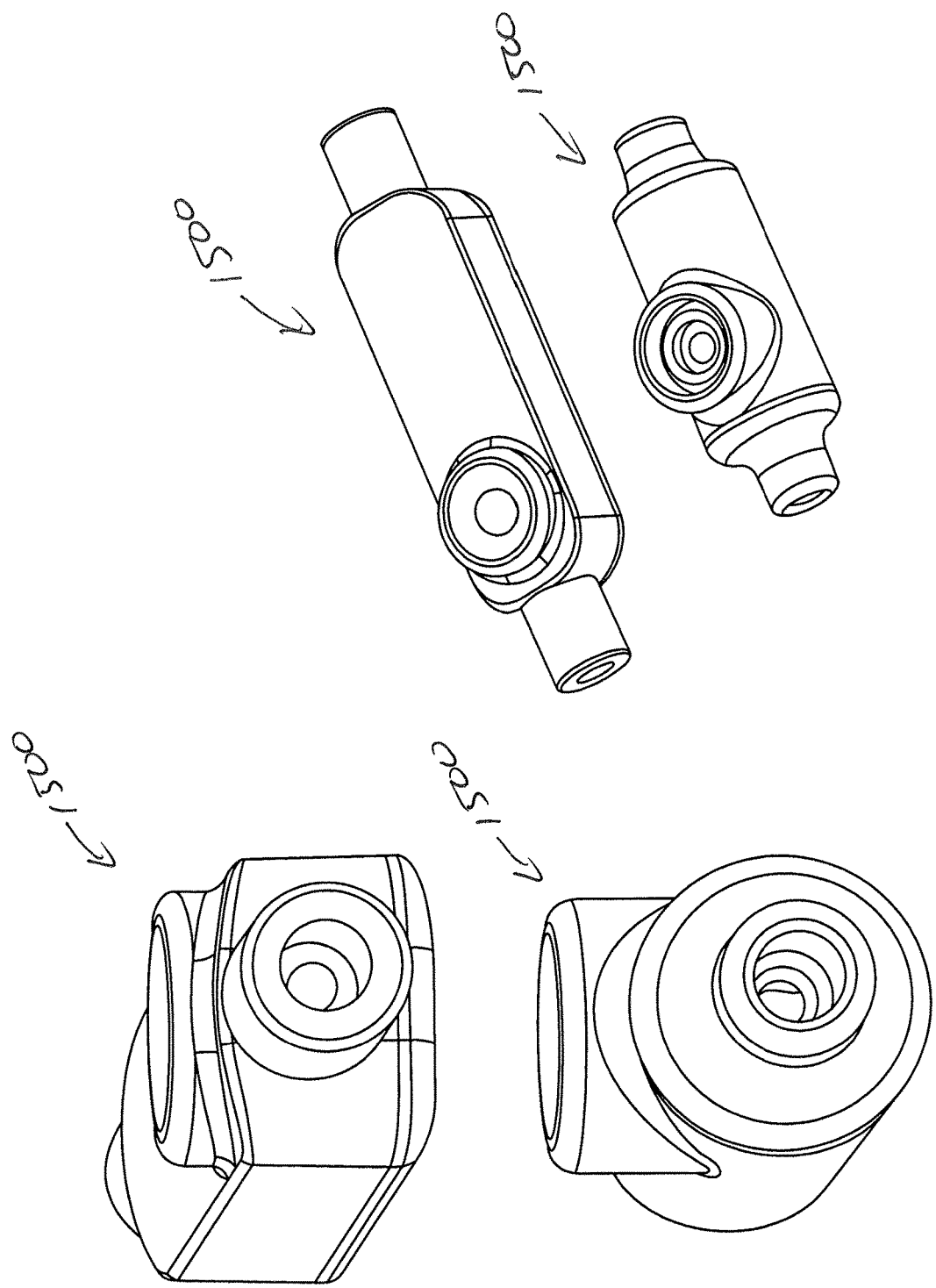
Figure 15G:
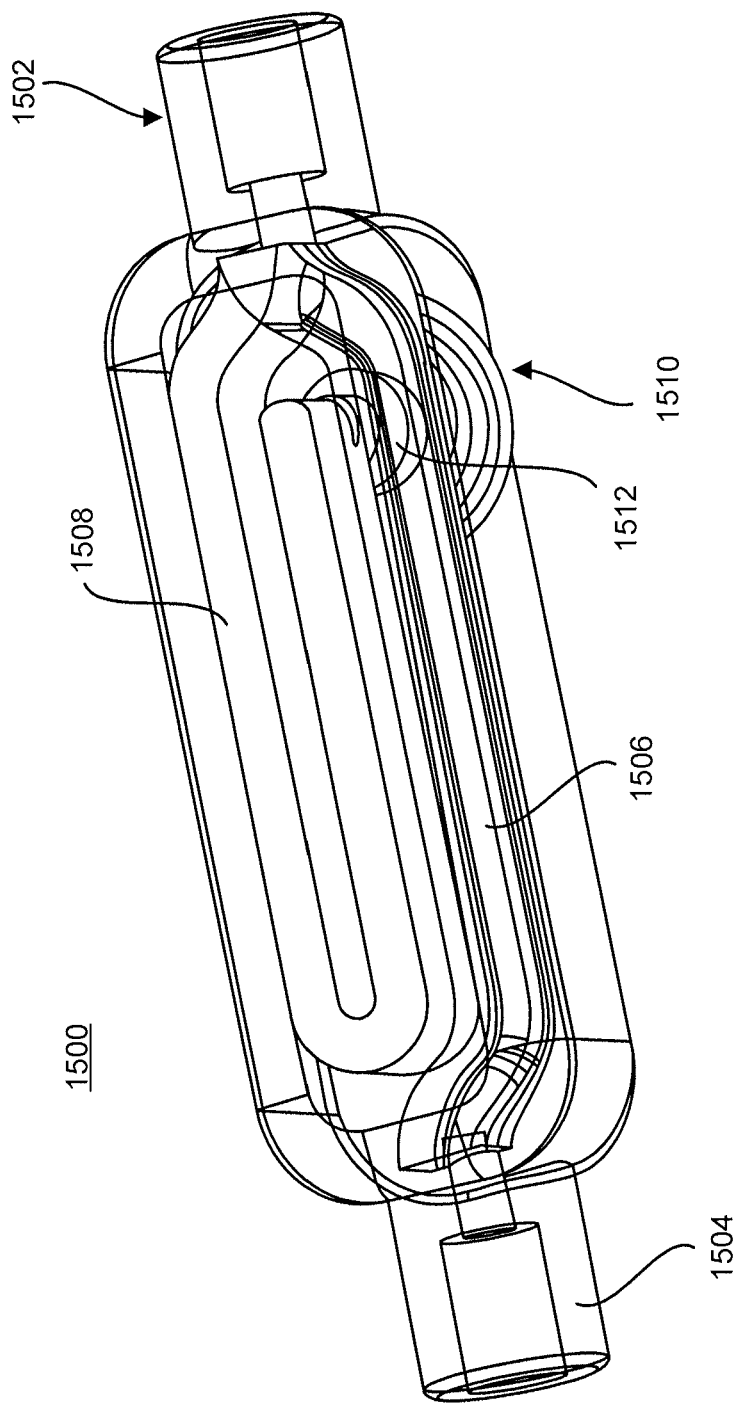
Figure 16D:
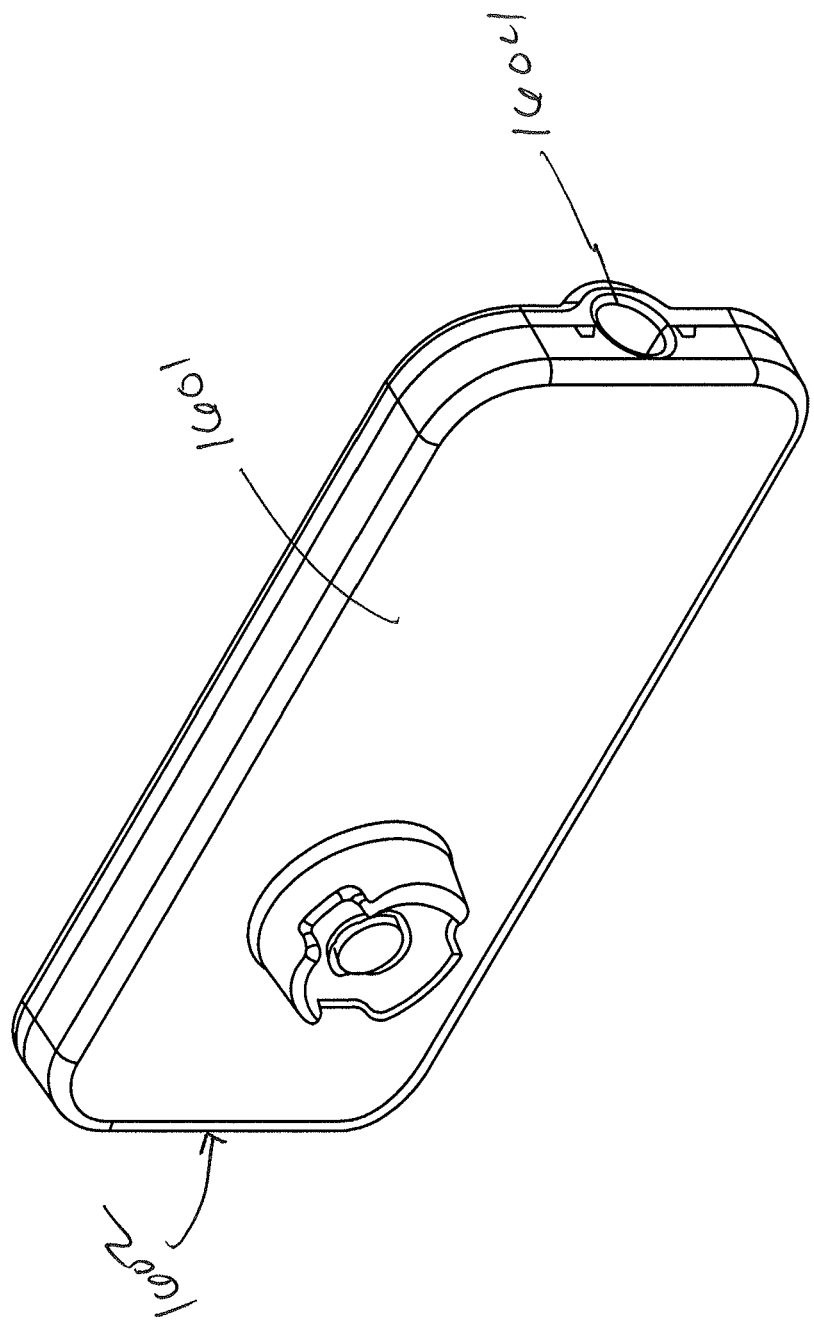

FIG. 15D is a cross section of the blood sequestration device 1500 in accordance with some implementations, showing the housing 1501 that defines the sampling channel 1506 and the sequestration chamber 1508. FIGS. 15E and 15F illustrate various form factors of a housing for a blood sequestration device, in accordance with one or more implementations described herein.

The sequestration chamber 1508 can have a larger cross-sectional area than the sampling channel 1506, and the cross-sectional area and length can be configured for a predetermined or specific volume of blood to be sequestered or locked. The sampling channel 1506 can be sized to be compatible with tubing for either or both of the patient needle tubing or the blood collection device tubing.

The housing 1501 can be formed of multiple parts or a single, unitary part. In some implementations, and as illustrated in FIG. 15D, the housing 1501 includes a top member 1520 and a bottom member 1522 that are mated together, one or both of which having grooves, channels, locks, conduits or other pathways pre-formed therein, such as by an injection molding process or by etching, cutting, drilling, etc. The top member 1520 can be connected with the bottom member 1522 by any mating or connection mechanism, such as by laser welding, thermal bonding, ultrasonic welding, gluing, using screws, rivets, bolts, or the like, or by other mating mechanisms such as latches, grooves, tongues, pins, flanges, or the like.

In some implementations, such as shown in FIG. 15D, the top member 1520 can include the grooves, channels, locks, conduits or other pathways, while the bottom member 1522 can include a protrusion 1524 that is sized and adapted to fit into at least one of the grooves, channels, locks or other pathways of the top member 1520. The protrusion 1524 can provide a surface feature, such as a partial groove or channel, for instance, to complete the formation of either the sampling channel 1506 and/or the sequestration chamber 1508. In some implementations, the protrusion 1524 can be formed with one or more angled sides or surfaces for a tighter fit within the corresponding groove, channel, lock or other pathway. In yet other implementations, both the top member 1520 and the bottom member can include grooves, channels, locks or other pathways, as well as one or more protrusions 1524.

In some implementations, the sampling channel 1506 and the sequestration chamber 1508 are formed by grooves, channels, locks or other pathways formed in housing 1501. The housing 1501 can be made of any suitable material, including rubber, plastic, metal or other material. The housing 1501 can be formed of a clear or translucent material, or of an opaque or non-translucent material. In other implementations, the housing 1501 can be mostly opaque or non-translucent, while the housing surface directly adjacent to the sampling channel 1506 and/or the sequestration chamber 1508 is clear or translucent, giving a practitioner a visual cue or sign that the sequestration chamber 1508 is first filled to the extent necessary or desired, and/or then a visual cue or sign that the sequestered blood remains sequestered while a clean sample of blood is drawn through the sampling channel 1506. Other visual cues or signs of the sequestration can include, without limitation: the air permeable blood barrier 1512 turning a different color upon contact, saturation, or partial saturation with blood; a color-coded tab or indicator at any point along or adjacent to the sequestration chamber; an audible signal; a vibratory signal; or other signal.

After a venipuncture by a patient needle of a patient (not shown), which could gather a number of pathogens from the patient's skin, a first amount of the patient's blood with those pathogens will make its way into the inlet port 1502 blood sequestration device 1500 and flow into the sequestration chamber 1508 by following the path of least resistance, as the patient's own blood pressure overcomes the atmospheric pressure in the sequestration chamber 1508 to displace air therein through the air permeable blood barrier 1512. The patient's blood pressure will not be sufficient to overcome the air pressure that builds up in the sealed sampling channel 1506. Eventually, the sequestration chamber 1508, which has a predetermined volume, is filled with blood that displaces air through the air permeable blood barrier 1512. Once the blood hits the air permeable blood barrier, the blood interacts with the air permeable blood barrier 1512 material to completely or partially seal the vent 1510. A signal or indication may be provided that the practitioner can now utilize the Vacutainer capsule or other blood sample collection device to acquire a next amount of the patient's blood for sampling. The blood in the sequestration chamber 1508 is now effectively sequestered in the sequestration chamber.

Upon filling the blood sequestration pathway 1508 but prior to use of the Vacutainer or other blood sample collection device, the patient's blood pressure may drive compression of the air in the sampling channel 1506, possibly resulting in a small amount of blood moving past the diversion point to the sequestration chamber 1508 and into the sampling channel 1506, queuing up the uncontaminated blood to be drawn through the sampling channel 1506.

In some instances, as shown in FIG. 15H, an inlet port 1532 can include a male luer connector for connecting to a removable patient needle, and an outlet port 11534 can include a female luer connector for connecting with a syringe. This implementation of the inlet port and outlet port can be used with any device described herein, for avoiding a propensity of a Vacutainer-type device collapsing a patient's vein. In this implementation, a clinician can use the syringe in a modulated fashion to obtain a blood sample. In operation, the syringe is attached to the outlet port 1004, and the needle is attached to the inlet port 1002. A venipuncture is performed with the needle, and without the clinician pulling on the syringe. An initial aliquot of blood fills a sequestration chamber, and then the syringe can be used to draw a sample of blood through the collection channel, bypassing the sequestered blood in the sequestration chamber.

FIGS. 16-19 illustrate yet another implementation of a blood sequestration device. FIGS. 16A-16D illustrate a blood sequestration device 1600 that can be connected between a blood sample collection device, such as an evacuated blood collection container like a Vacutainer™ (not shown), and a patient needle (not shown) and/or associated tubing. FIG. 17 illustrates a bottom member of the blood sequestration device, and FIG. 18 illustrates a top member of the blood sequestration device, which top member and bottom member can be mated together to form an inlet port, and outlet port, a sequestration chamber and a sampling channel, as explained more fully below. FIGS. 19A and B show the top member and bottom member mated together. It should be understood that FIGS. 16-19 illustrate one exemplary manner of constructing a blood sequestration device as described herein, and other forms of construction are possible.

Referring to FIGS. 16A-D, the blood sequestration device 1600 includes an inlet port 1602 that can be connected with a patient needle that is inserted into a patient's vascular system for access to and withdrawing of a blood sample. The inlet port 1602 may also be connected with tubing or other conduit that is in turn connected with the patient needle. The inlet port 1602 defines an opening into the blood sequestration device 1600, which opening can be the same cross sectional dimensions as tubing or other conduit connected with the patient needle or the patient needle itself. For instance, the opening can be circular with a diameter of approximately 0.045 inches, but can have a diameter of between 0.01 inches or less to 0.2 inches or more.

The inlet port 1602 can also include a sealing or fluid-tight connector or connection, such as threading or Luer fitting, or the like. In some implementations, tubing or other conduit associated with the patient needle can be integral with the inlet port 1602, such as by co-molding, gluing, laser weld, or thermally bonding the parts together. In this manner, the blood sequestration device 1600 can be fabricated and sold with the patient needle and/or tubing as a single unit, eliminating the need for connecting the patient needle to the blood sequestration device 1600 at the time of blood draw or sampling.

The blood sequestration device 1600 further includes an outlet port 1604, which defines an opening out of the blood sequestration device 1600 and to the blood sample collection device. The outlet port 1604 may also be connected with tubing or other conduit that is in turn connected with the blood sequestration device, and may also include a sealing or fluid-tight connector or connection, such as threading or Luer fitting, or the like. Accordingly, as discussed above, the blood sequestration device 1600 can be fabricated and sold with the patient needle and/or tubing and the blood sample collection device as a single unit, eliminating the need for connecting the patient needle and the blood sample collection device to the blood sequestration device 1600 at the time of blood draw or sampling.

The blood sequestration device 1600 further includes a sampling channel 1606 between the inlet port 1602 and the outlet port 1604, and a sequestration chamber 1608 that is connected to and split off or diverted from the sampling channel 1606 at any point between the inlet port 1602 and the outlet port 1604. The sampling channel 1606 functions as a blood sampling pathway once a first aliquot of blood has been sequestered in the sequestration chamber 1608. The sampling channel 1606 can be any sized, shaped or configured channel, or conduit. In some implementations, the sampling channel 1606 has a substantially similar cross sectional area as the opening of the inlet port 1602. In other implementations, the sampling channel 1606 can gradually widen from the inlet port 1602 to the outlet port 1604. The sequestration chamber 1608 may have a larger cross section to form a big reservoir toward the sequestration channel path so that the blood will want to enter the reservoir first versus entering a smaller diameter on the sampling channel 1606, as is shown more fully in FIGS. 17 and 19.

Figure 17B:
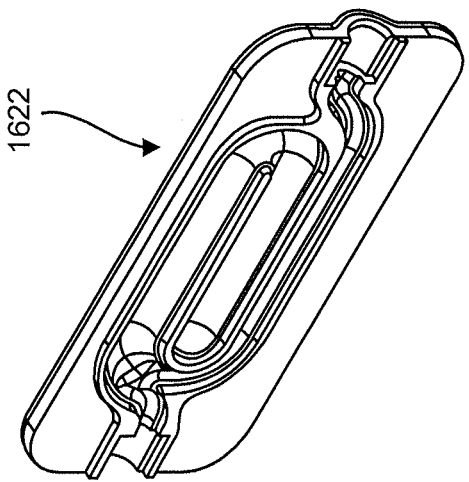
FIGS. 17A-17E illustrate a bottom member of a housing for a blood sequestration device.
Figure 17E:
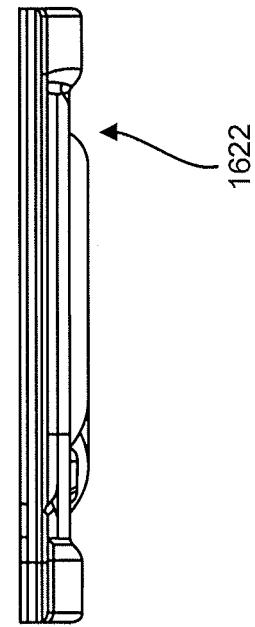
Figure 17D:
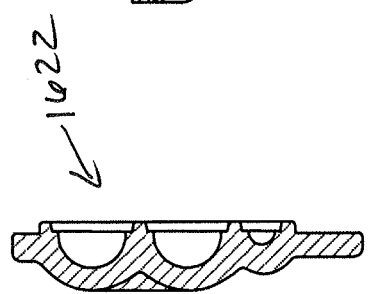
Figure 17A:
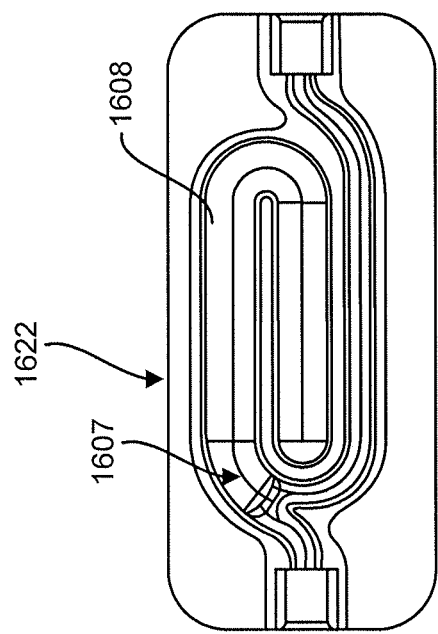
Figure 17C:
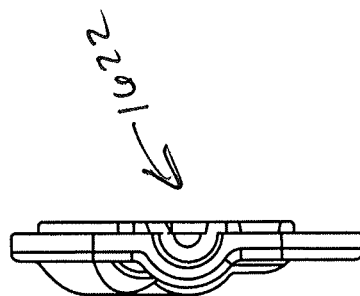
Figure 18C:
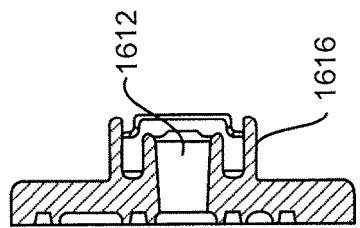
FIGS. 18A-18F illustrate a top member of a housing for a blood sequestration device.
Figure 18F:
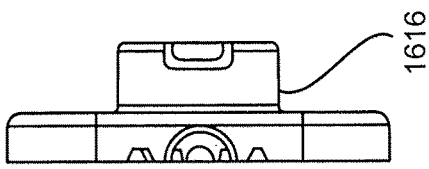
Figure 18B:
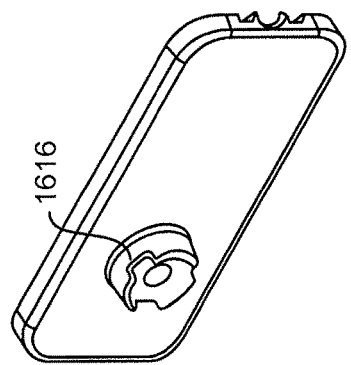
Figure 18E:
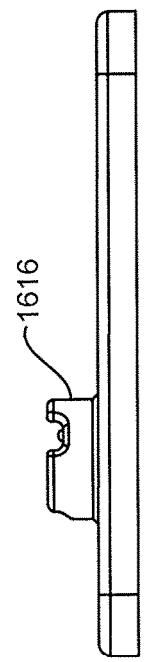
Figure 18A:
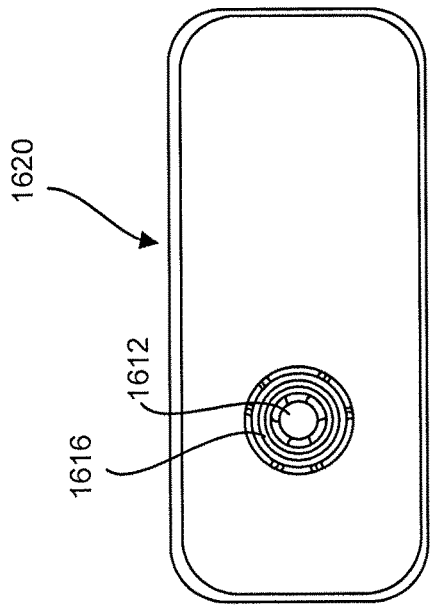
Figure 18D:
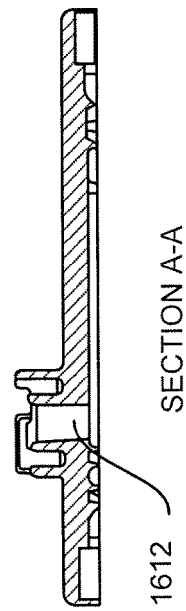

In some exemplary implementations, the diversion between the sampling channel 1606 and the sequestration chamber 1608 is by diverter junction 1607. Diverter junction 1607 may be a substantially Y-shaped, T-shaped, or U-shaped. In some preferred exemplary implementations, and as shown in FIG. 17A-17B, the diverter junction 1607 is configured such that the flow out of the inlet port 1602 is preferentially directed toward the sequestration chamber 1608. The sequestration chamber 1608 may also include or form a curve or ramp to direct the initial blood flow toward and into the sequestration chamber 1608.

The sequestration chamber 1608 is preferably maintained at atmospheric pressure, and includes a vent 1610 at or near a distal end of the sequestration chamber 1608. The vent 1610 may include an air permeable blood barrier 1612 as described above.

The blood sequestration device 1600 can include a housing 1601 that can be formed of multiple parts or a single, unitary part. In some implementations, and as illustrated in FIGS. 17A-17E and FIGS. 18A-18F, the housing 1601 includes a top member 1620 and a bottom member 1622 that are mated together. The blood sequestration device 1600 can also include a gasket or other sealing member (not shown) so that when the top member 1620 is mechanically attached with the bottom member 1622, the interface between the two is sealed by the gasket or sealing member. The FIGS. 17A-17E illustrate a bottom member 1622 of a housing for a blood sequestration device 1600. The bottom member 1622 can include grooves, channels, locks, conduits or other pathways pre-formed therein, such as by an injection molding process or by etching, cutting, drilling, etc., to form the sampling channel 1606, the sequestration chamber 1608, and diverter junction 1607.

The sequestration chamber 1608 may have a larger cross section than the sampling channel 1606 so that the blood will preferentially move into the sequestration chamber first versus entering a smaller diameter on the sampling channel 1606.

FIGS. 18A-18F illustrate the top member 1620, which can be connected with the bottom member 1622 by any mating or connection mechanism, such as by laser welding, thermal bonding, gluing, using screws, rivets, bolts, or the like, or by other mating mechanisms such as latches, grooves, tongues, pins, flanges, or the like. The top member 1620 can include some or all of the grooves, channels, locks, conduits or other pathways to form the sampling channel 1606, the sequestration chamber 1608, and the diverter junction 1607. In yet other implementations, both the top member 1620 and the bottom member 1622 can include the grooves, channels, locks or other pathways.

In some implementations, the sampling channel 1606 and the sequestration chamber 1608 are formed by grooves, channels, locks or other pathways formed in housing 1601. The housing 1601 can be made of rubber, plastic, metal or any other suitable material. The housing 1601 can be formed of a clear or translucent material, or of an opaque or non-translucent material. In other implementations, the housing 1601 can be mostly opaque or non-translucent, while the housing surface directly adjacent to the sampling channel 1606 and/or the sequestration chamber 1608 may be clear or translucent, giving a practitioner a visual cue or sign that the sequestration chamber 1608 is first filled to the extent necessary or desired, and/or then a visual cue or sign that the sequestered blood remains sequestered while a clean sample of blood is drawn through the sampling channel 1606. Other visual cues or signs of the sequestration can include, without limitation: the air permeable blood barrier 1612 turning a different color upon contact, saturation, or partial saturation with blood; a color-coded tab or indicator at any point along or adjacent to the sequestration chamber; an audible signal; a vibratory signal; or other signal.

As shown in FIGS. 18A-18F, the air permeable blood barrier 1612 can be covered with, or surrounded by, a protective member 1616. The protective member 1616 can be sized and configured to inhibit a user from touching the air permeable blood barrier 1612 with their finger or other external implement, while still allowing air to exit the air permeable blood barrier 1612 as the air is displaced from the sequestration chamber 1608. In some implementations, the protective member 1616 includes a protrusion that extends up from a top surface of the top member 1620 and around the air permeable blood barrier 1612. The protective member 1616 can be constructed to inhibit or prevent accidental exposure of the filter to environmental fluids or splashes. This can be accomplished in a variety of mechanical ways including but not limited to the addition of a hydrophobic membrane to the protective cover.

In use, the blood sequestration device 1600 includes a sampling channel 1606 and a sequestration chamber 1608. Both pathways are initially air-filled at atmospheric pressure, but the sampling channel 1606 is directed to an outlet port 1604 that will be initially sealed by a Vacutainer or other such sealed blood sampling device, and the sequestration chamber 1608 terminates at a vent 1610 to atmosphere that includes an air permeable blood barrier 1612.

After a venipuncture by a patient needle of a patient (not shown), which could gather a number of pathogens from the patient's skin, a first amount of the patient's blood with those pathogens will pass through inlet port 1602 of blood sequestration device 1600. This initial volume of potentially contaminated blood will preferentially flow into the sequestration chamber 1608 by finding the path of least resistance. The patient's own blood pressure overcomes the atmospheric pressure in the vented sequestration chamber 1608 to displace air therein through the air permeable blood barrier 1612, but is not sufficient to overcome the air pressure that builds up in the sealed sampling channel 1606. In various exemplary embodiments, the sequestration chamber 1608 and sampling channel 1606 can be configured such that the force generated by the patient's blood pressure is sufficient to overcome any effect of gravity, regardless of the blood sequestration device's orientation.

Eventually, the sequestration chamber 1608 fills with blood that displaces air through the air permeable blood barrier 1612. Once the blood contacts the air permeable blood barrier, the blood interacts with the air permeable blood barrier 1612 material to completely or partially seal the vent 1610. A signal or indication may be provided that the practitioner can now utilize the Vacutainer or other blood sampling device.

Upon filling the blood sequestration pathway 1608 but prior to use of the Vacutainer or other blood sample collection device, the patient's blood pressure may drive compression of the air in the sampling channel 1606, possibly resulting in a small amount of blood moving past the diversion point into the sampling channel 1606, queuing up the uncontaminated blood to be drawn through the sampling channel 1606.

Figure 19A:
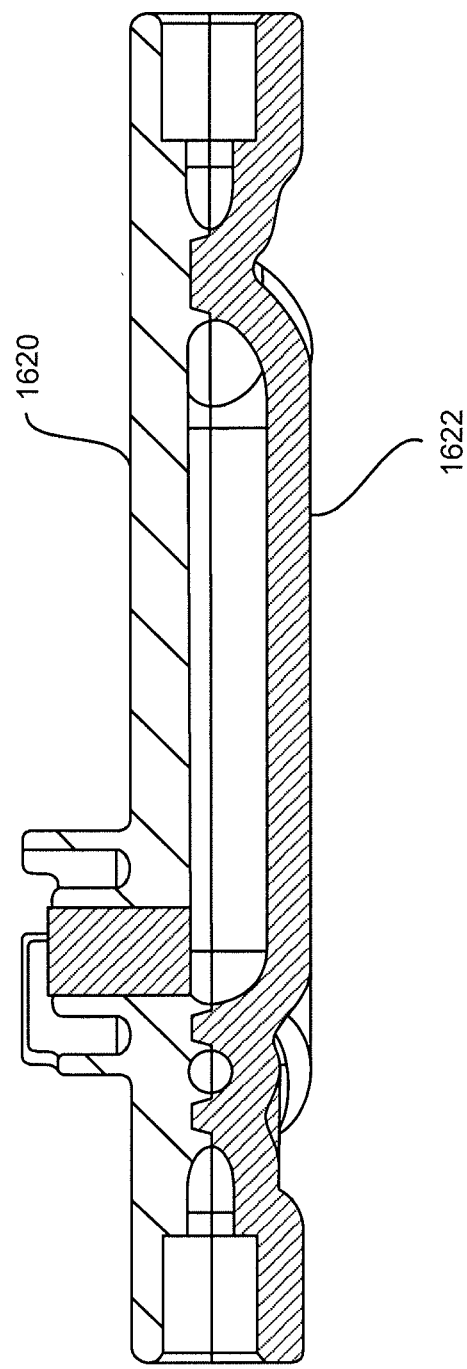
FIGS. 19A and 19B illustrate a blood sequestration device having a top member mated with a bottom member.
Figure 19B:
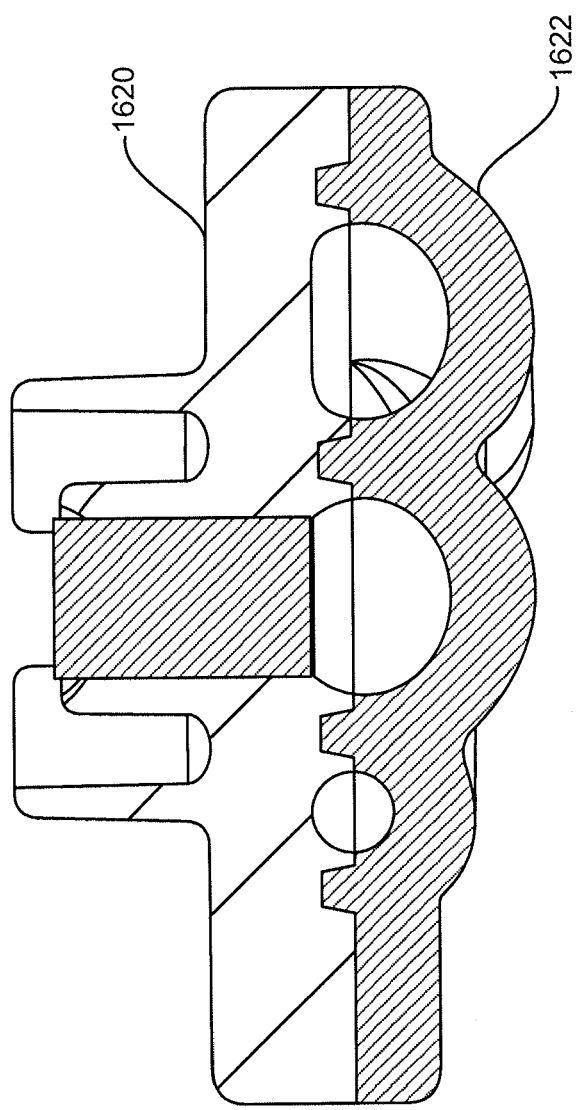

FIG. 19A is a side view, and FIG. 19B is a cross-sectional view, of the blood sequestration device 1600, illustrating the top member 1620 mated with the bottom member 1622.

Figure 20:
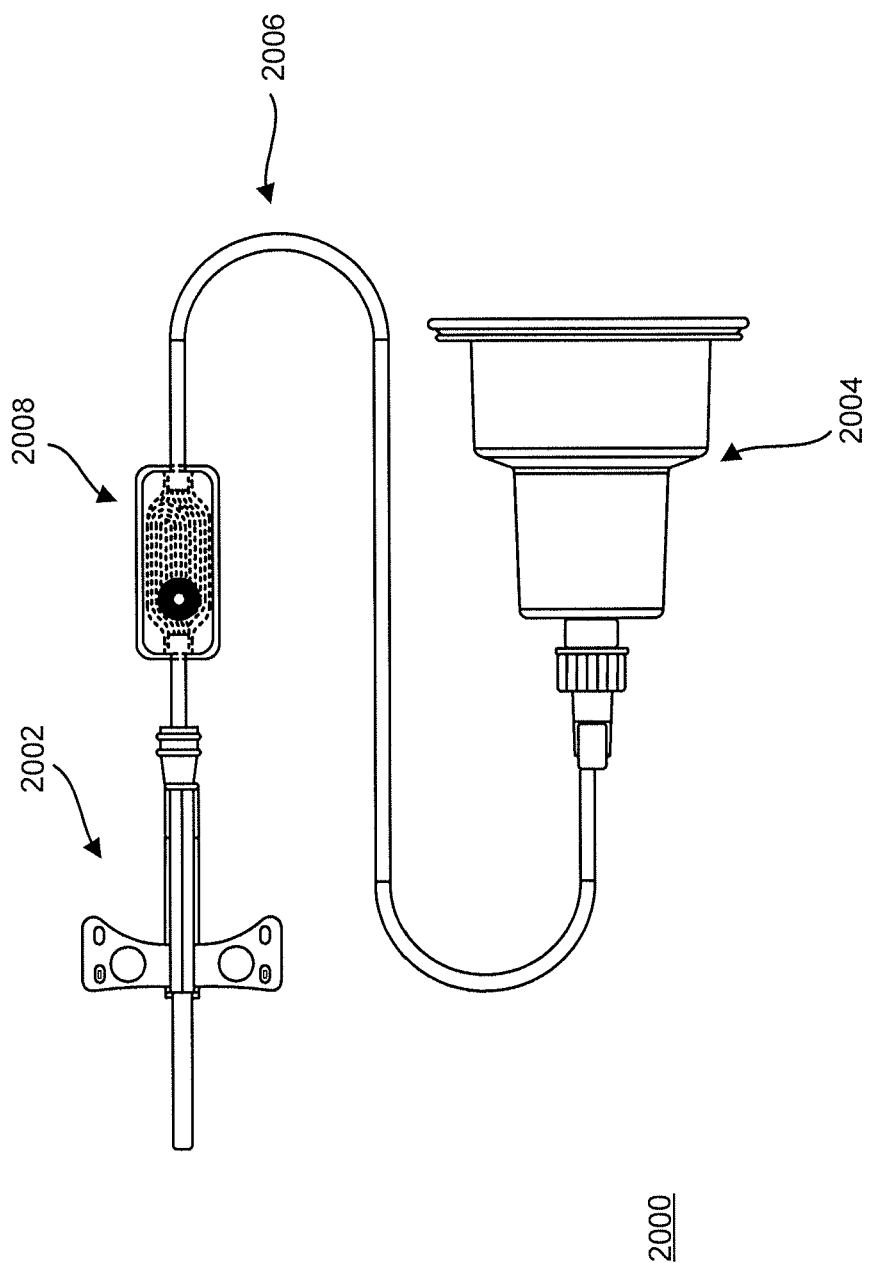
FIG. 20 shows a blood sample optimization system including a blood sequestration device.

FIG. 20 shows a blood sample optimization system 2000 that includes a patient needle 2002 for vascular access to a patient's bloodstream, a blood sample collection device 2004 to facilitate the collecting of one or more blood samples, and a conduit 2006 providing a fluid connection between the patient needle 2002 and the blood sample collection device 2004. In some implementations, the blood sample collection device 2004 includes a protective shield that includes a sealed collection needle on which a sealed vacuum-loaded container is placed, which, once pierced by the collection needle, draws in a blood sample under vacuum pressure or force through the conduit 2006 from the patient needle 2002.

The blood sample optimization system 2000 further includes a blood sequestration device 2008, located at any point on the conduit 2006 between the patient needle 2002 and the blood sample collection device 2004 as described herein.

Figure 21:
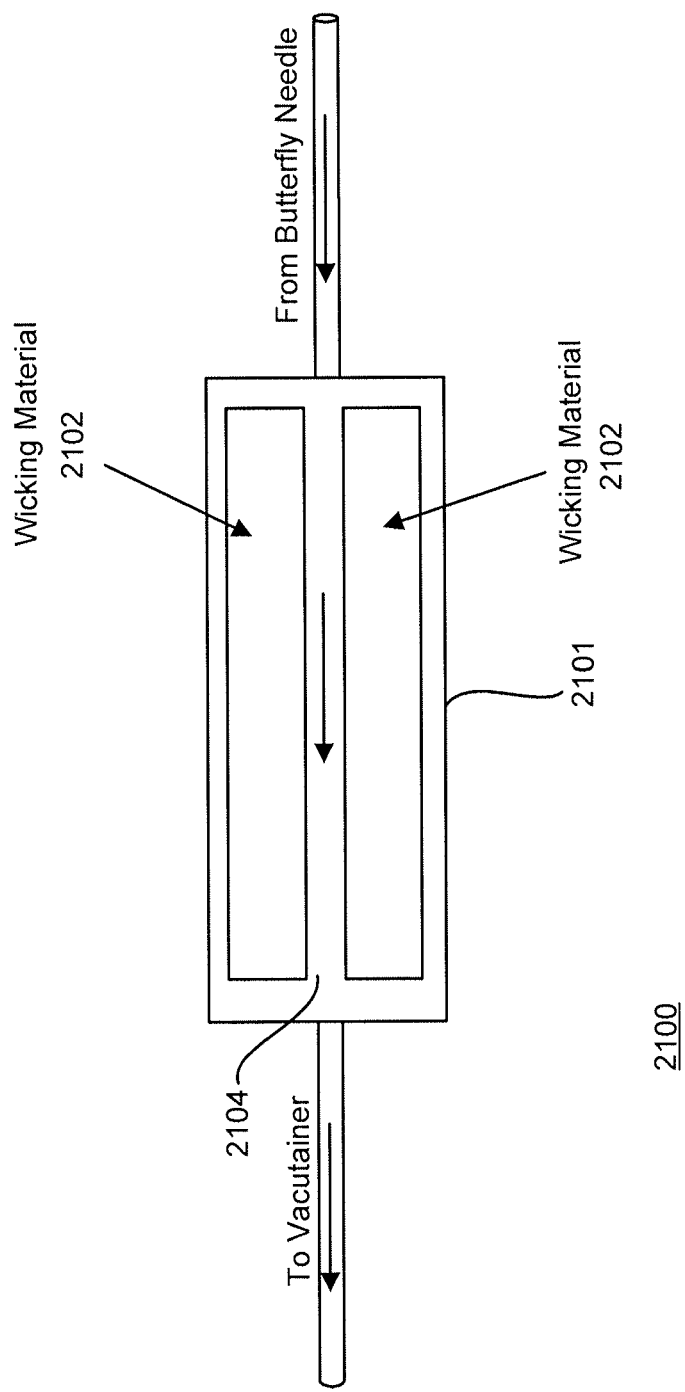
FIG. 21 illustrates a non-vented blood sequestration device using a wicking material chamber.

FIG. 21 illustrates a non-vented blood sequestration device 2100 using a wicking material chamber. The blood sequestration device 2100 includes a housing 2101 that has a sampling channel 2104 that is at least partially surrounded or abutted by a sequestration chamber 2102 that is filled with a wicking material. An initial aliquot of blood is drawn in from the patient needle into the sampling channel 2104 where it is immediately wicked into the wicking material of the sequestration chamber 2102. The wicking material and/or sequestration chamber 2102 is sized and adapted to receive and hold a predetermined amount of blood, such that follow-on or later blood draws pass by the wicking material and flow straight through the sampling channel 2104 to a sampling device such as a Vacutainer. The wicking material can include a substance such as a solidifier, a decontaminate, or other additive.

Figure 22A:
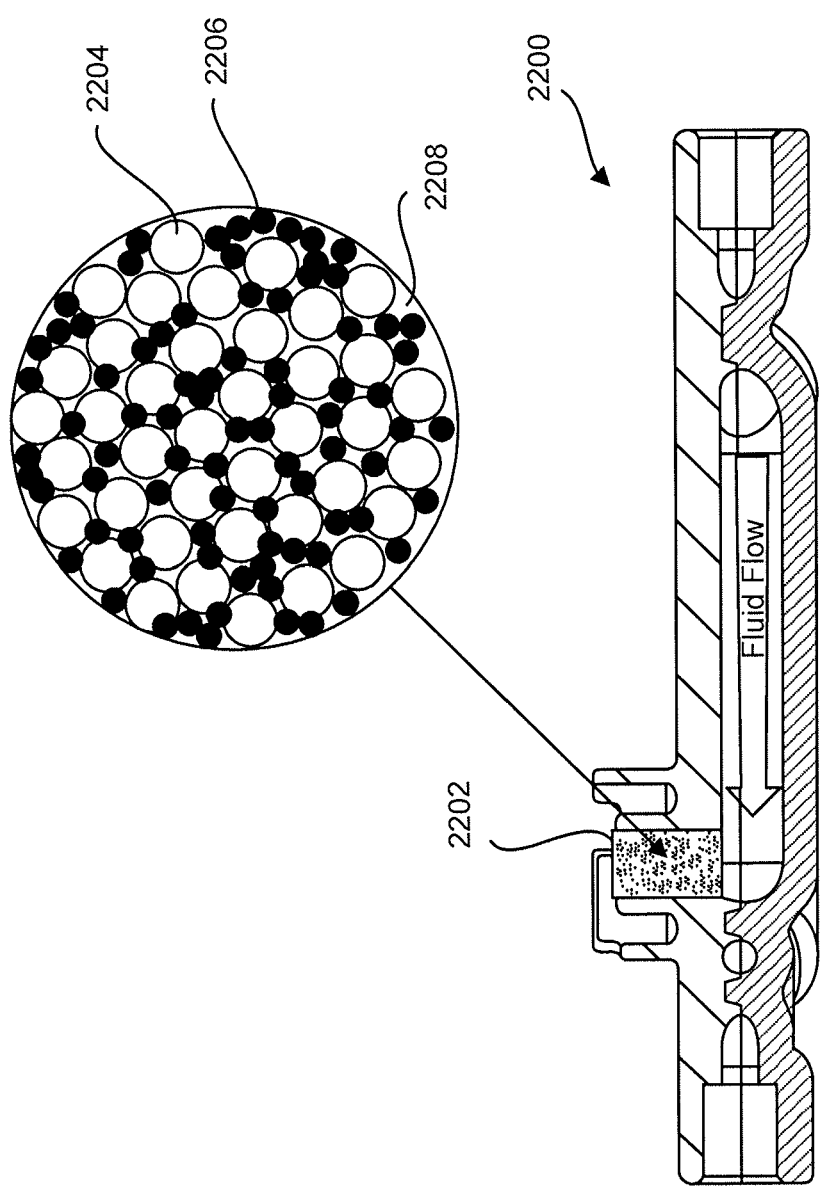
FIGS. 22A and 22B illustrate a material makeup of a filter for sequestering blood in a sequestration chamber of a blood sequestration device.
Figure 22B:
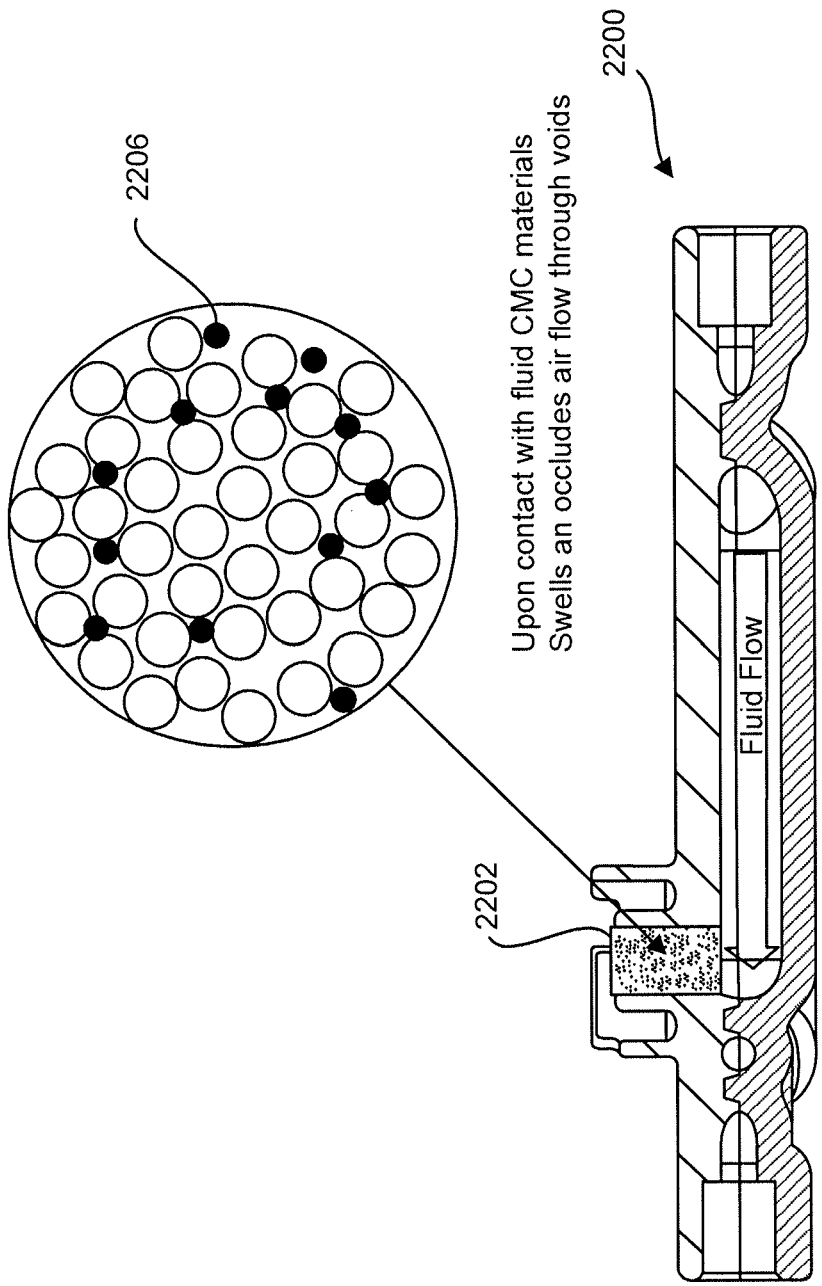

As described herein, an air permeable blood barrier may be created using a wide variety of different structures and materials. As shown in FIGS. 22A and B, an air permeable blood barrier 2202 of a blood sequestration device 2200 can include a polymer bead matrix 2204, in which at least some beads are treated to make them hydrophilic. The air permeable blood barrier 2202 further includes a self-sealing material 2206, such as carboxymethyl cellulose (CMC) or cellulose gum, or other sealing material. The air permeable blood barrier 2202 can further include voids 2208 that permit air flow before contact or during partial contact with a fluid such as blood. As shown in FIG. 22B, contact with a fluid causes the self-sealing material 2206 to swell and close off the voids 2208, occluding air flow through the voids 2208 and creating a complete or partial seal.

Figure 23A:
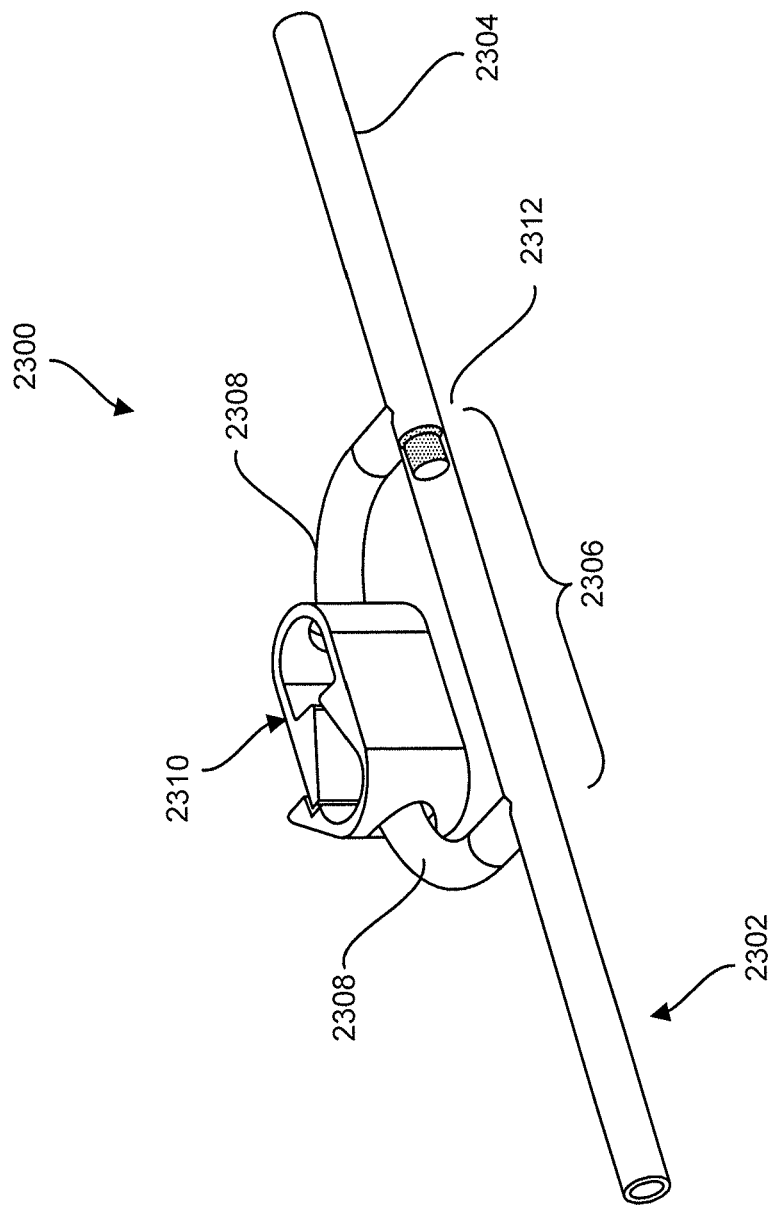
Figure 23B:
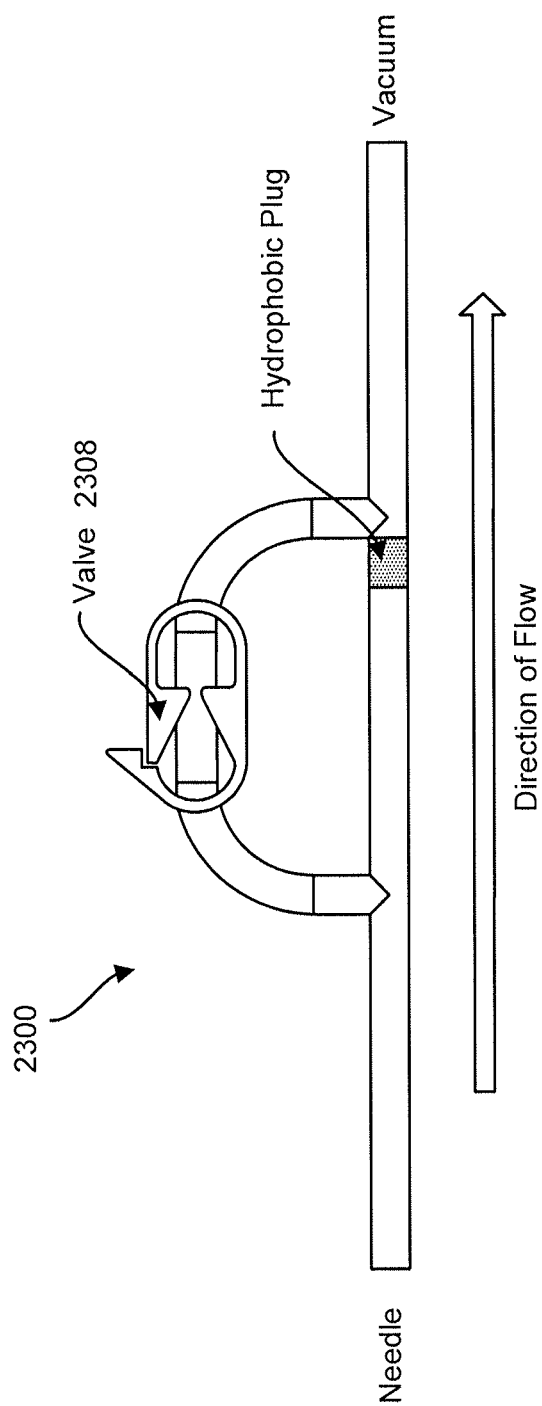
Figure 24C:
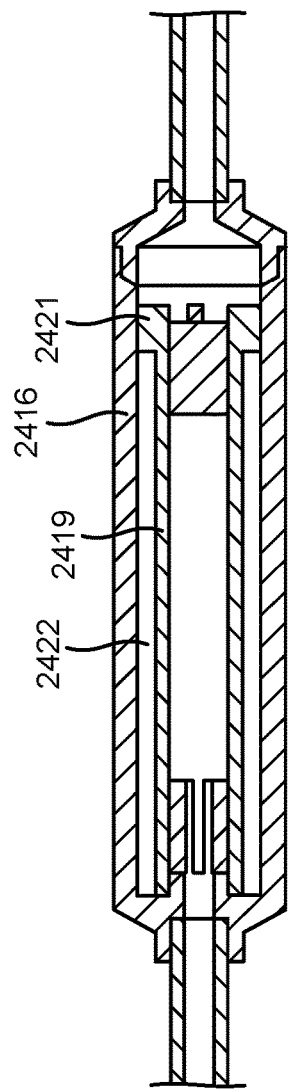
Figure 24D:
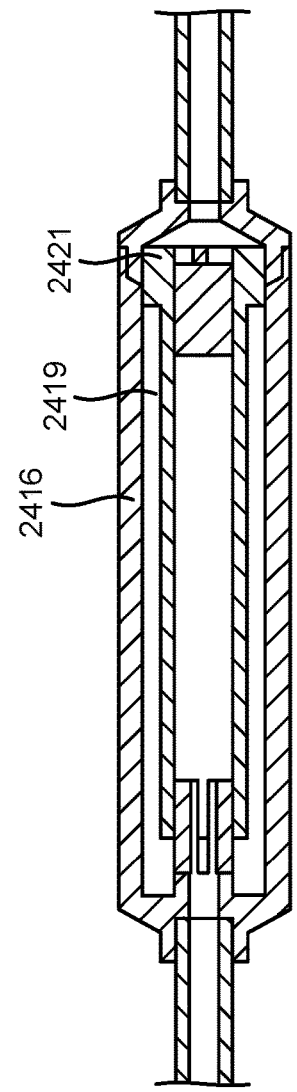
Figure 25C:
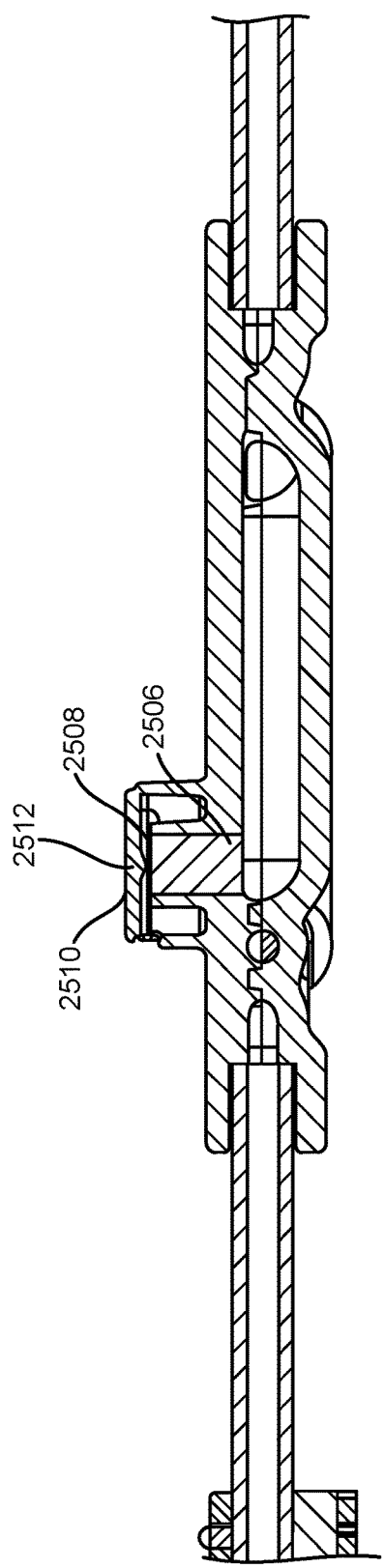
Figure 25D:
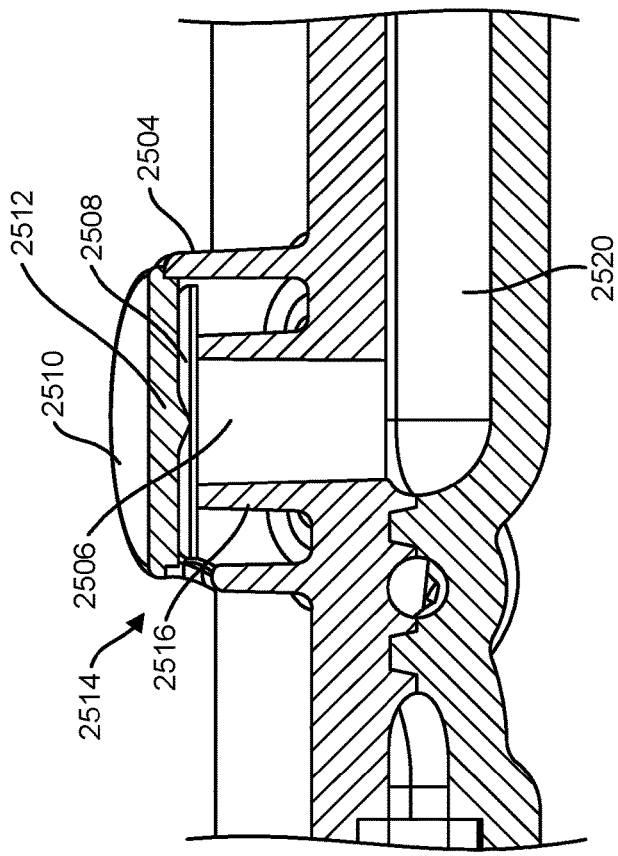

FIGS. 23A and B illustrate yet another implementation of a blood sequestration device 2300, having an inlet port 2302 to connect with a patient needle, an outlet port 2304 to connect with a blood sample collection device, a sequestration chamber 2306, and a sampling channel 2308 that bypasses the sequestration chamber 2306 once the sequestration chamber is filled to an initial aliquot of potentially contaminated blood to be sequestered. The sequestration chamber 2306 includes a hydrophobic plug 2312 at a distal end of the sequestration chamber 2306 that is farthest from the inlet port 2302. A vacuum or other drawing force applied from the outlet port 2304, such as from a Vacutainer or the like, draws in blood into the inlet port 2302 and directly into the sequestration chamber 2306, where the initial aliquot of blood will contact the hydrophobic plug 2312 and cause the initial aliquot of blood to back up into the sequestration chamber 2306 and be sequestered there. A small amount of blood may make its way into the sampling channel 2308, which is initially closed off by valve 2308. Upon release of the valve 2308, and under further force of the vacuum or other force, follow-on amounts of blood will flow into inlet port 2302, bypass the sequestration chamber 2306, and flow into and through sampling channel 2308 toward the outlet port 2304 and to the collection device.

The sampling channel 2308 can have any suitable geometry and can be formed of plastic tubing or any other suitable material. Valve 2308 can be a clip or other enclosing device to pinch, shunt, bend or otherwise close off the sampling channel 2308 before the initial aliquot of blood is sequestered in the sequestration chamber 2306. For instance, valve 2308 can also be formed as a flap, door or closable window or barrier within the sampling channel 2308.

FIGS. 23C-23E illustrate an alternative implementation of the blood sequestration device 2300', in which a sequestration chamber 2320 branches off from a main collection channel 2322 between an inlet port 2316 to connect with a patient needle and an outlet port 2318 to connect with a blood sample collection device, such as a Vacutainer, a syringe, or the like. The sequestration chamber 2320 includes an air-permeable, blood impermeable blood barrier 2324, such as a hydrophobic plug of material, or a filter formed of one or more layers, for example. A valve 2324 closes off and opens the collection channel 2322, and the device 2300' can be used similarly as described above.

FIG. 24A-24D illustrate a blood sample optimization system 2400 that includes a patient needle 2402 for vascular access to a patient's bloodstream, a blood sample collection device 2404 to facilitate the collecting of one or more blood samples for blood testing or blood cultures, and a conduit 2406 providing a fluid connection between the patient needle 2402 and the blood sample collection device 2404. In some implementations, the blood sample collection device 2404 includes a protective shield that includes a sealed collection needle on which a sealed vacuum-loaded container is placed, which, once pierced by the collection needle, draws in a blood sample under vacuum pressure or force through the conduit 2006 from the patient needle 2402.

The blood sample optimization system 2400 further includes a blood sequestration device 2408, located at any point on the conduit 2406 between the patient needle 2402 and the blood sample collection device 2404. The location of the blood sequestration device 2408 can be based on a length of the conduit between the blood sequestration device 2408 and the patient needle 2402, and the associated volume that length provides.

The blood sequestration device 2408 includes an inlet port 2412 for being connected to the conduit 2406 toward the patient needle 2402, and an outlet port 2414 for being connected to the conduit 2406 toward the blood sample collection device 2404, and a housing 2416. The housing 2416 can be any shape, although it is shown in FIGS. 24A-D as being substantially cylindrical, and includes the inlet port 2412 and outlet port 2414, which can be located anywhere on the housing although shown as being located on opposite ends of the housing 2416.

The blood sequestration device 2408 further includes a blood sequestration chamber 2418 connected with the inlet port 2412. The blood sequestration chamber 2418 is defined by an inner chamber housing 2419 that is movable from a first position to receive and sequester a first aliquot of blood, to a second position to expose one or more apertures 2424 at a proximal end of the inner chamber housing 2419 to allow blood to bypass and/or flow around the inner chamber housing 2419 and through a blood sample channel 2422 defined by the outer surface of the inner chamber housing 2419 and the inner surface of the housing 2416. The blood sequestration chamber 2418 includes an air permeable blood barrier 2420 at a distal end of the blood sequestration chamber 2418.

In operation, the inner chamber housing 2419 is in the first position toward the inlet port 2412, such that the one or more apertures 2424 are closed, and the blood sequestration chamber 2418 is in a direct path from the patient needle. Upon venipuncture of a patient, and drawing of blood by way of a syringe or Vacutainer, or other blood collection device 2404, the initial aliquot of blood flows into the blood sequestration chamber 2418. As the initial aliquot of blood flows into the blood sequestration chamber, it displaces air therein and eventually the blood contacts the blood barrier 2420, forcing the inner chamber housing to the second position. The inner chamber housing 2419 and/or housing 2416 can include a locking mechanism of one or more small tabs, grooves, detents, bumps, ridges, or the like, to maintain the inner chamber housing 2419 in the first position until the blood sequestration chamber 2418 is filled, providing force to overcome the locking mechanism to enable movement of the inner chamber housing 2419 to the second position. Once in the second position, the initial aliquot of blood is sequestered in the blood sequestration chamber 2418 and the one or more apertures 2424 are opened to create a pathway from the inlet port 2412 to the blood sampling channel 2422, bypassing and/or flowing around the blood sequestration chamber 2418.

As described above, the housing 2416 and/or inner chamber housing 2419 can be formed as cylindrical and concentric, but can be any shape, such as squared, rectangular, elliptical, oval, or other cross-sectional shape. The outer surface of the distal end of the inner chamber housing 2419 can have one or more outwardly projecting tangs 2421 with gaps therebetween. The tangs 2421 contact the inner surface of the housing 2416 to help define the blood sampling channel 2422 therebetween, and to help stop the inner chamber housing 2419 in the second position. The gaps between the tangs 2421 enable blood to flow through the blood sampling channel 2422 and to the outlet port 2414. When the inner chamber housing 2419 is in the second position and the blood sequestration chamber 2418 is filled with the first aliquot of blood, further blood samples will automatically flow through the inlet port 2412, through the one or more apertures 2424, through the blood sampling channel 2422, through the gaps between the tangs 2421, and ultimately through the outlet port 2414 to be collected by a blood sampling device 2404.

FIGS. 25A-D show a blood optimization system 2500 and blood sequestration device 2502, formed substantially as described in FIGS. 15, 16, 17, 18 and 19, but being formed to inhibit a user or other object from touching or blocking an air venting mechanism from a blood sequestration chamber 2520. Air initially in the blood sequestration chamber 2520 is displaced by an initial aliquot of blood upon venipuncture, where a patient's blood pressure overcomes the ambient air pressure in the blood sequestration chamber 2520. The air venting mechanism includes an air permeable blood barrier 2506, such as a porous material or set of materials that allows air to escape but blocks blood from leaving the blood sequestration chamber 2520.

The air venting mechanism includes an inner wall 2516 that at least partially circumscribes or surrounds the air permeable blood barrier 2506, and an outer wall 2504 spaced apart from the inner wall 2516. The outer wall 2504 can have one or more air vents 2514 formed therein. The outer wall 2504 extends higher upward than the inner wall 2516, such that a lid 2510, such as a cap, plug, cover, etc., can be attached to the outer wall 2504 and be displaced by a small distance from the top of the inner wall 2516. A seal 2508 in the form of a silicone wafer, or other elastomeric material, fits within the outer wall 2504 to cover the air permeable blood barrier 2506 and abut the top of the inner wall 2516. The seal 2508 covers and seals the air permeable blood barrier 2506 and inhibits air from entering the blood sequestration chamber 2520 through the air permeable blood barrier 2506. A fulcrum 2512 on an underside of the lid 2510 allows the seal 2508 to flexibly disconnect from the top of the inner wall 2516 when pushed by air displaced from the blood sequestration chamber 2520, to allow air to vent from the air permeable blood barrier 2506 and through the one or more air vents 2514 in the outer wall 2504.

FIG. 26A-E illustrate a blood sample optimization system 2600 that includes a patient needle 2602 for vascular access to a patient's bloodstream, a blood sample collection device 2604 to facilitate the collecting of one or more blood samples for blood testing or blood cultures, and a conduit 2606 providing a fluid connection between the patient needle 2602 and the blood sample collection device 2604. The conduit 2606 can include flexible tubing. In preferred implementations, the blood sample collection device 2604 includes a protective shield 2605 that includes a sealed collection needle on which a sealed vacuum-loaded container is placed, which, once pierced by the collection needle, draws in a blood sample under vacuum pressure or force through the conduit 2006 from the patient needle 2602.

The blood sample optimization system 2600 further includes a blood sequestration device 2608, located at any point on the conduit 2606 between the patient needle 2602 and the blood sample collection device 2604. The location of the blood sequestration device 2608 can be based on a length of the conduit between the blood sequestration device 2608 and the patient needle 2602, and the associated volume that length provides.

Figure 26E:
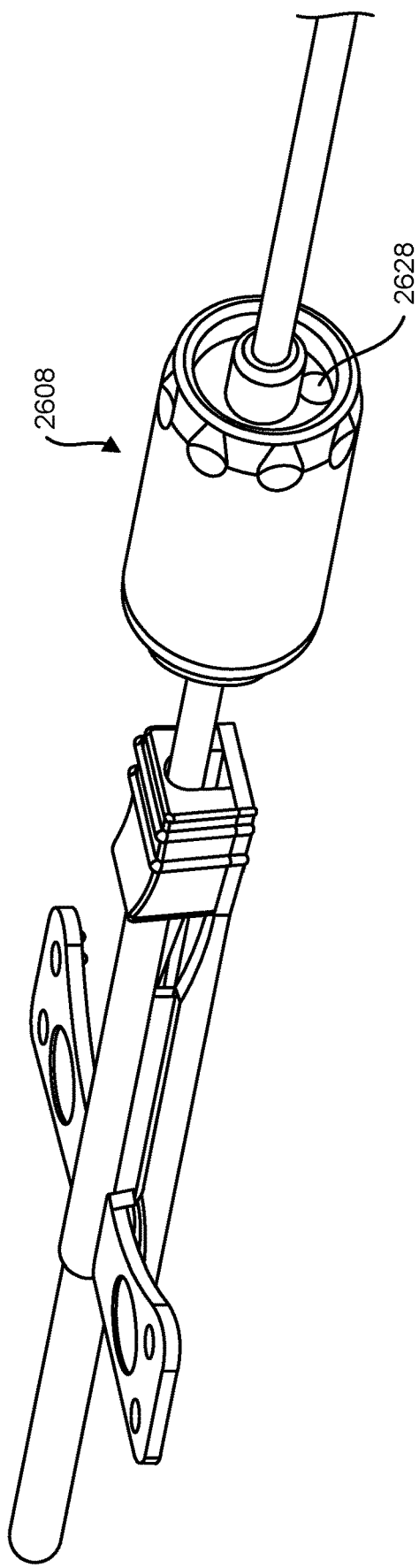

The blood sequestration device 2608 includes an inlet port 2612 for being connected to the conduit 2606 toward the patient needle 2602, and an outlet port 2614 for being connected to the conduit 2606 toward the blood sample collection device 2604. The blood sequestration device 2608 includes an outer housing 2616 and an inner housing 2617, both having a cylindrical form, and being connected concentrically. The outer housing 2616 includes an outer wall 2618 and an inner conduit 2620 that defines a blood sampling channel 2622 to convey blood through the conduit 2606 to the blood sampling device 2604. The inner housing 2617 fits snugly between the inner conduit 2620 and the outer wall 2618 of the outer housing, and is rotatable in relation to the outer housing 2616. The fit between the outer housing 2616 and the inner housing 2617 can be a friction fit that maintains the housings in a particular position. The inner housing 2617 defines a blood sequestration chamber 2624, preferably a helical or corkscrew channel around the outer surface of inner conduit 2620 of the outer housing 2616, and which terminates at an air vent 2628 having an air permeable blood barrier, as shown in FIG. 26E.

The blood sequestration chamber 2624 is connected with the blood sampling channel 2622 via diversion junction 2624 formed in the inner conduit 2620, when the blood sequestration device in a first state, illustrated in FIG. 26C. The protective shield 2606 on the collection needle 2604 provides a block for air or blood, enabling a diversion of an initial aliquot of blood into the blood sequestration chamber 2624 as the patient's blood pressure overcomes the ambient air pressure in the blood sequestration channel 2624 to displace air therefrom through air vent 2628.

When the inner housing 2617 is rotated relative to the outer housing 2616, or vice versa, to a second state, as illustrated in FIG. 26D, the blood sequestration chamber 2624 is shut off from diversion junction 2624, enabling a direct path from the patient needle through the conduit 2606 to the collection needle 2604, via blood sampling channel 2622. The outer housing 2616 and/or inner housing 2617 can include ridges or grooves formed within a portion of their surfaces, to facilitate relative rotation from the first state to the second state.

FIGS. 27A-D illustrate a blood optimization system 2700 and blood sequestration device 2702, formed substantially as described with reference to at least FIGS. 15, 16, 17, 18, 19, and 25, but being formed to inhibit a user or other object from touching or blocking an air venting mechanism from a blood sequestration chamber 2720. Air initially in the blood sequestration chamber 2720 is displaced by an initial aliquot of blood upon venipuncture, where a patient's blood pressure overcomes the ambient air pressure in the blood sequestration chamber 2720. The air venting mechanism includes an air permeable blood barrier 2706, such as a porous material or set of materials that allows air to escape but blocks blood from leaving the blood sequestration chamber 2720.

The air venting mechanism includes an inner wall 2716 that at least partially circumscribes or surrounds the air permeable blood barrier 2706, and an outer wall 2704 spaced apart from the inner wall 2716. A cap 2722 is positioned on the air venting mechanism, preferably by having a lower cap wall 2728 that fits between the inner wall 2716 and the outer wall 2704 of the air venting mechanism, and frictionally abutting either the inner wall 2716 or the outer wall 2704 or both. The cap 2722 further includes one or more vent holes 2724 or slits, apertures, openings, or the like, which extend through an upper surface of the cap 2722 around a downwardly extending plug 2726. The plug 2726 is sized and adapted to fit snugly within the space defined by inner wall 2716.

Figure 27C:
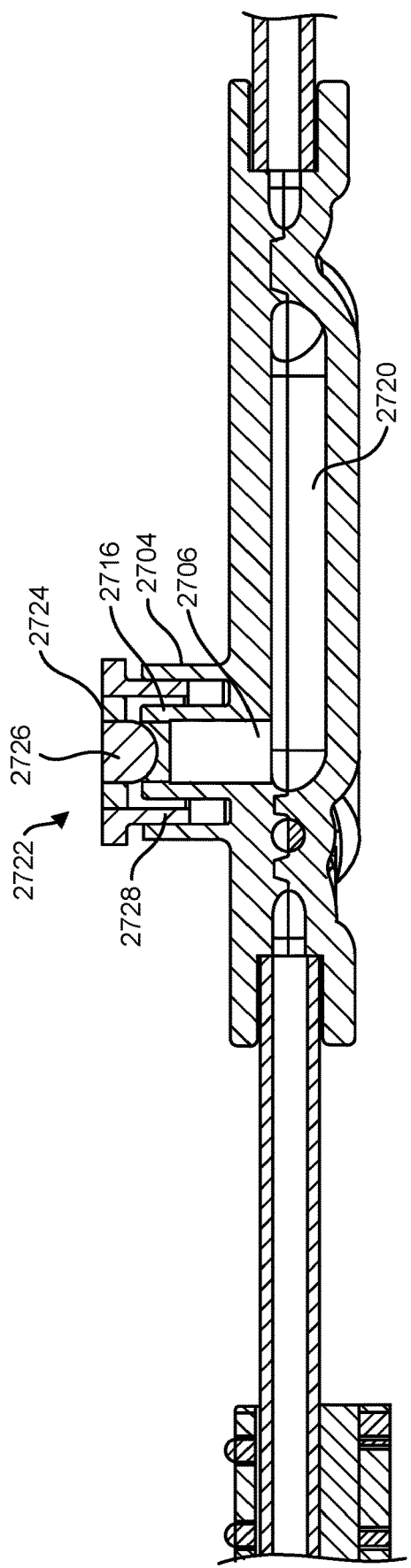
Figure 27D:
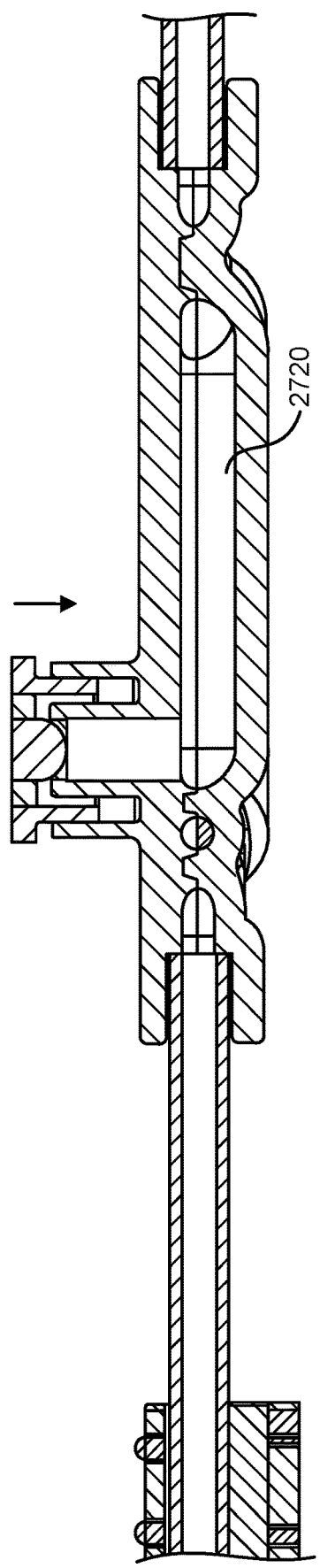

In a first position, as illustrated in FIG. 27C, the cap 2722 is extended from the air venting mechanism to allow air from the blood sequestration chamber 2720 to exit through the air permeable blood barrier 2706 and through the one or more vent holes 2724. Once the air from the blood sequestration chamber 2720 has been displaced, i.e., when the blood sequestration chamber 2720 is filled with the first aliquot of potentially tainted blood from the patient, then the cap 2722 can be pushed down on the air venting mechanism in a second position as shown in FIG. 27D, so that the plug 2726 fits within the inner wall 2716 over the air permeable blood barrier 2706 to seal the air venting mechanism. In either the first position or the second position, the cap 2722 protects the air permeable blood barrier 2706 from outside air or from being touched by a user.

Figure 28A:
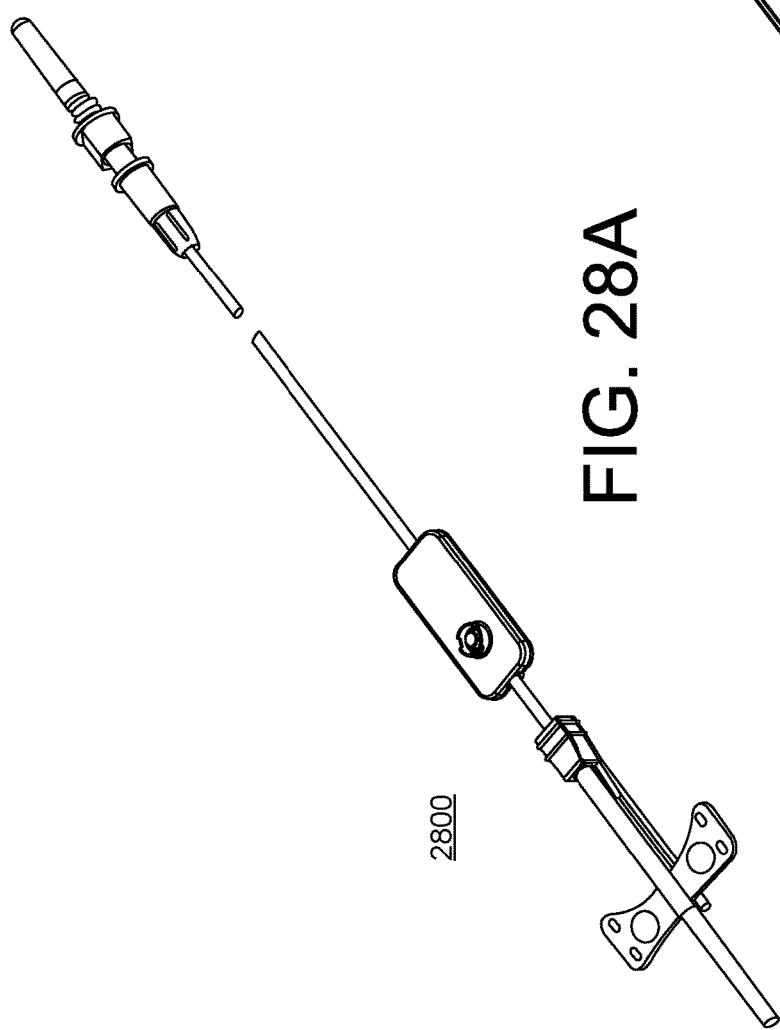
Figure 28B:
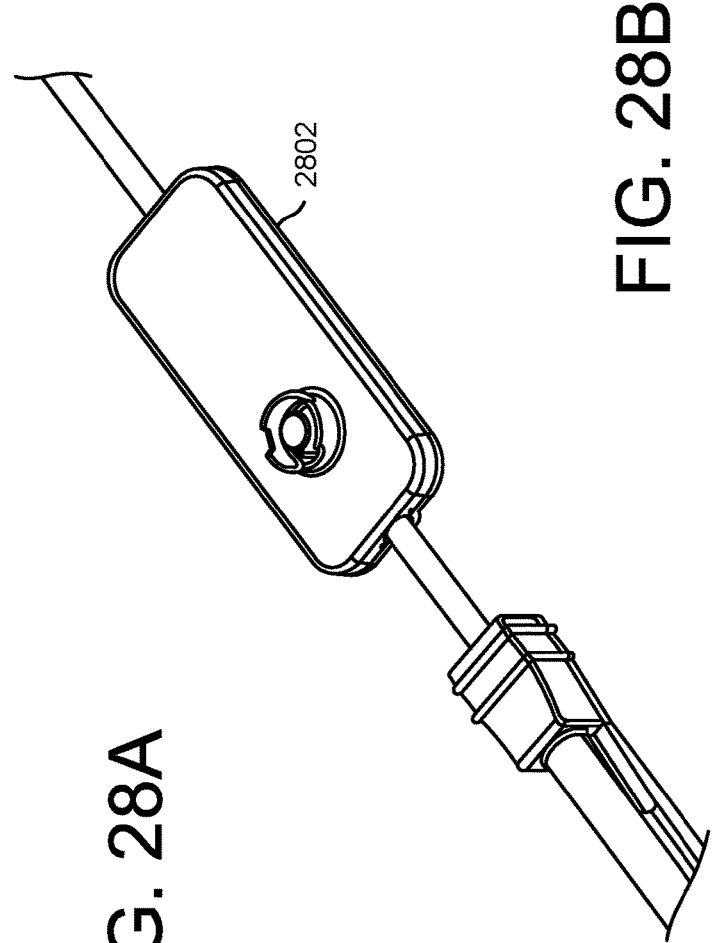
Figure 28E:
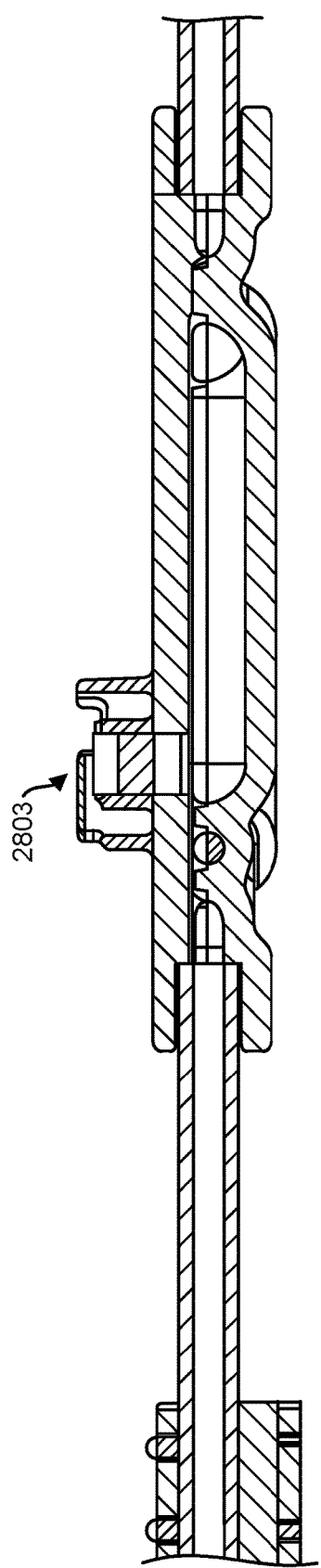
Figure 28F:
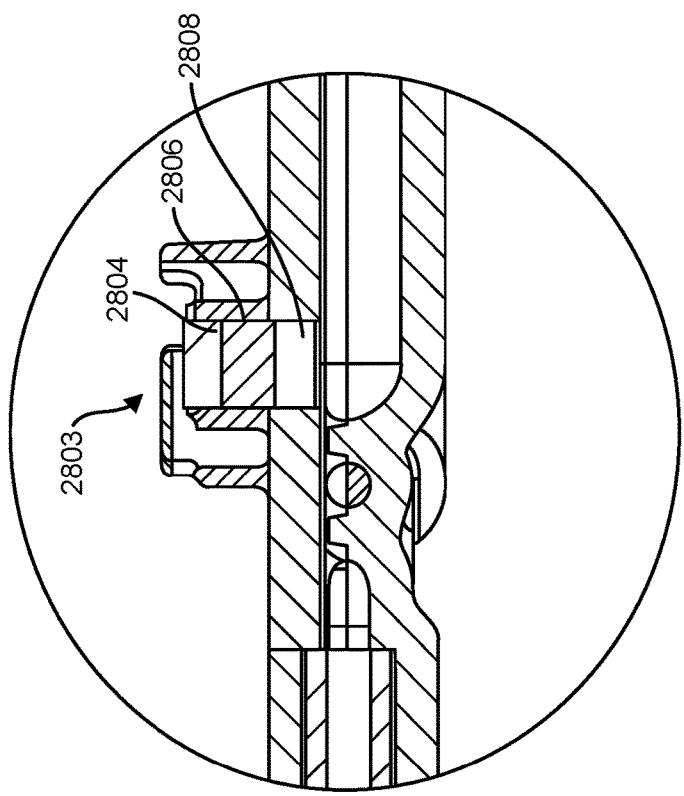

FIGS. 28A-F illustrate a blood optimization system 2800 and blood sequestration device 2802, formed substantially as described with reference to at least FIGS. 15, 16, 17, 18, 19, 25 and 26, but utilizing a multi-layered filter, and in some implementations, a filter with trapped reactive material, for an air permeable blood barrier. As shown in FIGS. 28C and D, an air permeable blood barrier 2803 includes a first layer 2804 of an air permeable but blood impermeable material, and a second layer 2806 that includes a reactive material, such as a hydrophobic material, for repelling blood while still allowing air to pass through both layers. As shown in FIGS. 28E and F, the air permeable blood barrier 2803 can include any number of layers, such as a third layer 2808 formed of the same air permeable but blood impermeable material as first layer 2804, while a second layer 2806 includes trapped or embedded blood reactive material.

Figure 29C:
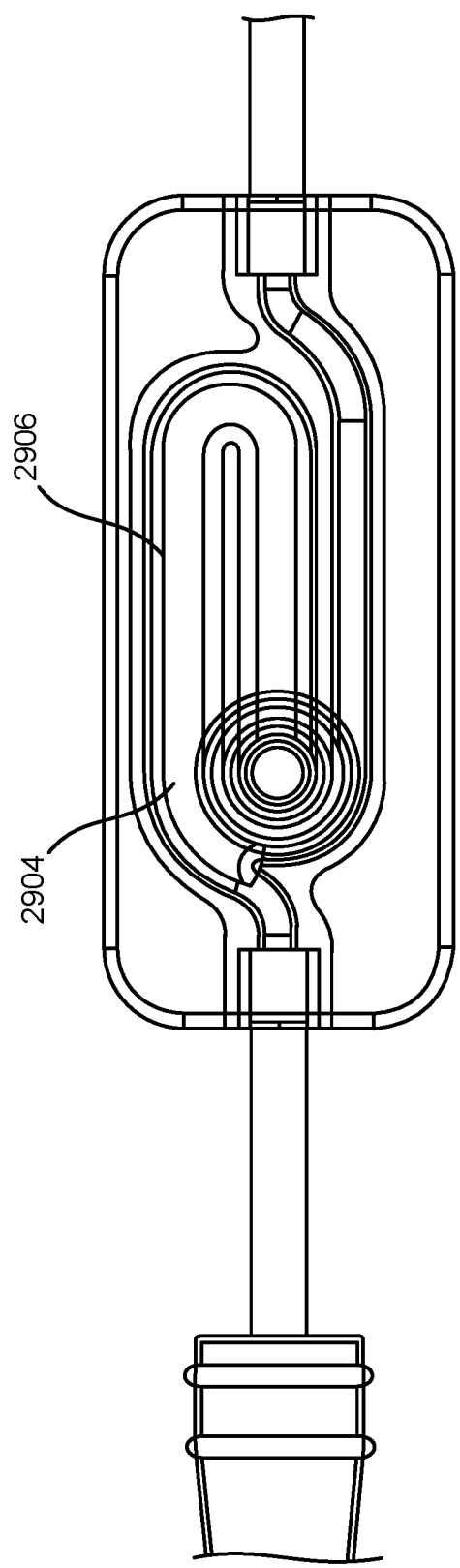
Figure 30C:
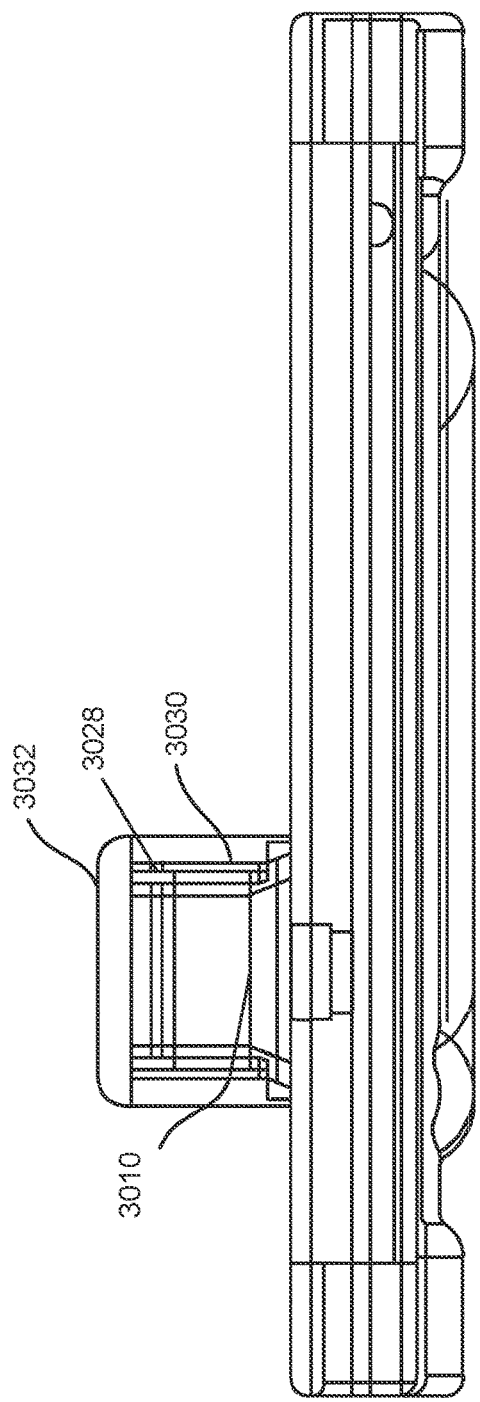
Figure 30D:
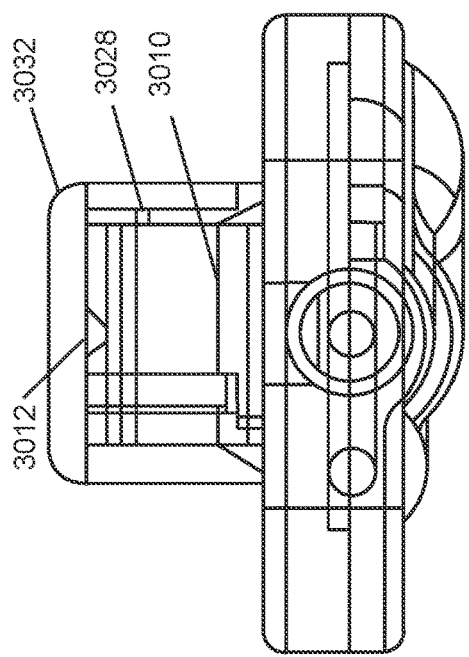
Figure 30E:
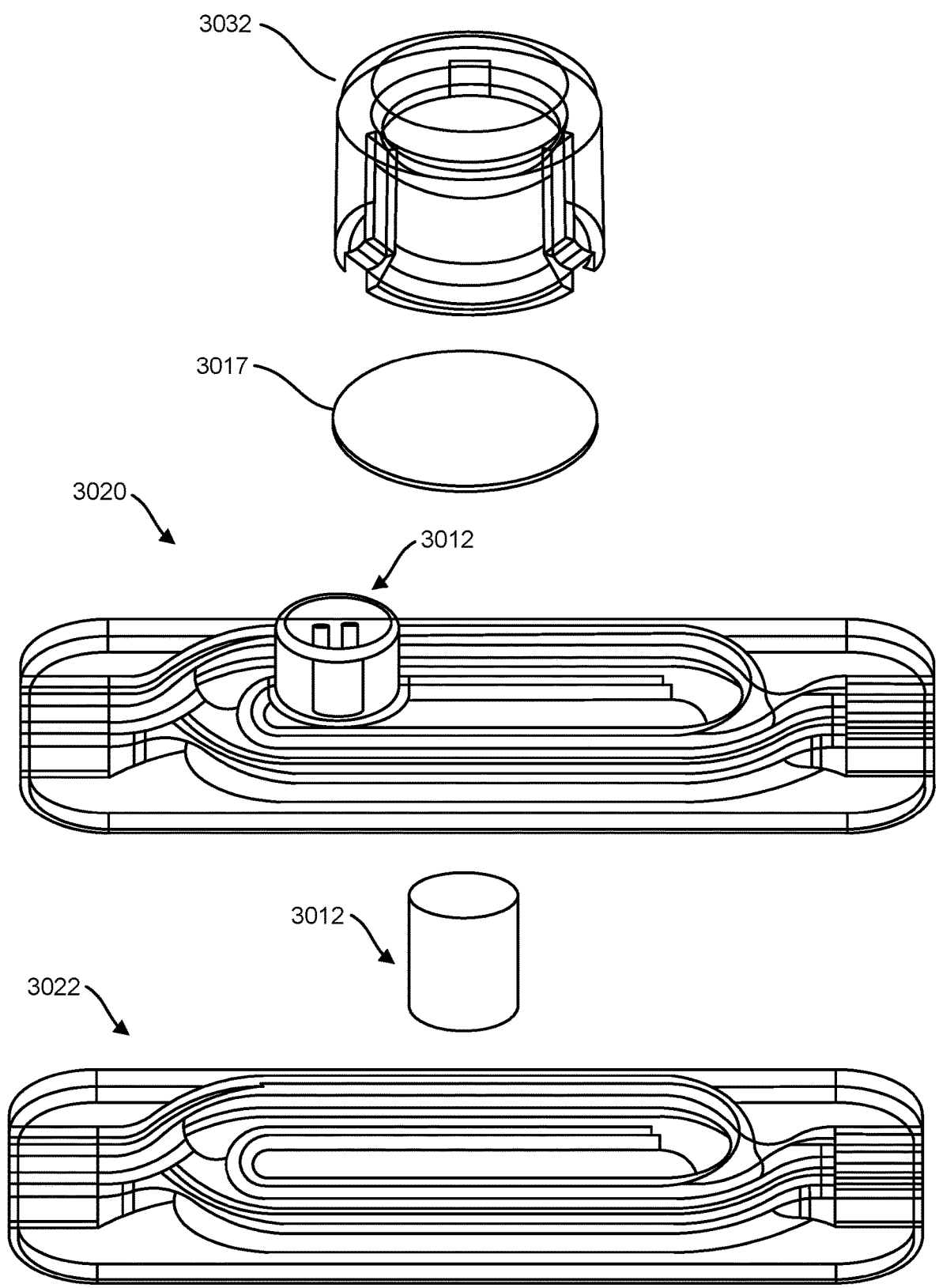
Figure 30F:
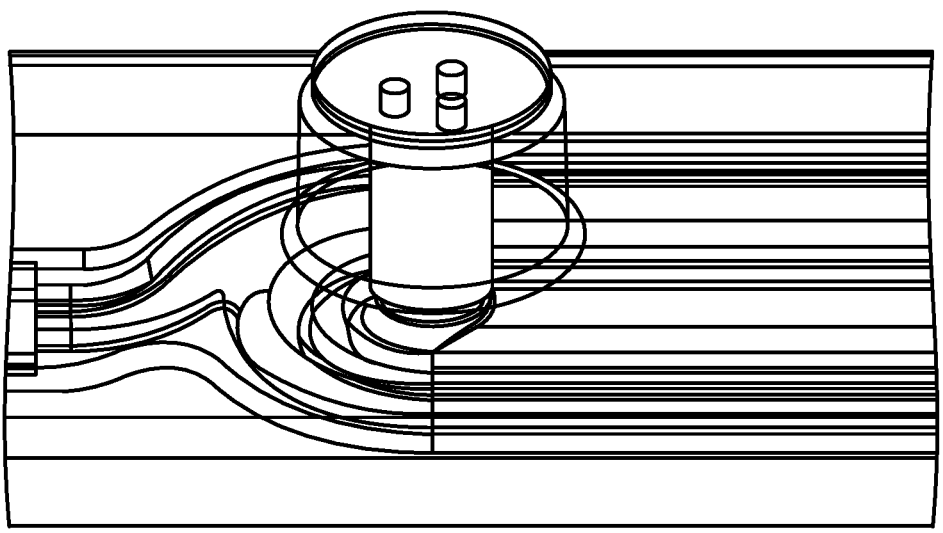
Figure 30G:
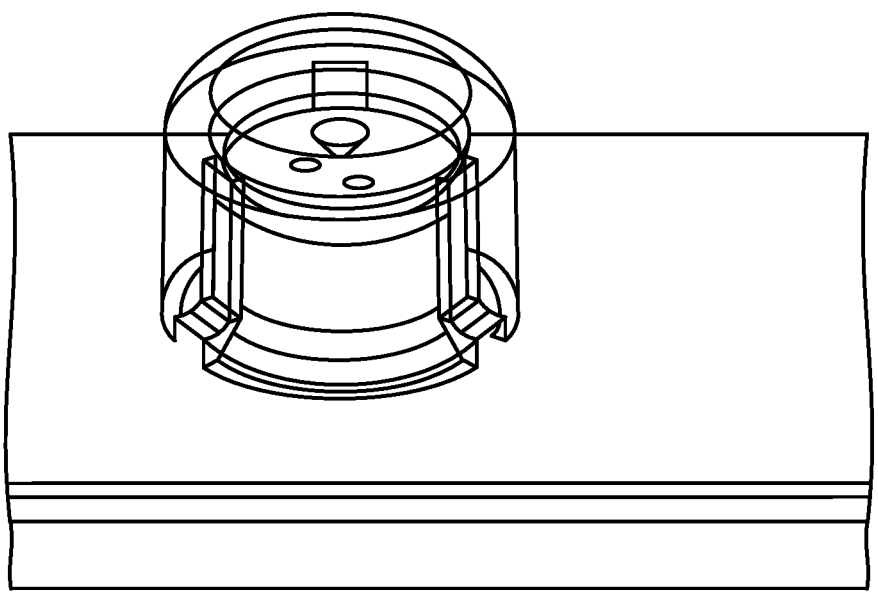

FIGS. 29A-C illustrate a blood optimization system 2900 and blood sequestration device 2902, formed substantially as described with reference to at least FIGS. 15, 16, 17, 18, 19, 25 and 26, but in which a blood sequestration chamber 2904 is at least partially filled with a blood-absorptive material 2906. The blood-absorptive material 2906 can act as a wicking material to further draw in blood to be sequestered upon venipuncture of the patient, and prior to use of a blood drawing device such as a Vacutainer™ or a syringe, or the like.

FIGS. 30A-G illustrate a blood optimization system 3000 and blood sequestration device 3002, formed substantially as described with reference to at least FIGS. 15, 16, 17, 18, 19, 25 and 26. The blood sequestration device 3000 includes an inlet port 3002 that can be connected with a patient needle that is inserted into a patient's vascular system for access to and withdrawing of a blood sample. The inlet port 3002 may also be connected with tubing or other conduit that is in turn connected with the patient needle. The inlet port 3002 defines an opening into the blood sequestration device 3000, which opening can be the same cross sectional dimensions as tubing or other conduit connected with the patient needle or the patient needle itself. For instance, the opening can be circular with a diameter of approximately 0.045 inches, but can have a diameter of between 0.01 inches or less to 0.2 inches or more.

The inlet port 3002 can also include a sealing or fluid-tight connector or connection, such as threading or Luer fitting, or the like. In some implementations, tubing or other conduit associated with the patient needle can be integral with the inlet port 3002, such as by co-molding, gluing, laser weld, or thermally bonding the parts together. In this manner, the blood sequestration device 3000 can be fabricated and sold with the patient needle and/or tubing as a single unit, eliminating the need for connecting the patient needle to the blood sequestration device 3000 at the time of blood draw or sampling.

The blood sequestration device 3000 further includes an outlet port 3004, which defines an opening out of the blood sequestration device 3000 and to the blood sample collection device. The outlet port 3004 may also be connected with tubing or other conduit that is in turn connected with the blood sequestration device, and may also include a sealing or fluid-tight connector or connection, such as threading or Luer fitting, or the like. Accordingly, as discussed above, the blood sequestration device 3000 can be fabricated and sold with the patient needle and/or tubing and the blood sample collection device as a single unit, eliminating the need for connecting the patient needle and the blood sample collection device to the blood sequestration device 3000 at the time of blood draw or sampling.

The blood sequestration device 3000 further includes a sampling channel 3006 between the inlet port 3002 and the outlet port 3004, and a sequestration chamber 3008 that is connected to and split off or diverted from the sampling channel 3006 at any point between the inlet port 3002 and the outlet port 3004. The sampling channel 3006 functions as a blood sampling pathway once a first aliquot of blood has been sequestered in the sequestration chamber 3008. The sampling channel 3006 can be any sized, shaped or configured channel, or conduit. In some implementations, the sampling channel 3006 has a substantially similar cross sectional area as the opening of the inlet port 3002. In other implementations, the sampling channel 3006 can gradually widen from the inlet port 3002 to the outlet port 3004. The sequestration chamber 3008 may have a larger cross section to form a big reservoir toward the sequestration channel path so that the blood will want to enter the reservoir first versus entering a smaller diameter on the sampling channel 3006.

In some exemplary implementations, the diversion between the sampling channel 3006 and the sequestration chamber 3008 is by diverter junction 3007. Diverter junction 3007 may be a substantially Y-shaped, T-shaped, or U-shaped. In some preferred exemplary implementations, and as shown in FIG. 17A-17B, the diverter junction 3007 is configured such that the flow out of the inlet port 3002 is preferentially directed toward the sequestration chamber 3008. The sequestration chamber 3008 may also include or form a curve or ramp to direct the initial blood flow toward and into the sequestration chamber 3008.

The sequestration chamber 3008 is preferably maintained at atmospheric pressure, and includes a vent 3010 at or near a distal end of the sequestration chamber 3008. The vent 3010 may include an air permeable blood barrier 3012 as described above.

The blood sequestration device 3000 can include a housing 3001 that can be formed of multiple parts or a single, unitary part. In some implementations, and as illustrated FIG. 30F, the housing 3001 includes a top member 3020 and a bottom member 3022 that are mated together. The blood sequestration device 3000 can also include a gasket or other sealing member (not shown) so that when the top member 3020 is mechanically attached with the bottom member 3022, the interface between the two is sealed by the gasket or sealing member. The bottom member 3022 can include grooves, channels, locks, conduits or other pathways preformed therein, such as by an injection molding process or by etching, cutting, drilling, etc., to form the sampling channel 3006, the sequestration chamber 3008, and diverter junction 3007.

The sequestration chamber 3008 may have a larger cross section than the sampling channel 3006 so that the blood will preferentially move into the sequestration chamber first versus entering a smaller diameter on the sampling channel 3006.

In some implementations, the sampling channel 3006 and the sequestration chamber 3008 are formed by grooves, channels, locks or other pathways formed in housing 3001. The housing 3001 can be made of rubber, plastic, metal or any other suitable material. The housing 3001 can be formed of a clear or translucent material, or of an opaque or non-translucent material. In other implementations, the housing 3001 can be mostly opaque or non-translucent, while the housing surface directly adjacent to the sampling channel 3006 and/or the sequestration chamber 3008 may be clear or translucent, giving a practitioner a visual cue or sign that the sequestration chamber 3008 is first filled to the extent necessary or desired, and/or then a visual cue or sign that the sequestered blood remains sequestered while a clean sample of blood is drawn through the sampling channel 3006. Other visual cues or signs of the sequestration can include, without limitation: the air permeable blood barrier 3012 turning a different color upon contact, saturation, or partial saturation with blood; a color-coded tab or indicator at any point along or adjacent to the sequestration chamber; an audible signal; a vibratory signal; or other signal.

The air permeable blood barrier 3012 can be covered with, or surrounded by, a cap 3032. The cap 3032 can be sized and configured to inhibit a user from touching the air permeable blood barrier 3012 with their finger or other external implement, while still allowing air to exit the air permeable blood barrier 3012 as the air is displaced from the sequestration chamber 3008. The cap 3032 can be constructed to inhibit or prevent accidental exposure of the filter to environmental fluids or splashes. This can be accomplished in a variety of mechanical ways including but not limited to the addition of a hydrophobic membrane to the protective cover.

The air venting mechanism includes an inner wall 3030 that at least partially circumscribes or surrounds the air permeable blood barrier 3012. The wall 3030 can have one or more air vents 3028 formed therein. The cap 3032 covers inner wall 3030 and can be snapped, glued, or otherwise attached in place. A seal 3017 in the form of a silicone wafer, or other elastomeric material, fits within the inner wall 3030 to cover the air permeable blood barrier 3012 and abut the top of the inner wall 3030. The seal 3017 covers and seals the air permeable blood barrier 3010 and inhibits air from entering the blood sequestration chamber 3008 through the air permeable blood barrier 3010. A fulcrum 3012 on an underside of the cap 3032 allows the seal 3008 to flexibly disconnect from the top of the inner wall 3016 when pushed by air displaced from the blood sequestration chamber 3008, to allow air to vent from the air permeable blood barrier 3010 and through the one or more air vents 3028 in the wall 3030 and/or cap 3032.

In use, the blood sequestration device 3000 includes a sampling channel 3006 and a sequestration chamber 3008. Both pathways are initially air-filled at atmospheric pressure, but the sampling channel 3006 is directed to an outlet port 3004 that will be initially sealed by a Vacutainer or other such sealed blood sampling device, and the sequestration chamber 3008 terminates at a vent 3010 to atmosphere that includes an air permeable blood barrier 3012.

After a venipuncture by a patient needle of a patient (not shown), which could gather a number of pathogens from the patient's skin, a first amount of the patient's blood with those pathogens will pass through inlet port 3002 of blood sequestration device 3000. This initial volume of potentially contaminated blood will preferentially flow into the sequestration chamber 3008 by finding the path of least resistance. The patient's own blood pressure overcomes the atmospheric pressure in the vented sequestration chamber 3008 to displace air therein through the air permeable blood barrier 3012, but is not sufficient to overcome the air pressure that builds up in the sealed sampling channel 3006. In various exemplary embodiments, the sequestration chamber 3008 and sampling channel 3006 can be configured such that the force generated by the patient's blood pressure is sufficient to overcome any effect of gravity, regardless of the blood sequestration device's orientation.

Eventually, the sequestration chamber 3008 fills with blood that displaces air through the air permeable blood barrier 3012. Once the blood contacts the air permeable blood barrier, the blood interacts with the air permeable blood barrier 3012 material to completely or partially seal the vent 3010. A signal or indication may be provided that the practitioner can now utilize the Vacutainer or other blood sampling device.

Upon filling the blood sequestration pathway 3008 but prior to use of the Vacutainer or other blood sample collection device, the patient's blood pressure may drive compression of the air in the sampling channel 3006, possibly resulting in a small amount of blood moving past the diversion point into the sampling channel 3006, queuing up the uncontaminated blood to be drawn through the sampling channel 3006.

In yet another aspect, the blood sequestration chamber and/or blood sampling channel, or other component, of any of the implementations described herein, can provide a visually discernable warning or result in a component adapted for operative fluid communication with the flash chamber of an introducer for an intravenous catheter into a blood vessel of a patient. The device and method provides a visually discernable alert when blood from the patient communicates with a test component reactive to communicated blood plasma, to visually change. The reaction with the blood or the plasma occurs depending on one or a plurality of reagents positioned therein configured to test for blood contents, substances or threshold high or low levels thereof, to visually change in appearance upon a result.

In yet other aspects, the blood sequestration chamber and/or blood sampling channel can be sized and adapted to provide a particular volumetric flow of blood, either during the sequestration process and/or the sampling process.

Although a variety of embodiments have been described in detail above, other modifications are possible. Other embodiments may be within the scope of the following claims.

The invention claimed is:
1. A blood sequestration device comprising;
   an inlet port;
   an outlet port;
   a sequestration chamber connected with the inlet port via a junction, the sequestration chamber having a vent that includes an air permeable blood barrier, the vent being defined by an outer wall that at least partially circumscribes the air permeable blood barrier, the vent further including a cap that at least partially covers the wall, the cap having a one-way seal abutting the air permeable blood barrier that inhibits air from entering the sequestration chamber; and
   a sampling channel having a proximal end connected with the inlet port via the junction, and a distal end connected with the outlet port;
   the sequestration chamber, the sampling channel and the junction being sized and configured such that a first portion of blood flows into the sequestration chamber toward the air permeable blood barrier for sequestration therein, and a second portion of blood bypasses the sequestration chamber and the first portion of blood sequestered therein and is directed into the sampling channel toward the outlet port.

2. The blood sequestration device in accordance with claim 1, further comprising a housing that houses and defines the inlet port, the outlet port, the sequestration chamber, and the sampling channel.

3. The blood sequestration device in accordance with claim 1, wherein the vent further includes an inner wall within the outer wall and that contains the air permeable blood barrier.

4. The blood sequestration device in accordance with claim 3, wherein the one-way seal is positioned over the inner wall and within the outer wall of the vent.

5. The blood sequestration device in accordance with claim 4, wherein the cap includes an inner surface that faces the air permeable blood barrier, the inner surface of the cap including a fulcrum against which the seal can flexibly unseal from the air permeable blood barrier to allow air to escape the sequestration chamber.

6. The blood sequestration device in accordance with claim 1, wherein the air permeable blood barrier includes a sealing material that seals the vent upon contact with blood.

7. The blood sequestration device in accordance with claim 1, wherein the air permeable blood barrier includes a filter having a first layer and a second layer, the second layer of the filter having a hydrophobic material to repel blood.

8. A blood sequestration and sampling system comprising;
   a blood sampling pathway having a patient needle on a proximal end and a sample collection device on a distal end; and
   a blood sequestration device attached on the blood sampling pathway between the proximal end and distal end of the blood sampling pathway, the blood sequestration device comprising:
      an inlet port coupled with the blood sampling pathway toward the patient needle;
      an outlet port coupled with the blood sampling pathway toward the sample collection device;
      a sequestration chamber connected with the inlet port via a junction, the sequestration chamber having a vent that includes an air permeable blood barrier, the vent being defined by an outer wall that at least partially circumscribes the air permeable blood barrier, the vent further including a cap that at least partially covers the wall, the cap having a one-way seal abutting the air permeable blood barrier that inhibits air from entering the sequestration chamber; and
      a sampling channel having a proximal end connected with the inlet port via the junction, and a distal end connected with the outlet port;
      the sequestration chamber, the sampling channel and the junction being sized and configured such that a first portion of blood flows into the sequestration chamber toward the air permeable blood barrier for sequestration therein, and a second portion of blood bypasses the sequestration chamber and the first portion of blood sequestered therein and is directed into the sampling channel toward the outlet port.

9. The blood sequestration system in accordance with claim 8, wherein the blood sequestration device further comprises a housing that houses and defines the inlet port, the outlet port, the sequestration chamber, and the sampling channel.

10. The blood sequestration system in accordance with claim 8, wherein the vent of the blood sequestration device further includes an inner wall within the outer wall and that contains the air permeable blood barrier.

11. The blood sequestration system in accordance with claim 10, wherein the one-way seal of the vent is positioned over the inner wall and within the outer wall of the vent.

12. The blood sequestration system in accordance with claim 11, wherein the cap includes an inner surface that faces the air permeable blood barrier, the inner surface of the cap including a fulcrum against which the seal can flexibly unseal from the air permeable blood barrier to allow air to escape the sequestration chamber.

13. The blood sequestration system in accordance with claim 8, wherein the air permeable blood barrier of the blood sequestration device includes a sealing material that seals the vent upon contact with blood.

14. The blood sequestration system in accordance with claim 8, wherein the air permeable blood barrier of the blood sequestration device includes a filter having a first layer and a second layer, the second layer of the filter having a hydrophobic material to repel blood.

15. A blood sequestration device
comprising; an inlet port;
an outlet port;
a sequestration chamber connected with the inlet port via a junction, the sequestration chamber having a vent that includes an air permeable blood barrier, the vent being defined by an outer wall that at least partially circumscribes the air permeable blood barrier, the vent further including a cap that at least partially covers the wall, the cap having a one-way seal abutting the air permeable blood barrier that inhibits air from entering the sequestration chamber; and
a sampling channel having a proximal end connected with the inlet port via the junction, and a distal end connected with the outlet port;
the sequestration chamber, the sampling channel and the junction being sized and configured such that a first portion of blood flows into and fills the sequestration chamber to displace air therein through the vent, and such that a second portion of blood bypasses the sequestration chamber and the first portion of blood sequestered therein and is directed into the sampling channel toward the outlet port.

16. The blood sequestration device in accordance with claim 15, further comprising a housing that houses and defines the inlet port, the outlet port, the sequestration chamber, and the sampling channel.

17. The blood sequestration device in accordance with claim 15, wherein the vent further includes an inner wall within the outer wall and that contains the air permeable blood barrier.

18. The blood sequestration device in accordance with claim 17, wherein the one-way seal is positioned over the inner wall and within the outer wall of the vent.

19. The blood sequestration device in accordance with claim 18, wherein the cap includes an inner surface that faces the air permeable blood barrier, the inner surface of the cap including a fulcrum against which the seal can flexibly unseal from the air permeable blood barrier to allow air to escape the sequestration chamber.

20. The blood sequestration device in accordance with claim 15, wherein the air permeable blood barrier includes a sealing material that seals the vent upon contact with blood.

* * * * *